US012662696B2

(12) United States Patent
Shomron et al.

(10) Patent No.: US 12,662,696 B2
(45) Date of Patent: Jun. 23, 2026

(54) METHOD AND SYSTEM FOR IDENTIFYING GENE DISORDER IN MATERNAL BLOOD

(71) Applicant: Ramot at Tel-Aviv University Ltd., Tel-Aviv (IL)

(72) Inventors: Noam Shomron, Tel-Aviv (IL); Tom Rabinowitz, Tel-Aviv (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 359 days.

(21) Appl. No.: 17/272,961

(22) PCT Filed: Sep. 3, 2019

(86) PCT No.: PCT/IL2019/050985
§ 371 (c)(1),
(2) Date: Mar. 3, 2021

(87) PCT Pub. No.: WO2020/049558
PCT Pub. Date: Mar. 12, 2020

(65) Prior Publication Data
US 2021/0340601 A1 Nov. 4, 2021

Related U.S. Application Data

(60) Provisional application No. 62/726,337, filed on Sep. 3, 2018.

(51) Int. Cl.
| | |
|---|---|
| *C12Q 1/6827* | (2018.01) |
| *C12Q 1/6883* | (2018.01) |
| *G16B 20/00* | (2019.01) |
| *G16B 30/10* | (2019.01) |
| *G16B 40/20* | (2019.01) |

(52) U.S. Cl.
CPC ......... *C12Q 1/6827* (2013.01); *C12Q 1/6883* (2013.01); *G16B 20/00* (2019.02); *G16B 30/10* (2019.02); *G16B 40/20* (2019.02)

(58) Field of Classification Search
CPC ............ C12Q 2600/156; C12Q 1/6883; C12Q 1/6827; C12Q 2600/112; C12Q 2600/172; G16B 20/00; G16B 20/20; G16B 20/10; G16B 30/00; G16B 40/00; G16B 30/10; G16B 20/40; G16B 15/00; G16B 5/20; G16B 45/00; G16H 10/40; G16H 50/20; G16H 50/30; G16H 10/60; G16H 70/60; G06N 20/00; G06N 3/08; G06F 17/18
USPC ............... 702/19, 20; 435/6.11, 6.1; 506/16; 703/11
See application file for complete search history.

(56) References Cited

U.S. PATENT DOCUMENTS

| | | | |
|---|---|---|---|
| 10,011,870 B2 * | 7/2018 | Zimmermann ...... | C12Q 1/6869 |
| 10,061,890 B2 * | 8/2018 | Rabinowitz ............ | G16B 20/20 |

| | | | |
|---|---|---|---|
| 2011/0105353 A1 | 5/2011 | Lo et al. | |
| 2016/0017412 A1 | 1/2016 | Srinivasan et al. | |
| 2016/0357904 A1 * | 12/2016 | Rabinowitz ............ | G16B 20/00 |
| 2021/0340601 A1 * | 11/2021 | Shomron ............. | C12Q 1/6883 |

FOREIGN PATENT DOCUMENTS

| | | | | |
|---|---|---|---|---|
| CN | 105648045 A | 6/2016 | | |
| CN | 105779280 A | 7/2016 | | |
| CN | 107922959 A | 4/2018 | | |
| CN | 109996894 A | 7/2019 | | |
| EP | 3847275 A1 | 7/2021 | | |
| WO | WO 2011/057094 | 5/2011 | | |
| WO | WO-2014055790 A2 * | 4/2014 | ............ | G16B 20/00 |
| WO | 2018/049049 A1 | 3/2018 | | |
| WO | WO 2020/049558 | 3/2020 | | |

OTHER PUBLICATIONS

Chang, M. Y. et al. (Dec. 2016) Development of novel noninvasive prenatal testing protocol for whole autosomal recessive disease using picodroplet PCR. Scientific Reports, vol. 6, e37153, 10 pages. (Year: 2016).*
Wikipedia, Bayesian inference discussion, downloaded Jun. 2025. (Year: 2025).*
SAM format parameters, 2024, Github. (Year: 2024).*
SAM optional parameters, 2024 github. (Year: 2024).*
Supplementary European Search Report and the European Search Opinion Dated May 16, 2022 From the European Patent Office Re. Application No. 19856626.7. (14 Pages).
Rabinowitz et al. "GitHub—Nshomron/Hoobari at 07713a512b9f2200b8b08c5e572bf80c810bc780 Hoobari—a Bayesian-Based Noninvasive Fetal Variant Detector", XP55917254AI, Retrieved from Internet, Sep. 1, 2018.
International Preliminary Report on Patentability Dated Mar. 18, 2021 From the International Bureau of WIPO Re. Application No. PCT/IL2019/050985. (9 Pages).
International Search Report and the Written Opinion Dated Dec. 2, 2019 From the International Searching Authority Re. Application No. PCT/IL2019/050985. (14 Pages).
Chan et al. "Second Generation Noninvasive Fetal Genome Analysis Reveals de Novo Mutations, Single-Base Parental Inheritance, and Preferred DNA Ends", Proc. Natl. Acad. Sci. USA, 113(50): E8159-E8168, Published Online Oct. 31, 2016.

(Continued)

*Primary Examiner* — Mary K Zeman
(74) *Attorney, Agent, or Firm* — Vorys, Sater, Seymour and Pease, LLP; Maryellen Feehery Hank

(57) ABSTRACT

A method of fetal genotyping, comprises receiving maternal genomic DNA (gDNA) data, maternal cell-free DNA (cfDNA) data, and paternal gDNA data of a pair parenting to a fetus. The data are analyzed to identify a first set of sites at which the parents are homozygous for different alleles, and a second set at which at least one of the parents has a mutation. For each site of the first set, a probability that a respective portion of the maternal cfDNA data is derived from the fetus is determined. Each site of the second set is classified according to the determined probabilities as being either fetal or maternal to genotype the fetus.

11 Claims, 66 Drawing Sheets
Specification includes a Sequence Listing.

(56)     References Cited

OTHER PUBLICATIONS

Feng et al. "Down Syndrome Prediction/Screening Model Based on Deep Learning and Illumina Genotyping Array", 2017 IEEE International Conference on Bioinformatics and Biomedicine, BIBM, Kansas City, MO, USA, Nov. 13-17, 2017, p. 347-352, Nov. 13, 2017.

Lam et al. "Noninvasive Prenatal Diagnosis of Monogenic Diseases by Targeted Massively Parallel Sequencing of Maternal Plasma: Application to Beta-Thalassemia", Clinical Chemistry, 58(10): 1467-1475, Published Online Aug. 15, 2012.

Ma et al. "Noninvasive Prenatal Diagnosis of 21-Hydroxylase Deficiency Using Target Capture Sequencing of Maternal Plasma DNA", Scientific Reports, 7(7427): 1-10, Published Online Aug. 7, 2017.

Rabinowitz et al. "Bayesian-Based Noninvasive Prenatal Diagnosis of Single-Gene Disorders", Genome Research, 29(3): 428-438, Published Online Feb. 20, 2019.

Vermeulen et al., "Sensitive Monogenic Noninvasive Prenatal Diagnosis by Targeted Haplotyping", The American Journal of Human Genetics, Sep. 7, 2017, pp. 326-339, vol. 101.

Ma et al., "Noninvasive prenatal diagnosis of 21-Hydroxylase deficiency using target capture sequencing of maternal plasma DNA", Scientific Reports, Aug. 7, 2017, pp. 1-10, DOI:10.1038/s41598-017-06828-2.

Chan et al. Size distributions of maternal and fetal DNA in maternal plasma. Clin. Chem. 50:1, 88-92 (2004).

Chen et al. Haplotype-assisted accurate non-invasive fetal whole genome recovery through maternal plasma sequencing. Genome Med. 5:18, 10 pages (2013).

Cirigliano et al. Performance of the neoBona test: a new paired-end massively parallel shotgun sequencing approach for cell-free DNA-based aneuploidy screening. Ultrasound Obstet. Gynecol. 49, 460-464 (2017).

Danecek et al. The variant call format and VCFtools. Bioinformatics 27:15, 2156-2158 (2011).

Fan et al. Analysis of the Size Distributions of Fetal and Maternal Cell-Free DNA by Paired-End Sequencing. Clin. Chem. 56:8, 1279-1286 (2010).

Fan et al. Non-invasive prenatal measurement of the fetal genome. Nature 487:7407, 320-324 (2012).

Fan et al. Noninvasive diagnosis of fetal aneuploidy by shotgun sequencing DNA from maternal blood. Proc. Natl. Acad. Sci. U. S. A. 105:42, 16266-16271 (2008).

Finning et al. A clinical service in the UK to predict fetal Rh (Rhesus) D blood group using free fetal DNA in maternal plasma. Ann. N. Y. Acad. Sci. 1022, 119-123 (2004).

Garrison et al. Haplotype-based variant detection from short-read sequencing. ArXiv12073907 Q-Bio, 9 pages, (2012).

Hill et al. Determination of fetal sex in pregnancies at risk of haemophilia: a qualitative study exploring the clinical practices and attitudes of health professionals in the United Kingdom. Haemophilia 18, 575-583 (2012).

Hill et al. Non-invasive prenatal diagnosis for cystic fibrosis: detection of paternal mutations, exploration of patient preferences and cost analysis. Prenat. Diagn. 35, 950-958 (2015).

Hwang et al. Systematic comparison of variant calling pipelines using gold standard personal exome variants. Sci. Rep. 5, 17875, 8 pages (2015).

Isakov et al. Exome sequencing analysis: a guide to disease variant detection. Methods Mol. Biol. 1038, 137-158 (2013).

Jenkins et al. Delivering an accredited non-invasive prenatal diagnosis service for monogenic disorders, and recommendations for best practice. Prenat. Diagn. 38, 44-51 (2017).

Jiang et al. The missing indels: an estimate of indel variation in a human genome and analysis of factors that impede detection. Nucleic Acids Res. 43:15, 7217-7228 (2015).

Kitzman et al. Noninvasive whole-genome sequencing of a human fetus. Sci. Transl. Med. 4:137, 18 pages (2012).

Lewis et al. Non-invasive prenatal diagnosis for fetal sex determination: benefits and disadvantages from the service users' perspective. Eur. J. Hum. Genet. EJHG 20, 1127-1133 (2012).

Li et al. Fast and accurate short read alignment with Burrows-Wheeler transform. Bioinformatics 25:14, 1754-1760 (2009).

Lo et al. Digital PCR for the molecular detection of fetal chromosomal aneuploidy. Proc. Natl. Acad. Sci. 104:32, 13116-13121 (2007).

Lo et al. Maternal Plasma DNA Sequencing Reveals the Genome-Wide Genetic and Mutational Profile of the Fetus. Sci. Transl. Med. 2:61, 14 pages (2010).

Lun et al. Noninvasive prenatal diagnosis of monogenic diseases by digital size selection and relative mutation dosage on DNA in maternal plasma. Proc. Natl. Acad. Sci. U. S. A. 105:50, 19920-19925 (2008).

Luo et al. Clairvoyante: a multi-task convolutional deep neural network for variant calling in Single Molecule Sequencing. bioRxiv 310458, 23 pages. 2018.

Mahdieh et al. An Overview of Mutation Detection Methods in Genetic Disorders. Iran. J. Pediatr. 23:4, 375-388 (2013).

Minon et al. Routine fetal RHD genotyping with maternal plasma: a four-year experience in Belgium. Transfusion 48:2, 373-381 (2008).

Mullaney et al. Small insertions and deletions (INDELs) in human genomes. Hum. Mol. Genet. 19:2, R131-R136 (2010).

Neuman et al. Analysis of insertion-deletion from deep-sequencing data: software evaluation for optimal detection. Brief. Bioinform. 14:1, 46-55 (2012).

Poplin et al. Creating a universal SNP and small indel variant caller with deep neural networks. bioRxiv 092890. 24 pages (2018).

Snyder et al. Haplotype-resolved genome sequencing: experimental methods and applications. Nat. Rev. Genet. 16, 344-358 (2015).

Snyder et al. Noninvasive fetal genome sequencing: a primer. Prenat. Diagn. 33:6, 547-554 (2013).

Sun et al. Coffee: control-free noninvasive fetal chromosomal examination using maternal plasma DNA. Prenat. Diagn. 37, 336-340 (2017).

Sequence Alignment/Map format specification, 23 pages, Jun. 3, 2021.

Torracinta et al. Training Genotype Callers with Neural Networks. bioRxiv 097469. 6 pages (2016).

Vora et al. Prenatal exome sequencing in anomalous fetuses: new opportunities and challenges. Genet. Med. 19:11, 1207-1216 (2017).

Yang et al. Clinical Whole-Exome Sequencing for the Diagnosis of Mendelian Disorders. N. Engl. J. Med. 369:16, 1502-1511 (2013).

Yu et al. Size-based molecular diagnostics using plasma DNA for noninvasive prenatal testing. Proc. Natl. Acad. Sci. 111:23, 8583-8588 (2014).

Mackie et al. Exome Sequencing in Fetuses with Structural Malformations. J. Clin. Med. 3, 747-762 (2014).

Meng et al. Use of Exome Sequencing for Infants in Intensive Care Units: Ascertainment of Severe Single-Gene Disorders and Effect on Medical Management. JAMA Pediatr. 171:12, e173438-e173438, 18 pages (2017).

Sillence. Cell-free fetal DNA (cffDNA) enrichment for non-invasive prenatal testing (NIPT): a comparison of molecular techniques. Thesis of Kelly A Sillence, submitted to the University of Plymouth, 311 pages (2016).

* cited by examiner

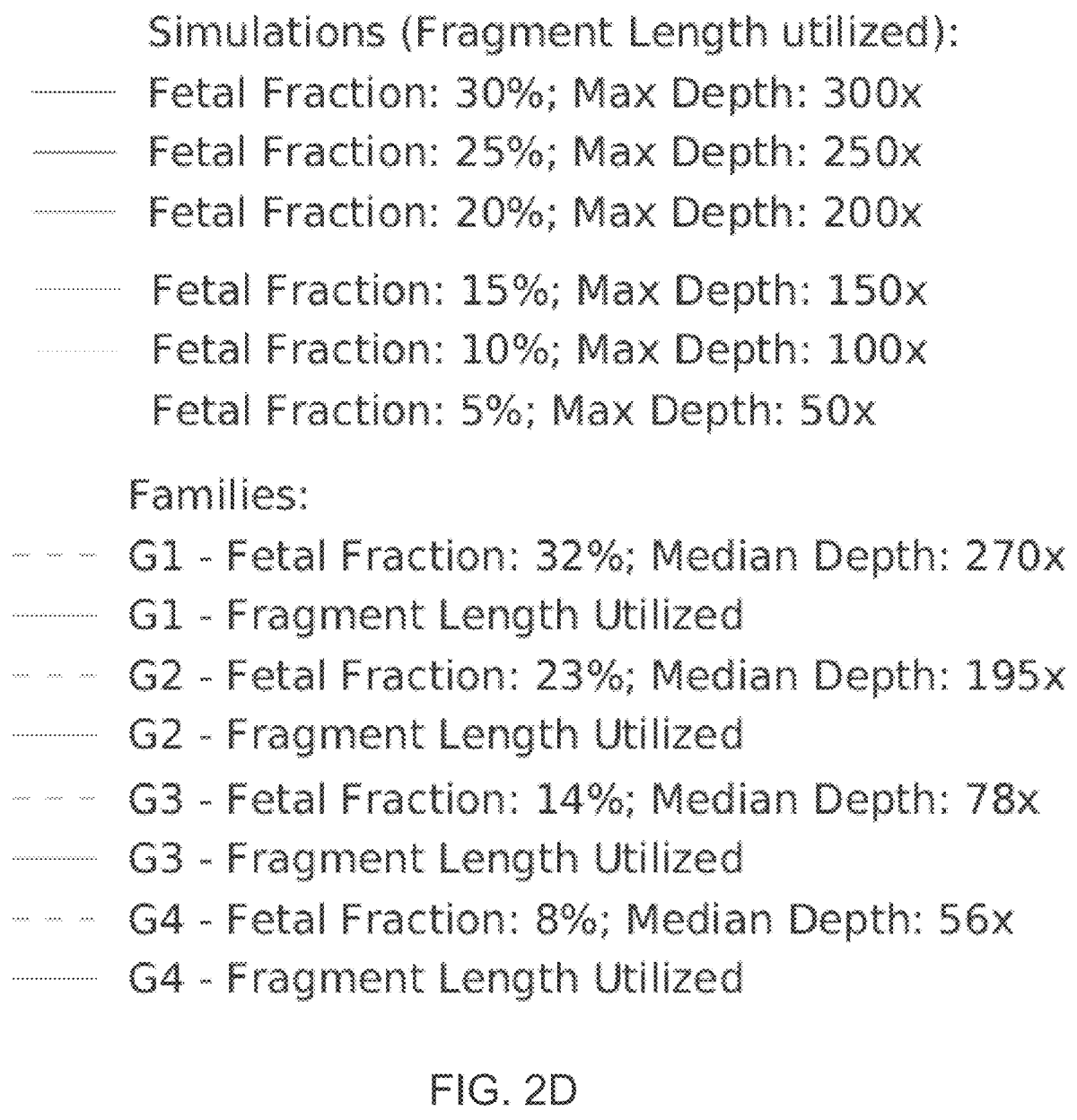

Simulations (Fragment Length utilized):

——————  Fetal Fraction: 30%; Max Depth: 300x

——————  Fetal Fraction: 25%; Max Depth: 250x

——————  Fetal Fraction: 20%; Max Depth: 200x

——————  Fetal Fraction: 15%; Max Depth: 150x

——————  Fetal Fraction: 10%; Max Depth: 100x

Fetal Fraction: 5%; Max Depth: 50x

Families:

— — —  G1 - Fetal Fraction: 32%; Median Depth: 270x

——————  G1 - Fragment Length Utilized

— — —  G2 - Fetal Fraction: 23%; Median Depth: 195x

——————  G2 - Fragment Length Utilized

— — —  G3 - Fetal Fraction: 14%; Median Depth: 78x

——————  G3 - Fragment Length Utilized

— — —  G4 - Fetal Fraction: 8%; Median Depth: 56x

——————  G4 - Fragment Length Utilized

FIG. 2D

Figure 3D:
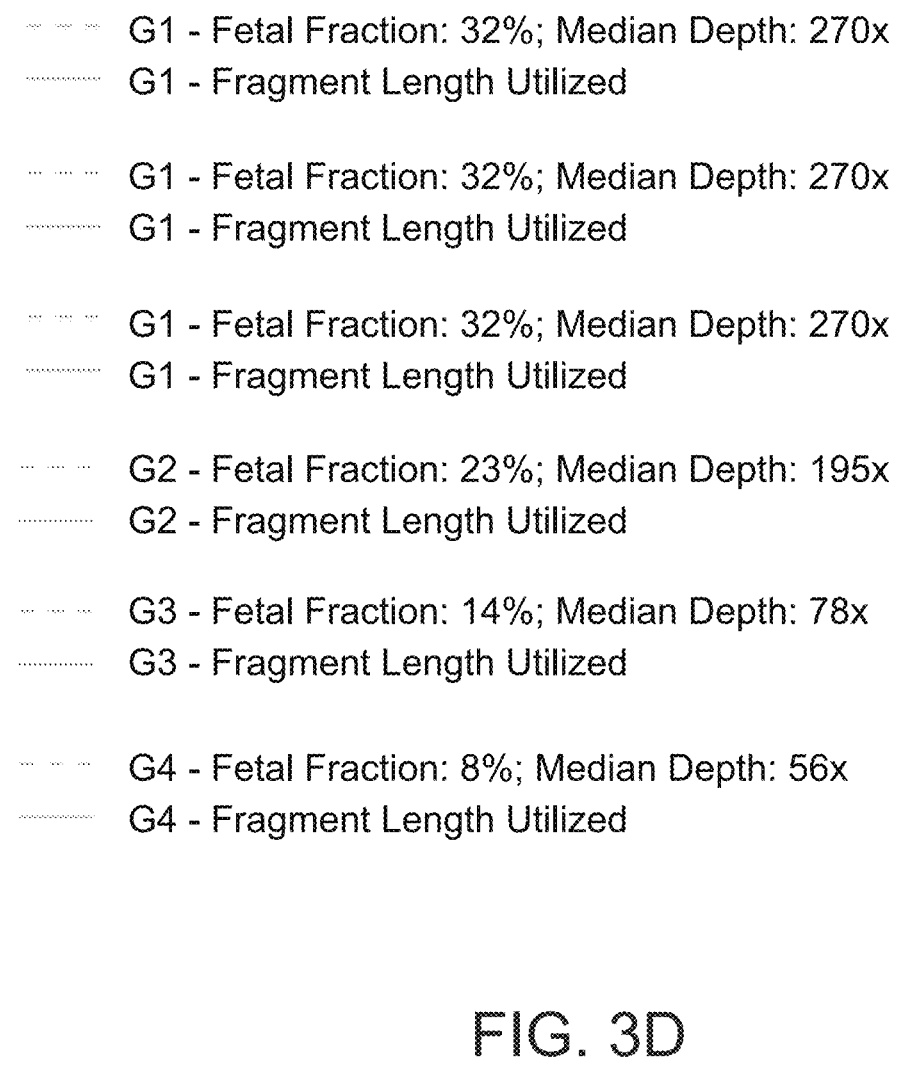

G1 - Fetal Fraction: 32%; Median Depth: 270x
G1 - Fragment Length Utilized

G1 - Fetal Fraction: 32%; Median Depth: 270x
G1 - Fragment Length Utilized

G1 - Fetal Fraction: 32%; Median Depth: 270x
G1 - Fragment Length Utilized

G2 - Fetal Fraction: 23%; Median Depth: 195x
G2 - Fragment Length Utilized

G3 - Fetal Fraction: 14%; Median Depth: 78x
G3 - Fragment Length Utilized

G4 - Fetal Fraction: 8%; Median Depth: 56x
G4 - Fragment Length Utilized

| 0.653 | 0.544 | 0.649 | 0.647 | 0.698 | 0.781 |
| 0.592 | 0.521 | 0.637 | 0.666 | 0.746 | 0.828 |
| 0.554 | 0.534 | 0.664 | 0.695 | 0.785 | 0.871 |
| 0.540 | 0.529 | 0.679 | 0.715 | 0.812 | 0.900 |
| 0.515 | 0.554 | 0.697 | 0.715 | 0.820 | 0.910 |
| 0.485 | 0.544 | 0.691 | 0.722 | 0.826 | 0.911 |
| 0-50 | 50-100 | 100-150 | 150-200 | 200-250 | 250-300 |

Sequencing depth 0.56     0.64     0.72     0.80     0.88

FIG. 4C

————— Family E1 (Fragment lengths utilized)

— — — Family E1

————— Family E2 (Fragment lengths utilized)

— — — Family E2

————— Family G5 (Fragment lengths utilized)

— — — Family G5

· · · · · · · Perfectly calibrated

‒ ‒ ‒ G2 (25%)

——— G2 (25%) recalibrated

‒ ‒ ‒ G5

——— G5 recalibrated

- - - G2 (25%)

——— G2 (25%) recalibrated

- - - G5

——— G5 recalibrated

SEQ ID:1
SEQ ID:2

SEQ ID:3
SEQ ID:4

SEQ ID:5
SEQ ID:6

SEQ ID:7
SEQ ID:8

Train_Accuracy_ParentalGroup_both-het

Train_Accuracy_TrueGenotype_homref

Val_Accuracy_ParentalGroup_both-het

Val_Accuracy_TrueGenotype_homref

Accuracy
tag: Train/Accuracy

Accuracy/TrueGenotype/homalt
tag: Train/Accuracy/TrueGenotype/homalt

Accuracy/ParentalGroup/both-het
tag: Train/Accuracy/ParentalGroup/both-het

Accuracy/TrueGenotype/homref
tag: Train/Accuracy/TrueGenotype/homref

Accuracy/ParentalGroup/mat-het
tag: Train/Accuracy/ParentalGroup/mat-het

Loss
tag: Train/Loss

Accuracy/ParentalGroup/pat-het
tag: Train/Accuracy/ParentalGroup/pat-het

Accuracy/TrueGenotype/het
tag: Train/Accuracy/TrueGenotype/het

Accuracy
tag: Val/Accuracy

Accuracy/TrueGenotype/homalt
tag: Val/Accuracy/TrueGenotype/homalt

Accuracy/ParentalGroup/both-het
tag: Val/Accuracy/ParentalGroup/both-het

Accuracy/TrueGenotype/homref
tag: Val/Accuracy/TrueGenotype/homref

Accuracy/ParentalGroup/mat-het
tag: Val/Accuracy/ParentalGroup/mat-het

Loss
tag: Val/Loss

Accuracy/ParentalGroup/pat-het
tag: Val/Accuracy/ParentalGroup/pat-het

Accuracy/TrueGenotype/het
tag: Val/Accuracy/TrueGenotype/het

Accuracy
tag: Train/Accuracy

Accuracy/TrueGenotype/het
tag: Train/Accuracy/TrueGenotype/het

Accuracy/ParentalGroup/both-het
tag: Train/Accuracy/ParentalGroup/both-het

Accuracy/TrueGenotype/homalt
tag: Train/Accuracy/TrueGenotype/homalt

Accuracy/ParentalGroup/mat-het
tag: Train/Accuracy/ParentalGroup/mat-het

Accuracy/TrueGenotype/homref
tag: Train/Accuracy/TrueGenotype/homref

Accuracy/ParentalGroup/pat-het
tag: Train/Accuracy/ParentalGroup/pat-het

Loss
tag: Train/Loss

Accuracy
tag: Val/Accuracy

Accuracy/TrueGenotype/het
tag: Val/Accuracy/TrueGenotype/het

Accuracy/ParentalGroup/both-het
tag: Val/Accuracy/ParentalGroup/both-het

Accuracy/TrueGenotype/homalt
tag: Val/Accuracy/TrueGenotype/homalt

Accuracy/ParentalGroup/mat-het
tag: Val/Accuracy/ParentalGroup/mat-het

Accuracy/TrueGenotype/homref
tag: Val/Accuracy/TrueGenotype/homref

Accuracy/ParentalGroup/pat-het
tag: Val/Accuracy/ParentalGroup/pat-het

Loss
tag: Val/Loss

SEQUENCE LISTING

```
<160> NUMBER OF SEQ ID NOS: 8

<210> SEQ ID NO 1
<211> LENGTH: 39
<212> TYPE: DNA
<213> ORGANISM: Homo sapiens
<220> FEATURE:
<221> NAME/KEY: misc_feature
<222> LOCATION: (7)..(8)
<223> OTHER INFORMATION: n is a, c, g, or t

<400> SEQUENCE: 1
ataagtnnca gtgctttctg gaatcatcca ggtgagcac                    39

<210> SEQ ID NO 2
<211> LENGTH: 39
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 2
ntargtnncr gtgctttctg grrtcrtccr ggtgrgcrc                    39

<210> SEQ ID NO 3
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
```

-continued

```
<400> SEQUENCE: 3
catcagtcac agtgctttct ngaatcntcc aggtgagcac c                    41

<210> SEQ ID NO 4
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 4
crtcrgtcrc rgtgctttct ngrrtcntcc rggtgrgcrc c                    41

<210> SEQ ID NO 5
<211> LENGTH: 41
<212> TYPE: DNA
<213> ORGANISM: Homo sapiens

<400> SEQUENCE: 5
catcagtcac agtgctttct tgaatcatcc aggtgagcac c                    41

<210> SEQ ID NO 6
<211> LENGTH: 41
<212> TYPE: DNA
<213> ORGANISM: Homo sapiens

<400> SEQUENCE: 6
crtcrgtcrc rgtgctttct tgrrtcrtcc rggtgrgcrc c                    41

<210> SEQ ID NO 7
<211> LENGTH: 41
<212> TYPE: DNA
<213> ORGANISM: Homo sapiens
<220> FEATURE:
<221> NAME/KEY: misc_feature
<222> LOCATION: (31)..(40)
<223> OTHER INFORMATION: n is a, c, g, or t

<400> SEQUENCE: 7
catcagtcac agtgctttct tgaatcatcc nnnnnnnnnn c                    41

<210> SEQ ID NO 8
<211> LENGTH: 41
<212> TYPE: DNA
<213> ORGANISM: Homo sapiens

<400> SEQUENCE: 8
gtrgtcrgtg tcrcgrrrgr rcttrgtrgg tccrctctgt g                    41
```

METHOD AND SYSTEM FOR IDENTIFYING GENE DISORDER IN MATERNAL BLOOD

RELATED APPLICATION

This application is a National Phase of PCT Patent Application No. PCT/IL2019/050985 having International filing date of Sep. 3, 2019, which claims the benefit of priority under 35 USC § 119(e) of U.S. Provisional Patent Application No. 62/726,337 filed on Sep. 3, 2018. The contents of the above applications are all incorporated by reference as if fully set forth herein in their entirety.

REFERENCE TO AN ELECTRONIC SEQUENCE LISTING

The contents of the electronic sequence listing (Sequence-Listing.txt; Size: 2,096 bytes; and Date of Creation: Jun. 16, 2024) is herein incorporated by reference in its entirety.

FIELD AND BACKGROUND OF THE INVENTION

The present invention, in some embodiments thereof, relates to bioinformatics and, more particularly, but not exclusively, to a method and system for identifying gene disorder in maternal blood.

The determination of copy number of genetic sequences in a fetus is of important diagnostic value. For example, in a dominant genetic disorder, the presence of a single copy of a disease causing allele causes the phenotypical expression of the genetic disorder. In contrast, in a recessive genetic disorder, the presence of a single copy of a disease causing allele only renders the individual a carrier, and does not cause the phenotypical expression of the genetic disorder. In addition, abnormal copy numbers of genetic sequences, e.g., chromosome segments or whole chromosomes in partial or complete aneuploidy, often cause various genetic disorders. For example, trisomy 21 causes Down Syndrome (DS).

Prenatal diagnosis is currently performed using conventional cytogenetic analysis (such as karyotyping) or DNA analysis, which require fetal genetic material to be obtained by amniocentesis, chorionic villus sampling or cordocentesis. However, these are invasive procedures and are associated with risks, such as a risk of fetal loss.

The advent of technologies that allow for sequencing entire genomes in relatively short time, and the discovery of circulating cell-free DNA (cfDNA) including both maternal and fetal DNA in the pregnant mother's blood have provided the opportunity to non-invasively analyze fetal genetic materials without the risks associated with invasive sampling methods. Known in the art are non-invasive prenatal diagnosis techniques for identifying specific chromosomal abnormalities, and for identifying single-gene disorders of paternal origin. Also known are non-invasive prenatal diagnosis techniques for ruling out single-gene disorders of maternal origin, fetal sex determination, and fetal Rhesus D genotyping.

SUMMARY OF THE INVENTION

According to some embodiments of the invention the present invention there is provided a method of fetal genotyping. The method comprises: receiving maternal genomic DNA (gDNA) data, maternal cell-free DNA (cfDNA) data, and paternal gDNA data of a pair parenting to a fetus; analyzing the data to identify a first set of sites at which the parents are homozygous for different alleles, and a second set of sites at which at least one of the parents has a mutation; for each site of the first set, determining a probability that a respective portion of the maternal cfDNA data is derived from the fetus; and classifying each site of the second set according to the probabilities as being either fetal or maternal to genotype the fetus.

According to some embodiments of the invention the analysis comprises identifying in reads covering the first set of sites a first group of reads including only reads that present paternal alleles but no other reads, and a second group including all other reads, and wherein the determining the probability is based on differences between reads in the first group and reads in the second group.

According to some embodiments of the invention the determination of the probably is based on at least one Sequence Alignment Map (SAM) parameter.

According to some embodiments of the invention the SAM parameter is selected from the group consisting of observed template length, length-dependent fetal fraction, CIGAR string, mate's CIGAR string, nucleotide sequence, mate's Nucleotide sequence, read alignment flag indicating whether or not a read paired, read alignment flag indicating whether or not a read mapped in proper pair, read alignment flag indicating whether or not a read unmapped, read alignment flag indicating whether or not a mate unmapped, read alignment flag indicating whether or not a read on the reverse strand, read alignment flag indicating whether or not a mate on the reverse strand, read alignment flag indicating whether or not a read first in pair, read alignment flag indicating whether or not a read second in pair, read alignment flag indicating whether or not a read not a primary alignment, read alignment flag indicating whether or not a read fail a platform and/or a vendor quality check, read alignment flag indicating whether or not a read a PCR or optical duplicate, read alignment flag indicating whether or not a read a supplementary alignment, mate's flag, mapping quality, mate's Mapping quality, genomic coordinates of chromosome, genomic coordinates of absolute start position on chromosome, genomic coordinates of absolute end position on chromosome, genomic coordinates of start position normalized per chromosome length, genomic coordinates of end position normalized per chromosome length, mate's genomic coordinates, number of G and C nucleotides divided by read length, number of G and C nucleotides divided by read length in mate's read sequence, Rate of A and/or C and/or G and/or T nucleotides within a nucleotide sequence of the read, rate of A and/or C and/or G and/or T nucleotides within the nucleotide sequence of the mate, information about a variant which the read or its mate originate from, including at least one of the features which appear in Table A.1, Kmer composition in the nucleotide sequence, Kmers composition in the mate's nucleotide sequence, nucleotide qualities sequence, matc's nucleotide qualities sequence, mean and/or standard error and/or median of nucleotide qualities sequence, mean and/or standard error and/or median of nucleotide qualities sequence, Kmer composition in the nucleotide qualities sequence, Kmer composition in the mate's nucleotide qualities sequence, number of methylated nucleotides divided by read length, and methylation in specific positions.

According to some embodiments of the invention the determination of the probably is based at least on an observed template length.

According to some embodiments of the invention the determination of the probably is based at least on a length-dependent fetal fraction.

According to some embodiments of the invention the determination of the probably is based at least on a CIGAR string.

According to some embodiments of the invention the determination of the probably is based at least on a nucleotide sequence.

According to some embodiments of the invention the determination of the probably is based at least on mate's nucleotide sequence.

According to some embodiments of the invention the determination of the probably is based on at least one read alignment flag, selected from the group consisting of: a read alignment flag indicating whether or not a read paired, a read alignment flag indicating whether or not a read mapped in proper pair, a read alignment flag indicating whether or not a read unmapped, a read alignment flag indicating whether or not a mate unmapped, a read alignment flag indicating whether or not a read on the reverse strand, a read alignment flag indicating whether or not a mate on the reverse strand, a read alignment flag indicating whether or not a read first in pair, a read alignment flag indicating whether or not a read second in pair, a read alignment flag indicating whether or not a read not a primary alignment, a read alignment flag indicating whether or not a read fail a platform and/or a vendor quality check, a read alignment flag indicating whether or not a read a PCR or optical duplicate, a read alignment flag indicating whether or not a read a supplementary alignment.

According to some embodiments of the invention the method comprises calculating a total fetal fraction, wherein the classifying comprises using also the total fetal fraction.

According to some embodiments of the invention the method comprises calculating a total fetal fraction, and constructing a fetal size distribution and a maternal size distribution, wherein the classifying comprises binning the fetal size distribution and calculating a fetal fraction for each fragment size bin, and calculating, for at least one site and at least one fragment at the at least one site, a probability that the fragment is fetal, based on a fetal fraction of a respective fragment size bin to which the fragment belongs.

According to some embodiments of the invention the classification comprises applying a Bayesian procedure.

According to some embodiments of the invention the Bayesian procedure comprises prior probabilities calculated using sequencing data of at least one of the parents.

According to some embodiments of the invention the sequencing of the data comprises whole genome sequencing (WGS).

According to some embodiments of the invention the sequencing of the data comprises whole exome sequencing (WES).

According to some embodiments of the invention the method comprises recalibration output of the Bayesian procedure using machine learning.

According to some embodiments of the invention the classifying comprises applying a machine learning procedure to the identified sites to genotype the fetus.

According to some embodiments of the invention the machine learning procedure comprises deep learning procedure.

According to some embodiments of the invention the method comprises recalibration output of the machine learning.

According to an aspect of some embodiments of the present invention there is provided a method of fetal genotyping. The method comprises: receiving maternal genomic DNA (gDNA) data, maternal cell-free DNA (cfDNA) data, and paternal gDNA data of a pair parenting to a fetus; accessing a computer readable medium storing a machine deep learning procedure trained for classifying sites in the data as being either fetal or maternal; feeding the procedure with the data; and receiving from the procedure an output indicative of fetal sites in the data, thereby genotyping the fetus.

According to some embodiments of the invention the method is applied to heterozygous sites of the maternal cfDNA data.

According to some embodiments of the invention the method is applied to homozygous sites of the maternal cfDNA data.

According to some embodiments of the invention the genotyping comprises identifying a fetal single-gene disorder (SGD) of paternal origin.

According to some embodiments of the invention the genotyping comprises identifying a fetal single-gene disorder (SGD) of maternal origin.

According to some embodiments of the invention the genotyping comprises predicting inherited insertions-deletions.

According to some embodiments of the invention the genotyping comprises identifying a fetal chromosomal abnormality.

According to some embodiments of the invention the method is executed for NIPD of a monogenic disease.

According to some embodiments of the invention the method is executed for NIPD of a multigenic disease.

According to some embodiments of the invention the method is executed for NIPD of a genetic disease selected from the group consisting of Bloom Syndrome, Canavan Disease, Cystic fibrosis, Familial Dysautonomia, Riley-Day syndrome, Fanconi Anemia (Group C), Gaucher Disease. Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease-juvenile, Connexin26, SMA, Rett syndrome, Phenylketonuria, Becker Muscular Dystrophy, Duchennes Muscular Dystrophy, Fragile X syndrome, Hemophilia A, Alzheimer dementia-early onset, Breast/Ovarian cancer, Colon cancer, Diabetes/MODY, Huntington disease, Myotonic Muscular Dystrophy, Parkinson Disease-early onset, Peutz-Jeghers syndrome, Polycystic Kidney Disease, Torsion Dystonia.

According to some embodiments of the invention the method is executed for NIPD of a genetic disease and further comprising administering prenatal or post-natal treatments for the genetic disease.

According to some embodiments of the invention the method is executed for NIPD of a congenital disorder.

According to some embodiments of the invention the congenital disorder is selected from the group consisting of a malformation, neural tube defect, chromosome abnormality, Down syndrome (or trisomy 21), Trisomy 18, spina bifida, cleft palate, Tay Sachs disease, sickle cell anemia, thalassemia, cystic fibrosis, Huntington's disease, and fragile x syndrome.

According to some embodiments of the invention the chromosome abnormality is selected from the group consisting of Down syndrome (extra chromosome 21), Turner Syndrome (45X0) and Klinefelter's syndrome (a male with 2 X chromosomes).

According to some embodiments of the invention the malformation comprises a limb malformation.

According to some embodiments of the invention the limb malformations is selected from the group consisting of amelia, ectrodactyly, phocomelia, polymelia, polydactyly, syndactyly, polysyndactyly, oligodactyly, brachydactyly, achondroplasia, congenital aplasia or hypoplasia, amniotic band syndrome, and cleidocranial dysostosis.

According to some embodiments of the invention the malformation comprises a congenital malformation of the heart.

According to some embodiments of the invention the congenital malformation is selected from the group consisting of patent ductus arteriosus, atrial septal defect, ventricular septal defect, and tetralogy of fallot.

According to some embodiments of the invention the malformation comprises a congenital malformation of the nervous system.

According to some embodiments of the invention the congenital malformation of the nervous system is selected from the group consisting of neural tube defects (e.g., spina bifida, meningocele, meningomyelocele, encephalocele and anencephaly), Arnold-Chiari malformation, the Dandy-Walker malformation, hydrocephalus, microencephaly, megencephaly, lissencephaly, polymicrogyria, holoprosencephaly, and agenesis of the corpus callosum.

According to some embodiments of the invention the malformation comprises a congenital malformation of the gastrointestinal system.

According to some embodiments of the invention the congenital malformation of the gastrointestinal system is selected from the group consisting of stenosis, atresia, and imperforate anus.

According to some embodiments of the invention the method comprises administering prenatal or post-natal treatment for the congenital disorder.

According to some embodiments of the invention the method comprises administering prenatal or post-natal treatment for the malformation.

According to some embodiments of the invention the method comprises administering prenatal or post-natal treatment selected from the group consisting of pharmaceutical based intervention, surgery, genetic therapy, nutritional therapy, and combinations thereof.

According to some embodiments of the invention the method comprises performing a pregnancy termination.

According to some embodiments of the invention the method comprises obtaining fetal genetic material when the genotyping indicates fetus abnormality or gene disorder, and analyzing the fetal genetic material to determine at least whether or not the fetus possesses the abnormality or gene disorder.

According to an aspect of some embodiments of the present invention there is provided a computer software product. The computer software product comprises a computer-readable medium in which program instructions are stored, which instructions, when read by a data processor, cause the data processor to receive maternal cfDNA data and paternal cfDNA data of a pair parenting to a fetus and to execute the method as delineated hereinabove and optionally and preferably as further detailed below.

According to an aspect of some embodiments of the present invention there is provided a system for fetal genotyping. The system comprises an input circuit receiving maternal cell-free DNA (cfDNA) data and paternal (cfDNA) data of a pair parenting to a fetus; a data processor configured for analyzing the data to identify sites at which the parents are homozygous for executing the method as delineated hereinabove and optionally and preferably as further detailed below.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-D show the relationship between the accuracy and posterior probabilities as obtained in experiments performed according to some embodiments of the present invention. Presented in FIGS. 2A-C are results for families G1-G4 and sub-sampled data for G1 ("Simulations"), in three categories of Single Nucleotide Polymorphism (SNP) positions determined by the parental genotypes. The x-axis shows the minimal threshold for the predictions' posterior probability, which indicates the level of certainty of the included loci. The y-axis shows accuracy among all sites with posterior probability above the threshold. The total accuracy appears at the lowest point on the x-axis, where the lowest possible threshold for maximal posterior probability is set (in FIGS. 2A and 2B, where there are two possible fetal genotypes for each locus, this value is 0.5; and in FIG. 2C it is 0.33 because all 3 fetal genotypes are possible). Also presented are the counts of total loci from which the accuracy was calculated at each threshold.

FIGS. 3A-D show calibration at indel sites in which a mother is heterozygous, as obtained in experiments performed according to some embodiments of the present invention. The format of FIGS. 3A-D are similar to FIGS. 2A-D but for indels. Accuracies are presented among loci with a posterior probability that is higher than the thresholds appearing in the x-axis. The same three categories of genomic sites are displayed in FIGS. 3A-C. The total accuracy for each category is the accuracy at the leftmost point on the x-axis (0.5 in FIGS. 3A and 3B, and 0.3 in 3C). The count of loci used for accuracy calculation at each threshold is presented at the bottom of each sub-figure.

FIGS. 4A-C are heat maps showing accuracy as a function of a sequencing depth and a fetal fraction, at the three categories of loci shown in FIGS. 2A-3D, as obtained in experiments performed according to some embodiments of the present invention.

DESCRIPTION OF SPECIFIC EMBODIMENTS OF THE INVENTION

Figure 1:
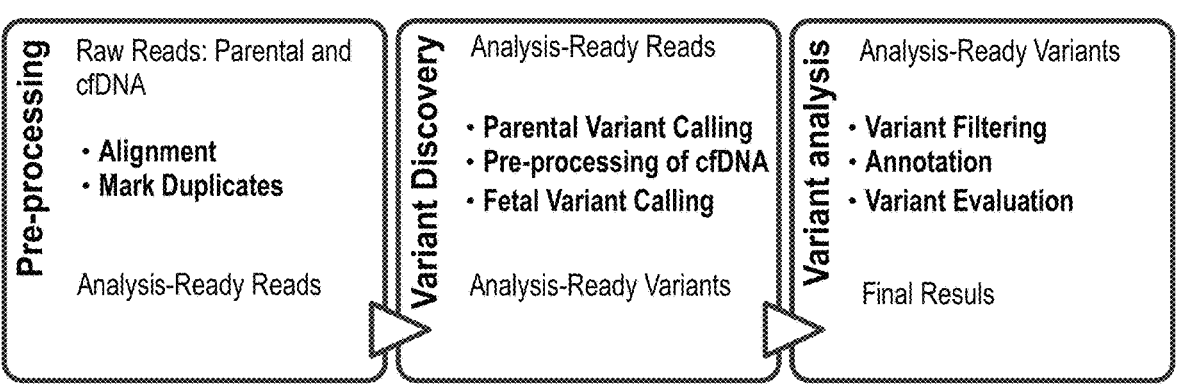
FIG. 1 is a schematic illustration of a pipeline for non-invasive prenatal variant calling, according to some embodiments of the present invention.

The present invention, in some embodiments thereof, relates to bioinformatics and, more particularly, but not exclusively, to a method and system for identifying gene disorder in maternal blood.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 15:
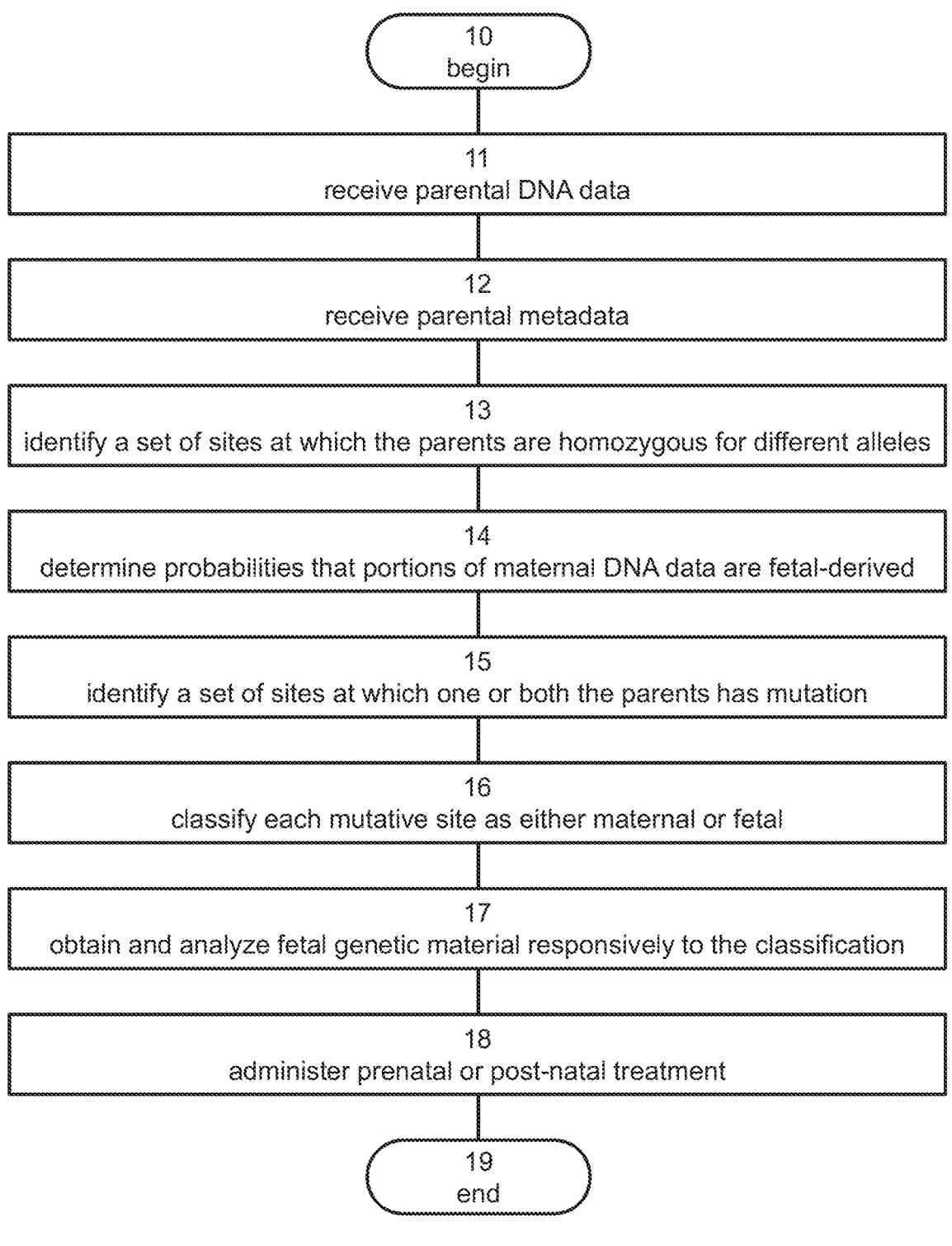
FIG. 15 is a flowchart diagram of a method suitable for fetal genotyping, according to various exemplary embodiments of the present invention.

FIG. 15 is a flowchart diagram of a method suitable for fetal genotyping, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The processing operations of the present embodiments can be embodied in many forms. For example, they can be embodied in on a tangible medium such as a computer for performing the operations. They can be embodied on a computer readable medium, comprising computer readable instructions for carrying out the method operations. They can also be embodied in electronic device having digital computer capabilities arranged to run the computer program on the tangible medium or execute the instruction on a computer readable medium.

Computer programs implementing the method according to some embodiments of this invention can commonly be distributed to users on a distribution medium such as, but not limited to, CD-ROM, flash memory devices, flash drives, or, in some embodiments, drives accessible by means of network communication, over the internet (e.g., within a cloud environment), or over a cellular network. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. Computer programs implementing the method according to some embodiments of this invention can also be executed by one or more data processors that belong to a cloud computing environment. All these operations are well-known to those skilled in the art of computer systems. Data used and/or provided by the method of the present embodiments can be transmitted by means of network communication, over the internet, over a cellular network or over any type of network, suitable for data transmission.

The method according to preferred embodiments of the present invention can be embedded into healthcare systems and may allow identification of fetal abnormalities or disorders, such as, but not limited to, fetal single-gene disorders (SGDs) of paternal and/or maternal origin, inherited insertions-deletions, chromosomal abnormalities, and/or monogenic or multigenic diseases, including, without limitation, Bloom Syndrome, Canavan Disease, Cystic fibrosis, Familial Dysautonomia, Riley-Day syndrome, Fanconi Anemia (Group C), Gaucher Disease, Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease-juvenile, Connexin26, SMA, Rett syndrome, Phenylketonuria, Becker Muscular Dystrophy, Duchennes Muscular Dystrophy, Fragile X syndrome, Hemophilia A, Alzheimer dementia-early onset, Breast/Ovarian cancer, Colon cancer, Diabetes/MODY, Huntington disease, Myotonic Muscular Dystrophy, Parkinson Disease-early onset, Peutz-Jeghers syndrome, Polycystic Kidney Disease, and Torsion Dystonia.

The method according to preferred embodiments of the present invention can allow identification of a fetal congenital disorder, e.g., neural tube defect, chromosome abnormality. Down syndrome (or trisomy 21). Trisomy 18, spina bifida, cleft palate, Tay Sachs disease, sickle cell anemia, thalassemia, cystic fibrosis, Huntington's disease, fragile x syndrome, Turner Syndrome (45X0), and Klinefelter's syndrome (a male with 2 X chromosomes).

The method according to preferred embodiments of the present invention can allow identification of a malformation, such as, but not limited to, a limb malformation, e.g., amelia, ectrodactyly, phocomelia, polymelia, polydactyly, syndactyly, polysyndactyly, oligodactyly, brachydactyly, achondroplasia, congenital aplasia or hypoplasia, amniotic band syndrome, and cleidocranial dysostosis, a congenital malformation of the heart, e.g., patent ductus arteriosus, atrial septal defect, ventricular septal defect, and tetralogy of fallot, a congenital malformation of the nervous system, e.g., neural tube defects (e.g., spina bifida, meningocele, meningomyelocele, encephalocele and anencephaly). Arnold-Chiari malformation, the Dandy-Walker malformation, hydrocephalus, microencephaly, megencephaly, lissencephaly, polymicrogyria, holoprosencephaly, and agenesis of the corpus callosum, a congenital malformation of the gastro-intestinal system, e.g., stenosis, atresia, and imperforate anus, The method begins at 10 and continues to 11 at which DNA data of a pair parenting to a fetus is received. The DNA data can be received by the method from a computer readable medium storing the DNA data. The DNA data preferably include at least maternal genomic DNA (gDNA) data, maternal cell-free DNA (cfDNA) data, and paternal gDNA data. In some embodiments of the present invention the DNA data includes only genotypes, and is devoid of read-level information, or devoid of nucleotide-level information, or devoid of both read-level information and nucleotide-level information.

As used herein, "genotype" refers to the diploid combination of alleles at a given genetic locus, or set of related loci, in a given parental or fetal cell. A homozygous subject carries two copies of the same allele and a heterozygous subject carries two distinct alleles. In the simplest case of a locus with two alleles "A" and "a", three genotypes may be formed: A/A, A/a, and a/a. More than two allelic forms may exist, thus there may be more than three possible genotypes.

The genotypes of the parents can be determined by genotyping.

As used herein, "genotyping" a subject (or DNA sample) for a polymorphic allele of a gene(s) refers to detecting which allelic or polymorphic form(s) of the gene(s) are present in a subject (or a sample).

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

Optionally, the method continues to 12 at which metadata pertaining to one or both the parents is received. The received metadata optionally and preferably includes at least one, more preferably more than one, of the features listed in Table A.1 in ANNEX 1.

The method continues to 13 at which the data are analyzed to identify a first set of sites at which the parents are homozygous for different alleles. This is optionally and preferably executed at least for each site of the maternal DNA data. Operating 13 can be executed using a variant calling technique in individuals, based on sequencing of DNA, alignment to the genome, application of a commercially available variant caller, and filtering or choosing from the resulted variant list those sites at which the parents are homozygous for different alleles are.

Sequence alignment techniques that can be used according to some embodiments of the present invention include, without limitation, Burrows Wheeler Aligner (BWA), ABA, ALE, AMAP, anon, BAli-Phy, Basc-By-Base, BHAOS/DIALIGN, Bowtic, Bowtie 2, ClustalW, CodonCode Aligner, Comass, DECIPHER, DIALIGN-TX, DIALIGN-T, DNA Alignment, DNA Baser Sequence Assembler, EDNA, FSA, Gencious, Kalign, MAFFT, MARNA, MAVID, MSA, MSAProbs, MULTALIN, Multi-LAGEN, MUSCLE, Opal, Pecan, Phylo, Praline, PicXAA, POA, Probalign, ProbCons, PROMALS3D, PRRN/PRRP, PSAlign, RevTrans, SAGA, SAM, Se—Al, STAR, STAR-Fusion, StatAlign, Stemloc, T-Coffee, UGENE, VectorFriends, and GLProbs Exemplary variant callers suitable for the present embodiments include, without limitation, Genome Analysis Toolkit (GATK) and Freebayes. For example, Freebayes can comprise an alignment based on literal sequences of reads aligned to a particular target, not their precise alignment. GATK can comprise: (i) pre-Processing; (ii) variant discovery, and (iii) callset refinement. Pre-Processing can comprise starting from raw sequence data, e.g., in FASTQ or uBAM format, and producing analysis-ready BAM files, processing can include alignment to a reference genome as well as data cleanup operations to correct for technical biases and make the data suitable for analysis, variant discovery can comprise starting from analysis-ready BAM files and producing a callset in VCF format, processing can involve identifying sites where one or more individuals display possible genomic variation, and applying filtering methods appropriate to the experimental design, callset refinement can comprise starting and ending with a VCF callset, processing can involve using metadata to assess and improve genotyping accuracy, attach additional information and evaluate the overall quality of the callset.

Also contemplated are variant callers such as, but not limited to. Platypus. VarScan. Bowtie analysis. MuTect and/or SAMtools. For example. Bowtie analysis can comprise implementing the Burrows-Wheeler transform for aligning. MuTect can comprise: (i) pre-processing; (ii) statistical analysis; and (iii) post-processing. Pre-processing can comprise an initial alignment of sequencing reads, statistical analysis can comprise using two Bayesian classifiers, one classifier can detect whether a SNP is non-reference at a given site and, for those sites that are found as non-reference, the other classifier can make sure the normal does not carry the SNP, post-processing can comprise removal of artifacts of sequencing, short read alignments and hybrid capture. SAMtools can comprise storing, manipulating and aligning sequencing reads stored as SAM files.

In various exemplary embodiments of the invention the method proceeds to 14 at which, for each site of the first set, a probability that a respective portion of maternal cfDNA data is derived from the fetus is determined. Operation 14 is advantageous since it allows the method to obtain information pertaining to the differences in the maternal DNA data between reads that are fetal-derived and reads that are maternal-derived. This can be done by searching over the first set for reads that present paternal allele, and defining each site that is covered by one or more of such reads, and preferably by no other reads, as a fetal-derived site. All fetal-derived sites of the first set define a first group within the first set. The remaining sites of the first set define a second group within the first set. The differences between the characteristics of the reads that that cover the sites in the first group, and the characteristics of the reads that cover the sites in the second group are then used for determining the probability that a particular site of the maternal cfDNA data is fetal-derived.

The method can also proceed to 15 at which the data are analyzed to identify a second set of sites at which at least one of the parents has a mutation. Operation 15 can be executed using any of the commercially available techniques described above with respect to operation 13, except that for operation 15 except that sites at which none of the parents has a mutation are filtered out from the output. The second set preferable includes at least one site, and more preferably a plurality of sites, that do not belong to the first set. However, the first and second sets of site need not necessarily be disjoint, since a site at which the parents are homozygous for different alleles can in principle present a mutation. Yet, since the probability of each site of the first set has already been determined at 14, the present embodiments contemplate a scenario in which the first and second sets are disjoint sets.

The method proceeds to 16 at which each site of second set is classified as being either fetal or maternal, according to the probabilities obtained at 14. The genotype at each site that is classified as fetal can then be extracted, thereby genotyping the fetus.

In some embodiments of the present invention the method proceeds to 17 at which fetal genetic material is obtained and analyzed. Preferably. 17 is executed when the genotyping at 16 indicates fetus abnormality or gene disorder, in which case the analysis 17 is directed to determine at least whether or not the fetus possesses the abnormality or gene disorder.

In some embodiments of the present invention the method proceeds to 18 at which prenatal or post-natal treatment is administered. For example, when the method identifies a fetal genetic disease at 17 or 18, prenatal or post-natal treatment for the identified fetal genetic disease can be administered, when the method identifies a congenital disorder at 17 or 18, prenatal or post-natal treatment for the congenital disorder can be administered, when the method identifies malformation at 17 or 18, prenatal or post-natal treatment for the malformation. Other prenatal or post-natal treatment that are contemplated according to some embodiments of the present invention including, without limitation, pharmaceutical based intervention, surgery, genetic therapy, nutritional therapy, and combinations thereof. In some embodiments of the present invention a pregnancy termination is executed.

The method ends at 19.

The determination of the probabilities at 14 and the classification 16 can be done in more than one way.

In some embodiments of the present invention the determination at 14 is based on one or more Sequence Alignment Map (SAM) parameters. SAM is a known format for storing biological data, such as, but not limited to, nucleotide sequences, and defines various parameters, referred to herein as SAM parameters. A description of the specification of the SAM format can be found at www(dot)samtools(dot)github (dot)io/hts-specs/SAMv1(dot)pdf, the contents of which are hereby incorporated by reference.

Representative examples of SAM parameters suitable for the present embodiments include, without limitation, observed template length, length-dependent fetal fraction, CIGAR string, mate's CIGAR string, nucleotide sequence, mate's Nucleotide sequence, read alignment flag indicating whether or not a read paired, read alignment flag indicating whether or not a read mapped in proper pair, read alignment flag indicating whether or not a read unmapped, read alignment flag indicating whether or not a mate unmapped, read alignment flag indicating whether or not a read on the reverse strand, read alignment flag indicating whether or not a mate on the reverse strand, read alignment flag indicating whether or not a read first in pair, read alignment flag indicating whether or not a read second in pair, read alignment flag indicating whether or not a read not a primary alignment, read alignment flag indicating whether or not a read fail a platform and/or a vendor quality check, read alignment flag indicating whether or not a read a PCR or optical duplicate, read alignment flag indicating whether or not a read a supplementary alignment, mate's flag, mapping quality, mate's Mapping quality, genomic coordinates of chromosome, genomic coordinates of absolute start position on chromosome, genomic coordinates of absolute end position on chromosome, genomic coordinates of start position normalized per chromosome length, genomic coordinates of end position normalized per chromosome length, mate's genomic coordinates, number of G and C nucleotides divided by read length, number of G and C nucleotides divided by read length in mate's read sequence, Rate of A and/or C and/or G and/or T nucleotides within a nucleotide sequence of the read, rate of A and/or C and/or G and/or T nucleotides within the nucleotide sequence of the mate, information about a variant which the read or its mate originate from, including at least one of the features which appear in Table A.1, Kmer composition in the nucleotide sequence, Kmers composition in the mate's nucleotide sequence, nucleotide qualities sequence, mate's nucleotide qualities sequence, mean and/or standard error and/or median of nucleotide qualities sequence, mean and/or standard error and/or median of nucleotide qualities sequence. Kmer composition in the nucleotide qualities sequence, Kmer composition in the mate's nucleotide qualities sequence, number of methylated nucleotides divided by read length, and methylation in specific positions.

In some embodiments of the present invention the probability at 14 is determined based at least on an observed template length, in some embodiments of the present invention the probability at 14 is determined based at least on a length-dependent fetal fraction, in some embodiments of the present invention the probability at 14 is determined based at least on a CIGAR string, in some embodiments of the present invention the probability at 14 is determined based at least on a nucleotide sequence, in some embodiments of the present invention the probability at 14 is determined based at least on a mate's nucleotide sequence.

In some embodiments of the present invention the probability at 14 is determined based at least on at least one read alignment flag. Representative examples of read alignment flag suitable for the present embodiments include, without limitation, a read alignment flag indicating whether or not a read paired, a read alignment flag indicating whether or not a read mapped in proper pair, a read alignment flag indicating whether or not a read unmapped, a read alignment flag indicating whether or not a mate unmapped, a read alignment flag indicating whether or not a read on the reverse strand, a read alignment flag indicating whether or not a mate on the reverse strand, a read alignment flag indicating whether or not a read first in pair, a read alignment flag indicating whether or not a read second in pair, a read alignment flag indicating whether or not a read not a primary alignment, a read alignment flag indicating whether or not a read fail a platform and/or a vendor quality check, a read alignment flag indicating whether or not a read a PCR or optical duplicate, a read alignment flag indicating whether or not a read a supplementary alignment.

The present embodiments also contemplate calculating a total fetal fraction. In these embodiments, the classification 16 is optionally and preferably based on the calculated total fetal fraction. Further contemplated are embodiments in which a fetal size distribution and a maternal size distribution are constructed. In these embodiments the classification 16 optionally and preferably comprises binning the fetal size distribution, calculating a fetal fraction for each fragment size bin, and calculating, for at least one site and at least one fragment at the at least one site, a probability that the fragment is fetal, based on a fetal fraction of a respective fragment size bin to which the fragment belongs. In some embodiments optionally and preferably the classification at 16 comprises applying a Bayesian procedure. The Bayesian procedure optionally and preferably comprises prior probabilities calculated using sequencing data (e.g., genome sequencing, or whole exome sequencing) of at least one of the parents.

In some embodiments of the present invention the determination of the probabilities at 14, and optionally and preferably also the classification at 16, comprises applying a machine learning procedure.

As used herein the term "machine learning" refers to a procedure embodied as a computer program configured to induce patterns, regularities, or rules from previously collected data to develop an appropriate response to future data, or describe the data in some meaningful way.

Representative examples of machine learning procedures suitable for the present embodiments, include, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, convolutional neural networks, instance-based algorithms, linear modeling algorithms, k-nearest neighbors (KNN) analysis, ensemble learning algorithms, probabilistic models, graphical models, logistic regression methods (including multinomial logistic regression methods), gradient ascent methods, singular value decomposition methods and principle component analysis.

Following is an overview of some machine learning procedures suitable for the present embodiments.

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

In KNN analysis, the affinity or closeness of objects is determined. The affinity is also known as distance in a feature space between objects. Based on the determined distances, the objects are clustered and an outlier is detected. Thus, the KNN analysis is a technique to find distance-based outliers based on the distance of an object from its kth-nearest neighbors in the feature space. Specifically, each object is ranked on the basis of its distance to its kth-nearest neighbors. The farthest away object is declared the outlier. In some cases the farthest objects are declared outliers. That is, an object is an outlier with respect to parameters, such as, a k number of neighbors and a specified distance, if no more than k objects are at the specified distance or less from the object. The KNN analysis is a classification technique that uses supervised learning. An item is presented and compared to a training set with two or more classes. The item is assigned to the class that is most common amongst its k-nearest neighbors. That is, compute the distance to all the items in the training set to find the k nearest, and extract the majority class from the k and assign to item.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the datasets. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

The aforementioned self-organizing map is an unsupervised learning technique often used for visualization and analysis of high-dimensional data. Typical applications are focused on the visualization of the central dependencies within the data on the map. The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the response to the treatment. Symmetrical uncertainty is an algorithm that can be used by a feature selection algorithm, according to some embodiments of the present invention. Symmetrical uncertainty compensates for information gain's bias towards features with more values by normalizing features to a [0,1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the probability that a respective portion of DNA data is derived from a fetus, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the datasets or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular parameter influences on the probability that a respective portion of DNA data is derived from a fetus) or a value (e.g., the probability that a respective portion of DNA data is derived from a fetus). The leaf nodes can also contain additional information about the represented classification such as a confidence score that measures a confidence level in the represented classification (i.e., the accuracy of the prediction).

Regression techniques which may be used in accordance with some embodiments the present invention include, but are not limited to linear Regression. Multiple Regression, logistic regression, probit regression, ordinal logistic regression ordinal Probit-Regression. Poisson Regression, negative binomial Regression, multinomial logistic Regression (MLR) and truncated regression.

A logistic regression or logit regression is a type of regression analysis used for predicting the outcome of a categorical dependent variable (a dependent variable that can take on a limited number of values, whose magnitudes are not meaningful but whose ordering of magnitudes may or may not be meaningful) based on one or more predictor variables. Logistic regression may also predict the probability of occurrence for each data point. Logistic regressions also include a multinomial variant. The multinomial logistic regression model is a regression model which generalizes logistic regression by allowing more than two discrete outcomes. That is, it is a model that is used to predict the probabilities of the different possible outcomes of a categorically distributed dependent variable, given a set of independent variables (which may be real-valued, binary-valued, categorical-valued, etc.). For binary-valued variables, a cutoff between the 0 and 1 associations is typically determined using the Yuden Index.

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions of the probability that a respective portion of DNA data is derived from a fetus. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based techniques generate a new model for each instance, instead of basing predictions on trees or networks generated (once) from a training set.

The term "instance", in the context of machine learning, refers to an example from a dataset.

Instance-based techniques typically store the entire dataset in memory and build a model from a set of records similar to those being tested. This similarity can be evaluated, for example, through nearest-neighbor or locally weighted methods, e.g., using Euclidian distances. Once a set of records is selected, the final model may be built using several different techniques, such as the naive Bayes.

Neural networks are a class of algorithms based on a concept of inter-connected "neurons." In a typical neural network, neurons contain data values, each of which affects the value of a connected neuron according to connections with pre-defined strengths, and whether the sum of connections to each particular neuron meets a pre-defined threshold. By determining proper connection strengths and threshold values (a process also referred to as training), a neural network can achieve efficient recognition of images and characters. Oftentimes, these neurons are grouped into layers in order to make connections between groups more obvious and to each computation of values. Each layer of the network may have differing numbers of neurons, and these may or may not be related to particular qualities of the input data.

In one implementation, called a fully-connected neural network, each of the neurons in a particular layer is connected to and provides input value to those in the next layer. These input values are then summed and this sum compared to a bias, or threshold. If the value exceeds the threshold for a particular neuron, that neuron then holds a positive value which can be used as input to neurons in the next layer of neurons. This computation continues through the various layers of the neural network, until it reaches a final layer. At this point, the output of the neural network routine can be read from the values in the final layer. Unlike fully-connected neural networks, convolutional neural networks operate by associating an array of values with each neuron, rather than a single value. The transformation of a neuron value for the subsequent layer is generalized from multiplication to convolution.

The machine learning procedure used according to some embodiments of the present invention is a trained machine learning procedure, optionally and preferably a deep learning procedure (e.g., a convolutional neural network), which provides output that is related non-linearly to the parameters with which it is fed.

It is expected that during the life of a patent maturing from this application many relevant machine learning procedures will be developed and the scope of the term machine learning procedure is intended to include all such new technologies a priori.

A machine learning procedure, optionally and preferably a deep learning procedure, such as, but not limited to, a convolutional neural network, can be trained according to some embodiments of the present invention by feeding a machine learning training program with DNA data and optionally and preferably metadata as further detailed hereinabove for each of a cohort of subjects parenting a genotyped fetus. When a convolutional neural network is employed, the input to the network is typically, but not necessarily, in the form of multi-dimensional tensors. For example, each tensor can include input data corresponding to a certain locus in the genome. In preferred embodiments, the tensor is a pileup of reads that cover a candidate Single nucleotide polymorphism (SNP) (e.g., centered around the SNP). The first two dimensions of the tensor can correspond, for example, to the length of the pileup and the number of reads, and one or more additional dimensions of the tensor can correspond to metadata for the SNP. In the training phase, each tensor is associated with a label comprising the true fetal genotypes that are found using an invasive test.

Once the data are fed, the machine learning training program generates a trained machine learning procedure which can then be used without the need to re-train it, and without the need to feed it with fetal genotypes that are found using an invasive test. The trained machine learning procedure can provide the probability that a portion of the maternal DNA data is derived from a fetus, and/or it can classify a site at which at least one of the parents has a mutation as being either fetal or maternal.

The trained machine learning procedure is preferably employed as an end-to-end procedure, in which case the DNA data is fed to the trained machine learning procedure, and an output indicative of the probability that a site is derived from a fetus, or, more preferably an output classifying sites at which at least one of the parents has a mutation as being either fetal or maternal, can be received from the trained machine learning procedure.

Alternatively, the trained machine learning procedure can be used as supplementary for other techniques and be used, for example, for recalibration. For example, in embodiments in which the classification at 16 is by a Bayesian procedure, the trained machine learning procedure can be used for recalibrating the output of the Bayesian procedure.

Further contemplated, are embodiments in which the output of the trained machine learning procedure is used for retraining the machine learning procedure, thereby allowing the accuracy to be improved over time.

Fetal genotyping can be executed according to some embodiments of the present invention by a computer or a server-client computer configuration, as will now be explained with reference to FIG. 16.

Figure 16:
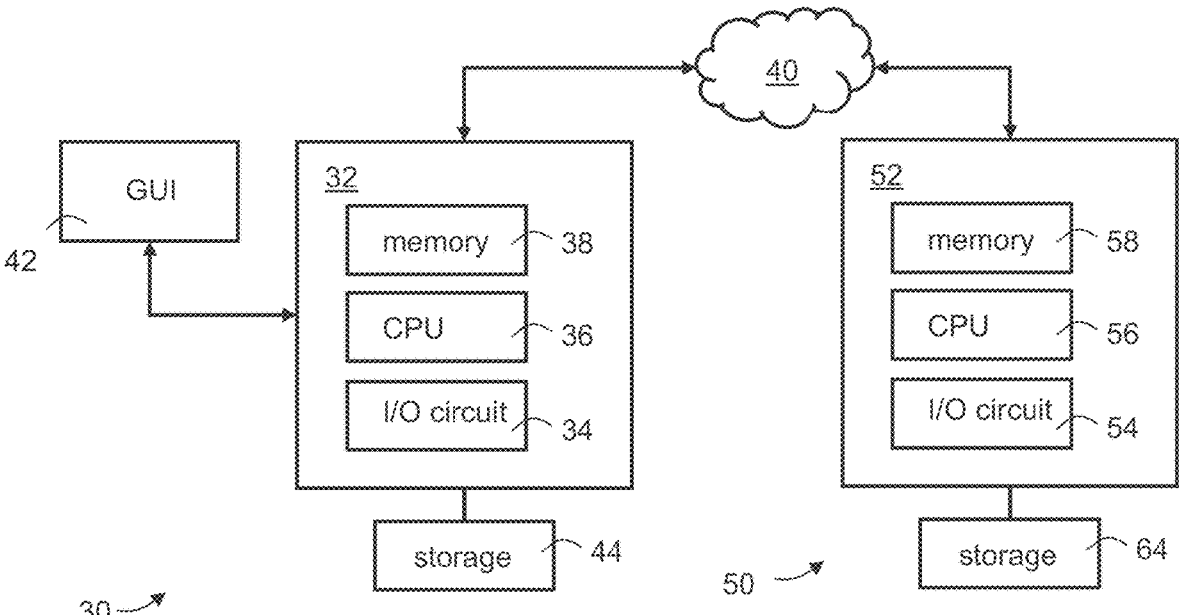
FIG. 16 is a schematic illustration of a server-client computer configuration which can be used for fetal genotyping according to some embodiments of the present invention.

FIG. 16 illustrates a client computer 30 having a hardware processor 32, which typically comprises an input/output (I/O) circuit 34, a hardware central processing unit (CPU) 36 (e.g., a hardware microprocessor), and a hardware memory 38 which typically includes both volatile memory and non-volatile memory. CPU 36 is in communication with I/O circuit 34 and memory 38. Client computer 30 preferably comprises a user interface, e.g., a graphical user interface (GUI). 42 in communication with processor 32. I/O circuit 34 preferably communicates information in appropriately structured form to and from GUI 42. Also shown is a server computer 50 which can similarly include a hardware processor 52, an I/O circuit 54, a hardware CPU 56, a hardware memory 58. I/O circuits 34 and 54 of client 30 and server 50 computers preferable operate as transceivers that communicate information with each other via a wired or wireless communication. For example, client 30 and server 50 computers can communicate via a network 40, such as a local area network (LAN), a wide area network (WAN) or the Internet. Server computer 50 can be in some embodiments be a part of a cloud computing resource of a cloud computing facility in communication with client computer 30 over the network 40.

GUI 42 and processor 32 can be integrated together within the same housing or they can be separate units communicating with each other. GUI 42 can optionally and preferably be part of a system including a dedicated CPU and I/O circuits (not shown) to allow GUI 42 to communicate with processor 32. Processor 32 issues to GUI 42 graphical and textual output generated by CPU 36. Processor 32 also receives from GUI 42 signals pertaining to control commands generated by GUI 42 in response to user input. GUI 42 can be of any type known in the art, such as, but not limited to, a keyboard and a display, a touch screen, and the like. In preferred embodiments, GUI 42 is a GUI of a mobile device such as a smartphone, a tablet, a smartwatch and the like. When GUI 42 is a GUI of a mobile device, the CPU circuit of the mobile device can serve as processor 32 and can execute the method optionally and preferably by executing code instructions.

Client 30 and server 50 computers can further comprise one or more computer-readable storage media 44, 64, respectively. Media 44 and 64 are preferably non-transitory storage media storing computer code instructions for executing the method of the present embodiments, and processors 32 and 52 execute these code instructions. The code instructions can be run by loading the respective code instructions into the respective execution memories 38 and 58 of the respective processors 32 and 52. Storage media 64 preferably also store one or more databases including a database of psychologically annotated olfactory perception signatures as further detailed hereinabove.

In operation, processor 32 of client computer 30 receives DNA data and optionally and preferably metadata as further detailed hereinabove. The data can be read, for example, from storage medium 44. Processor 32 typically transmits the data to server computer 50 over network 40. Medium 64 can store a procedure for genotyping a fetus as further detailed hereinabove (e.g., a deep learning procedure, and/or a Bayesian procedure). Server computer 50 can access media 64, feed the stored procedure with the data received from client computer 30, and receive from the procedure an output indicative of the genotypes of the fetus, or of the probability that a portion of the data (e.g., a mutative site) is fetal-derived. Server computer 50 can also transmit to client computer 30 the obtained output, and client computer 30 can display this information on GUI 42.

Alternatively, medium 44 can store also the procedure for genotyping the fetus as further detailed hereinabove, in which case the entire method can be executed by computer 30. Specifically, computer 30 can store the DNA data it received from medium 44 into memory 38, access medium 44 to obtain the procedure for genotyping the fetus, feed the stored procedure with the data that was stored in memory 38, and receive from the procedure an output indicative of the genotypes of the fetus, or of the probability that a portion of the data (e.g., a mutative site) is fetal-derived. Computer 30 can then display this information on GUI 42.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Non-Invasive Parental Diagnosis (NIPD) is a test for genetic alterations in the fetus, which is based on cell-free DNA (cfDNA) fragments circulate freely in the blood plasma. During pregnancy, cfDNA in the maternal plasma contains cell-free fetal DNA (cffDNA), originating from placental cells. The amount of cffDNA, also called fetal fraction, constitute approximately 10% of the cfDNA during the end of the first trimester of pregnancy, and increases in the next trimesters. NIPD is available today primarily of chromosomal abnormalities (e.g. Down syndrome).

NIPD of point-mutations is a more challenging task, since compared to a whole chromosome, the amount of cffDNA that covers a given genomic position is considerably lower. In mutations for which only the father is a carrier, the presence of the foreign (non-maternal) allele in the maternal plasma can be modeled as a binomial distribution; if enough DNA fragments in the maternal plasma contain the foreign allele, it can be deduced that it was inherited. Detection of a mutation in the fetus in such positions is, therefore, considered more straightforward. In mutations for which only the mother is heterozygous, both alleles are present in large quantities in her plasma, regardless of the identity of the inherited allele. The common solution to this problem is to measure the amount of each allele. If they have equal amounts, the fetus is assumed to be a carrier of the mutation, i.e. a heterozygous; if there is an allelic imbalance, then the fetus is homozygous to the allele that is present in an excessive amount.

Measuring subtle allelic imbalances requires an ultra-accurate quantification method, such as digital-PCR. It was realized by the Inventors that this method requires a bespoke design for each case, and hence, it is not suitable for testing a large number of mutations simultaneously. Another option is to use next generation sequencing (NGS), which is a less accurate method, but to do so with a very deep coverage (i.e., each position is read many times), and with special preparation protocols that can reduce artifacts. Few methods were suggested for NGS-based genome-wide NIPD of point mutations (Chan et al. 2016; Fan et al. 2012; Kitzman et al. 2012).

It was found by the Inventors that for SGDs of maternal origin, sensitivity poses a challenge that limits the testing to one genetic disorder at a time. Example 1 below presents a Bayesian method for the NIPD of monogenic diseases that is independent of mode of inheritance and parental origin. Sequenced parental and fetal data were used to calibrate and validate the model. Example 1 shows that accounting for differences in the fragment length distribution of fetal- and maternal-derived cfDNA results in increased accuracy. The model of Example 1 extends to prediction of inherited insertions-deletions (indels). Example 1 also shows that recalibrating the posterior probabilities of the model using data from previously analyzed families through a machine learning algorithm corrects a significant number of genotyping errors. In Example 1, the method of the present embodiments was successfully applied to predict the inheritance of congenital chloride diarrhea in a pregnancy where the parents were carriers of a mutation. This Example demonstrates that next generation sequencing (NGS) can be used for the NIPD of a wide range of monogenic diseases, simultaneously. This Example demonstrates that the method of the present embodiments can serve as a general framework for the NIPD of SGDs.

Typically, NIPD it is achieved by analyzing cfDNA in the maternal plasma, which contains cffDNA derived from the placenta. Its main use is for identifying chromosomal abnormalities, such as trisomy (Down syndrome). Other clinical applications are fetal sex determination and Rhesus D genotyping. Genetic diagnosis of SGDs is known to be achieved by various ways, from the phenotypic description and a linkage analysis, through different laboratory tests, such as polymerase chain reaction (PCR) and DNA microarrays for known mutations, to Sanger sequencing for confirmation of results and NGS for a deeper investigation. Two known tools are whole exome sequencing (WES) and whole genome sequencing (WGS), which are based on NGS. While the cost of WGS is still high and the implications of its results are less studied, WES, which covers about 2-3% of the genome and is less costly, remains more commonly used. However, WGS is more reliable than WES even in exome variants, and together with its ability to resolve structural variations, it is becoming more popular. WES of infants who are suspected to have genetic disorders is more likely to affect medical care. WES of DNA obtained by amniocentesis can assist the prenatal diagnosis in several cases.

The inventors found that although the application of NGS for the NIPD of monogenic diseases has been shown to be feasible, some improvements can still be made. Unlike the identification of paternally transmitted allele in cfDNA which is considered to be straightforward, maternally transmitted alleles pose a greater challenge, since in sites where the mother is heterozygous, both alleles are present in her plasma. In these cases, conventional technique cannot determine with confidence which of the alleles was inherited. The current solution is to look for an allelic imbalance (a slightly higher amount of one allele that appears when the fetus is homozygous). However, owing to the low amounts of cfDNA, and even lower amounts of cffDNA, its execution is restricted to ultra-accurate devices such as digital PCR. Moreover, this method is not scalable; when more than a few genomic sites are tested, it becomes less feasible and thus less helpful. NGS can be also used, and it requires a very deep coverage of each site.

Known is a technique that uses WES to provide deeper coverage [Fan. H. C. et al. Non-invasive prenatal measurement of the fetal genome. Nature 487, 320-324 (2012)]. In this technique a high percentage of the fetal exome was reconstruct when using deep WES, 221× and 631×, in the second and third trimesters, respectively. Stringent data filtering was applied before the analysis. In another attempt to genotype a fetus, cfDNA was sequenced using WGS to a deep coverage (270×) and a sequential probability ratio test was applied per site in loci where the mother is heterozygous, with no haplotyping of the parents [Chan, K. C. A. et al. Second generation noninvasive fetal genome analysis reveals de novo mutations, single-base parental inheritance, and preferred DNA ends. Proc. Natl. Acad. Sci. 201615800 (2016). doi: 10.1073/pnas. 1615800113]. While this study showed good accuracy the present inventors found several limitations in this technique. Firstly, the sequenced sample was from a third trimester pregnancy, in which both the amount of cfDNA and the fraction of cffDNA within it are high. Secondly, the applied method did not utilize available information about the paternal inheritance. Thirdly, it is not clear whether a sequential test has an advantage when genotyping a single position, since the data in this case is not cumulative. Additionally, in this study, accuracy was calculated from a relatively low number of only $6.5×10^5$ sites where the mother was heterozygous.

The inventors found that an approach that can assist in improving noninvasive fetal genotyping can rely on inherent differences in fetal and maternal features. One such difference is the actual cfDNA and cffDNA fragments. For example, fetal-derived fragments are generally shorter, and the pattern of their size distribution indicates a relationship with nucleosome positioning. Attempts were made to utilize size differences for chromosomal abnormalities, by applying with a hard threshold set in order to enrich for cffDNA. However, the inventors found that such threshold can lead to loss of relevant information, since the two size distributions largely overlap.

Example 1, below, shows that by using deep NGS, together with an improved algorithm, it is possible to accurately detect small variants in the fetus in a noninvasive manner. Example 1 uses a Bayesian model to demonstrate accurate detection of small variants in the fetus even in positions for which the mother or both parents are carriers of a mutation, and in small insertions and deletions (indels), all of which are considered harder to genotype. The prior probability was computed using the parental genotypes, based on simple Mendelian inheritance laws, and the likelihood function was based on the support of each cfDNA fragment in each possible fetal genotype. The fragment lengths were also utilized in the likelihood function, as fetal and maternal fragments were previously described to differ in their length distribution. Both the length distributions and the fetal fraction (i.e., the rate of cffDNA within the cfDNA) can be empirically calculated from a given a cfDNA sample. The Bayesian model was also supplemented by a machine learning recalibration procedure.

Example 2, below, presents an end-to-end method based on a deep learning procedure. The deep learning procedure can replace the Bayesian model and the machine learning recalibration procedure used in Example 1. One of the advantages of the end-to-end method presented in Example 2 is its ability to automatically model systematic errors. This is useful in data that is harder to interpret, such as low-depth sequencing. Deep learning is rapidly becoming available, as both the programming methods are becoming simple to handle, and hardware's price is decreasing.

Example 1

This Example describes a technique for noninvasive prenatal variant calling, termed Hoobari by the present inventors. The Hoobari technique is based on a Bayesian algorithm that uses the information of each read separately. The technique can be fine-tuned in a modular manner, without having to rewrite the entire model. One example of this is a machine learning-based probabilities recalibration step. The technique uses fragment size differences in order to improve fetal genotyping. This is particularly useful with challenging loci where the mother is heterozygous. The technique presented in this example can be generalized, to allow predicting the inheritance of small insertions and deletions (indels). Using deep WES (>600×) of two first trimester cases, and deep WGS (310×) of another first trimester case, the present inventors demonstrated the ability of the technique to resolve the diagnosis based on NGS, leading to NIPD of a wide range of SGDs.

Materials and Methods

Single nucleotide polymorphisms (SNPs) where the mother was heterozygous were considered. Since it is hard to determine whether a fragment is fetal or maternal at these sites, each fragment's probability for being fetal was calculated, depending on its size, and these probabilities were used in a Bayesian classifying model.

Using sites at which the parents are homozygous for different alleles, two empirical size distributions were created: a fetal empirical size distribution and a maternal empirical size distribution. In these sites, a cfDNA fragment that shows the paternal allele is very likely to be fetal. The total fetal fraction, which is the fraction of cffDNA within all maternal cfDNA, was calculated. A fetal fraction for each fragment size was then calculated, using all fragments with the same length. When applying the Bayesian model on a certain genomic site-of-interest, the per-size fetal fraction was used for the calculation of each fragment's probability of being fetal, for all the fragments that cover the site. In this way, shorter fragments generally received a higher probability of being fetal, and a stringent size-threshold could be avoided.

FIG. 1 schematically illustrates the Hoobari's pipeline for noninvasive prenatal variant calling. The code returns three posterior probabilities, one for each possible fetal genotype: homozygous to the reference allele (0/0), heterozygous (0/1), and homozygous to the alternate allele (1/1). The predicted genotype at each site is the one with the highest probability. Fetal variants that were found using a pure fetal sample, such as amniotic fluid, chorionic villi, or umbilical cord blood were used as the true variants.

The pipeline is different from regular variant calling workflows in that the prior probabilities were calculated with high confidence using existing parental sequencing data obtained from an initial genotyping of the parents. Additionally, cfDNA is an unbalanced mixture of two similar genomes. Therefore, the pipeline is different from regular variant calling workflows also in the dedicated technique that is used for calculating the likelihoods in the Bayesian model. This technique uses the cfDNA fragment length distribution, which is calculated in a pre-processing step.

Following is a more detailed description of the study.

Processing of Families from Previous Studies

The technique of the present embodiments was tested on whole-genome data of four family trios that were sequenced to different depths of coverage in previous studies, and where the fetal fraction within the cfDNA varies. The families are referred to as G1, G2, G3 and G4. Samples from families G1-2 and families G3-G4 were collected and sequenced as described in Chan, K. C. A. et al., supra, and Kitzman. J. O. et al. Noninvasive whole-genome sequencing of a human fetus. Sci. Transl. Med. 4, 137ra76 (2012).

Sample Collection and DNA Extraction

Samples from each family were collected during week 11 with informed consent. DNA from chorionic villus sampling (CVS) was extracted using the DNA Tissue protocol for the MagNA Pure Compact Nucleic Acid Isolation Kit I—Large Volume (Roche Life Science). Peripheral maternal blood was collected using 2-4 Ethylene-diamine-tetra-acetic acid (EDTA) tubes. Plasma was separated from blood by centrifugation at 4° C. for 10 minutes at 1600×g. The plasma was then centrifuged again at 16,000×g for 10 minutes at room temperature to remove any residual cells. Extraction of cfDNA was performed using the QIAamp Circulating Nucleic Acid Kit (Qiagen). Removal of excess salts resulting from cfDNA purification was conducted using Agencourt AMPure XP beads (Beckman Coulter, Inc.) at a 2× ratio to cfDNA volume. Pure maternal DNA was extracted from leukocytes in the maternal buffy coats, using a protocol that includes (i) buffy coat separation and (ii) DNA purification using the Gentra Puregene Blood Kit (Qiagen) according to the manufacturer's instructions. Pure paternal DNA was collected and purified similarly.

Library Preparation and Sequencing

Library preparation for samples that underwent WGS was performed using the TruSeq DNA PCR-Free Library Prep Kit (Illumina) according to the manufacturer's instructions. This was followed by sequencing using the HiSeq X Ten System (Illumina) with 151-bp paired-end reads.

For samples that underwent WES, library preparation was performed using the SureSelect V5 Exome Kit (Agilent) according to the manufacturer's instructions. Enrichment was achieved by hybridizing prepared genomic DNA to complementary RNA probe. Sequencing was then performed using HiSeq 4000 (Illumina) with 101-bp paired-end reads.

Cell-free DNA samples were not fragmented during library preparation, and were sequenced in two steps: (1) to a requested coverage of 50×, using HiSeq 4000 (Illumina) with 101-bp paired-end reads; and (2) to a requested coverage of 950×, using NovaSeq (Illumina) with 151-bp paired-end reads.

Alignment to the Genome

Reads were aligned to the Genome Reference Consortium Human Build 37 (GRCh37/hg19) using Burrows-Wheeler v0.7.834 with default parameters. Duplicate reads, resulting from PCR clonality or optical duplicates, and reads mapping to multiple locations were excluded from downstream analysis.

Variant Calling of Pure Genomic Sequencing Data

Single-nucleotide substitutions and small insertions and deletions were identified using the Freebayes software v1.1.0-3-g961e5f335 applying default parameters. Freebayes was first run on the aligned sequencing data of both parents together, then on the aligned data of the CVS sample using the variant sites that were identified in the parental genomes. Reported variants were not filtered, so that all reported SNPs and indels were kept for downstream analysis.

Pre-Processing of Cell-Free DNA Data

Freebayes was run on the cfDNA sample only at variant sites that were identified in the parental genomes. Using Hoobari, the allele that was observed by each read, together with the read insert-size, was saved in a separate database.

Noninvasive Fetal Variant Calling

Hoobari was run using the parental variants and the cfDNA pre-processing results database as input. The output was a standard variant call format (VCF) file. The analysis of the results was held using several software dedicated for VCF manipulation, such as vcflib and vcftools.

Bayesian Noninvasive Genotyping

At each site of interest, a Bayesian calculation was applied. For each possible fetal genotype:

$$P(G \mid \text{data}) = \frac{P(\text{data} \mid G)P(G)}{\sum_{i=1}^{n} P(\text{data} \mid G_i)P(G_i)}$$

where G is the fetal genotype and $G_i$ is the ith possible fetal genotype out of n possibilities. For bi-allelic variants, it would be either homozygous for the reference allele (AA), heterozygous (Aa), or homozygous for the alternate allele (aa). P(G) is the prior probability for each genotype, and was calculated by Mendelian laws. The data variable denotes the reads that cover a site and P(data|G) denotes the likelihood function, which is defined in this Example as a product of the likelihood of each read:

$$P(\text{data} \mid G) =$$
$$\prod_{j=1}^{m} P(r_j \mid G, G_M, f) = \prod_{j=1}^{m} (P(r_j \mid fet)P(fet) + P(r_j \mid mat)P(mat)).$$

The likelihood of a read $r_j$ depends on the fetal genotype, and is calculated using the maternal genotype and the fetal fraction. $P(r_j|\text{fet})$ and $P(r_j|\text{mat})$ are the probabilities of a read-observation that supports a certain allele, given that the read is fetal or maternal, respectively. This depends on the tested fetal genotype $G_i$, the maternal genotype $G_M$ and the observed allele. P(fet) and P(mat) are the probabilities of observing a fetal or maternal read based only on the fetal fraction, and regardless of the allele that it supports. In order to utilize the size differences between fetal and maternal fragments, the fetal fraction used for each read was calculated only from reads with the same fragment size. For reads that are not properly paired or have a fragment size of >500, the total fetal fraction is used.

Confirmation of the Mutation in Family E1

Following the previous birth of an affected offspring, a deleterious nonsense mutation (NM_000111.2, c.559G>T) in gene SLC26A3 was found in both parents using Sanger sequencing. This mutation causes congenital chloride diarrhea (CCD), which is inherited in an autosomal recessive mode. Using Sanger sequencing of the CVS sample, the fetus sequenced in this study was confirmed as homozygous to the mutation.

Results

Utilizing Fragment Sizes for Fetal Genotyping

In each family, the genomic DNA of all individuals was sequenced to coverage that ranged between 25× and 60×. The cfDNA samples were sequenced to depths of 270×, 195×, 78× and 56× (see Table 1, below). The total fetal fraction was calculated to be 32.4%, 24.9%, 14% and 8.7% respectively. The four cases were therefore classified according to two coverage levels: high (G1-2) and low (G3-4).

TABLE 1

Summary of samples from previous studies.

| Family | Individual | Sample | Depth of Coverage |
|---|---|---|---|
| G1 | Mother | White blood cells | 40 |
| | | Plasma (38 wk) | 270 |
| | Father | White blood cells | 45 |
| | Offspring | Umbilical cord blood | 50 |
| G2 | Mother | White blood cells | 40 |
| | | Plasma (18 wk) | 195 |
| | Father | White blood cells | 60 |
| | Offspring | Placental tissues | 60 |
| G3 | Mother | White blood cells | 32 |
| | | Plasma (18.5 wk) | 78 |
| | Father | Saliva | 39 |
| | Offspring | Umbilical cord blood | 40 |
| G4 | Mother | White blood cells | 25 |
| | | Plasma (8.2 wk) | 56 |
| | Father | Saliva | 33 |
| | Offspring | Umbilical cord blood | 44 |

The method of the present embodiments was executed for each family to test the calibration of the method algorithm, using the relationship between the posterior probabilities and the accuracy, and to determine whether adding fragment sizes increases the accuracy.

Figure 2A:
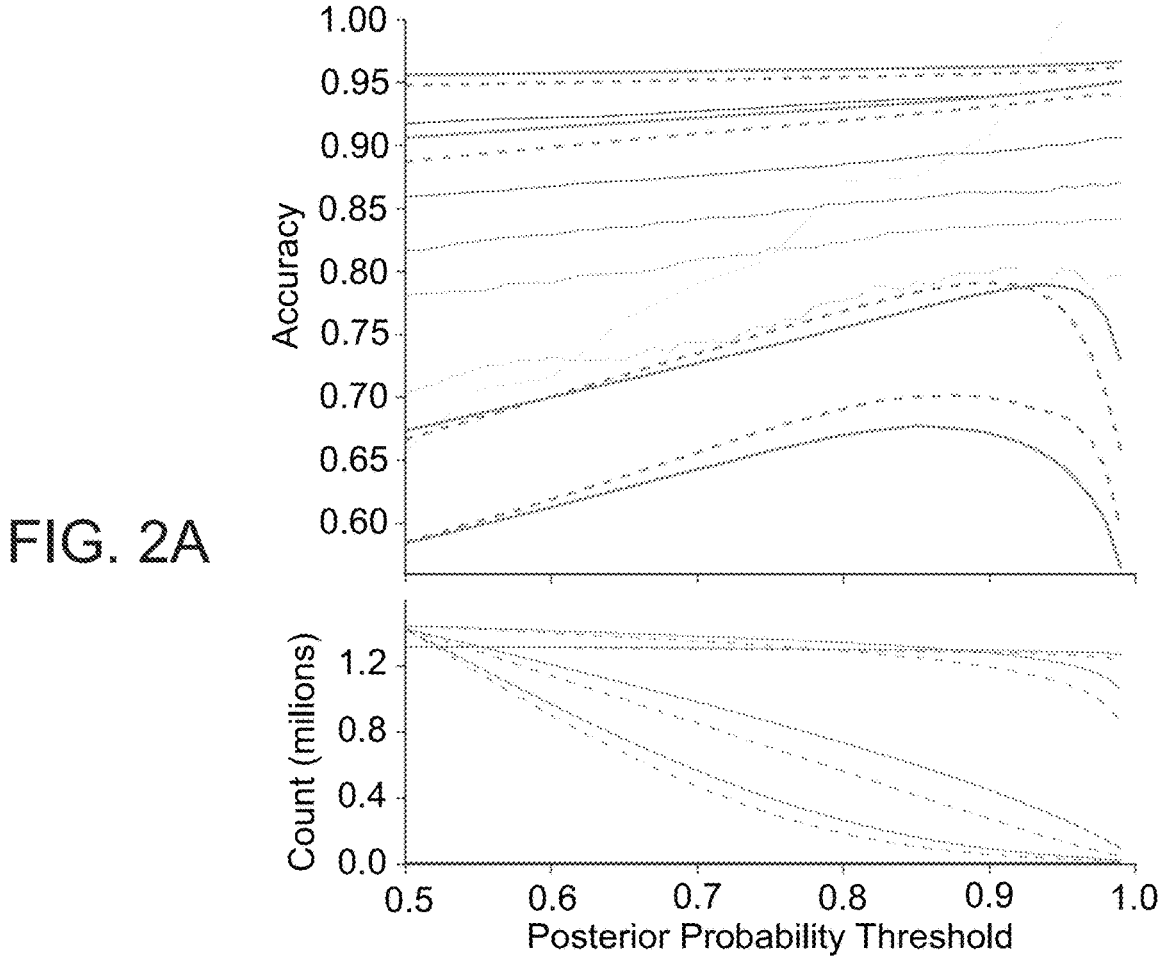
Figure 2B:
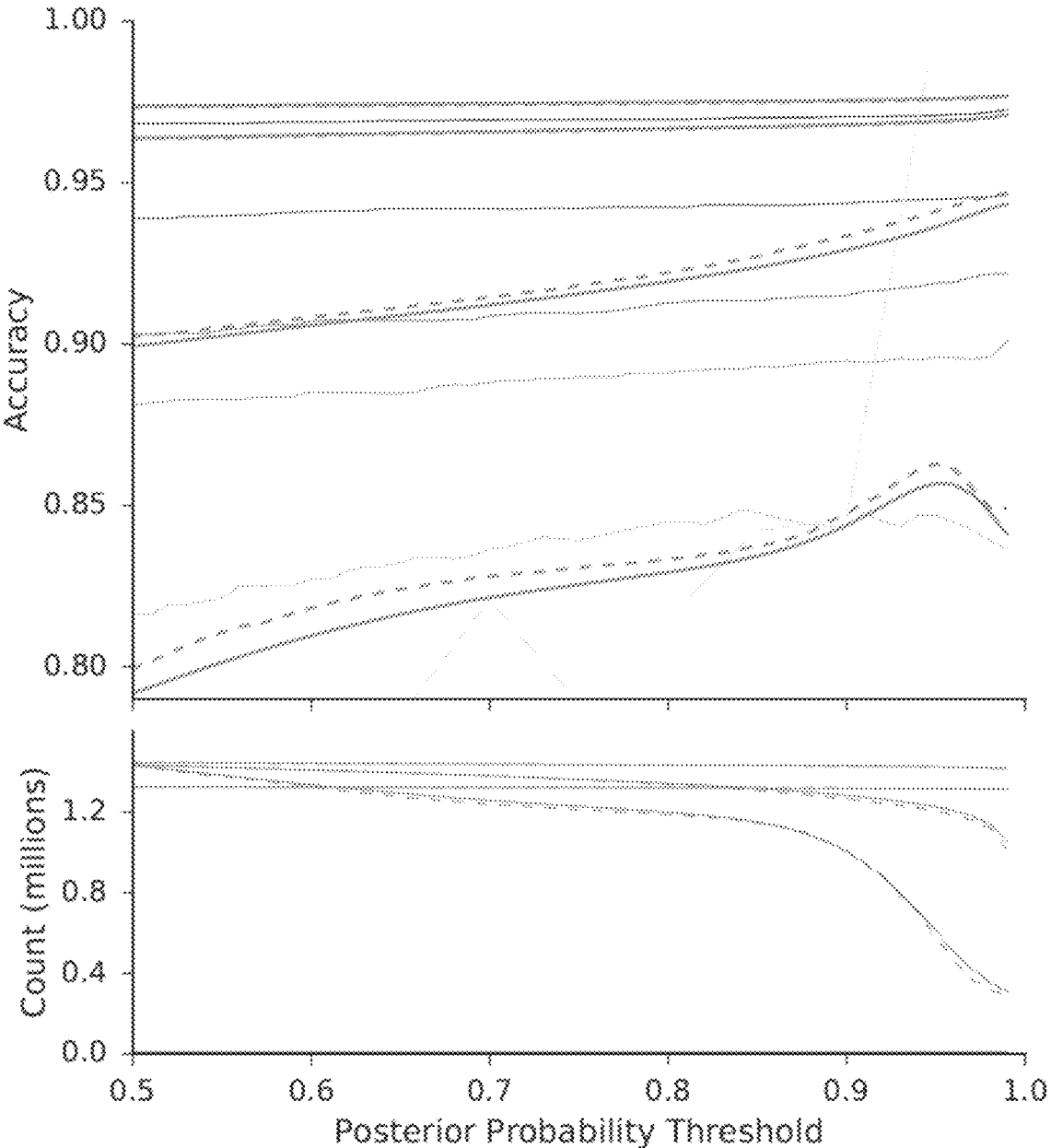
Figure 2C:
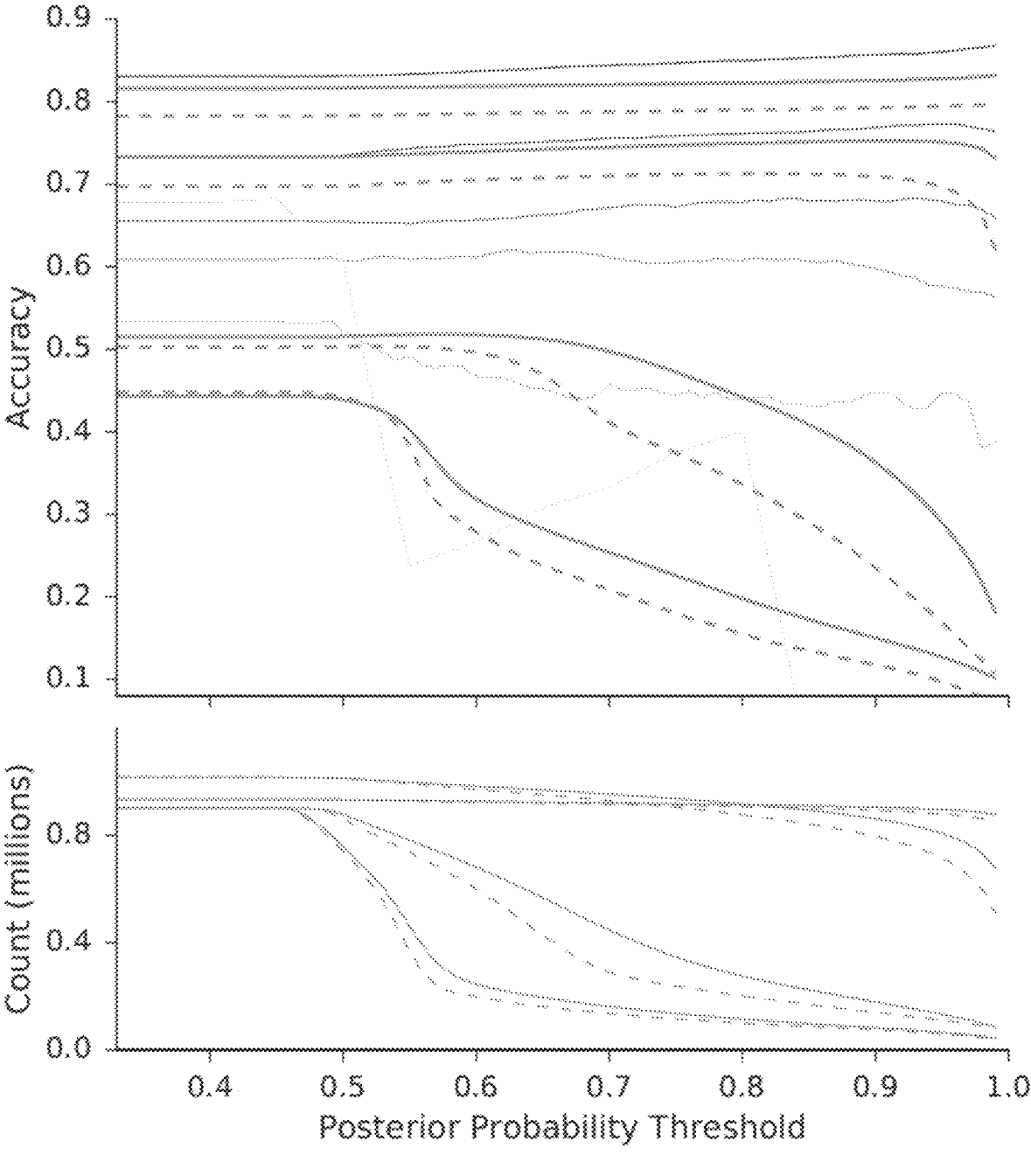

In order to test the accuracy with and without fragment sizes, the method was executed once with the total fetal fraction as a fixed parameter for each fragment, and again with a fetal fraction that depends on the fragment size. In all four families, the method showed satisfactory calibration and the addition of fragment size information resulted in increased accuracy. FIGS. 2A-C show the relationship between the accuracy and the posterior probabilities at families G1-G4, in SNPs in which only the mother is heterozygous (FIG. 2A), only the father is heterozygous (FIG. 2B), or both parents are heterozygous (FIG. 2C). Shown is the accuracy as a function of the threshold for maximum posterior probability, which indicates the level of certainty of the predictions. A calibrated model should show a smooth, ascending curve. Lower calibration was observed for the low-coverage cases (families G3-G4, FIGS. 2A-C, see color codes in FIG. 2D), but the use of the fragment sizes showed an improvement in calibration.

Nonivasive Prenatal Indel Calling

Figure 3A:
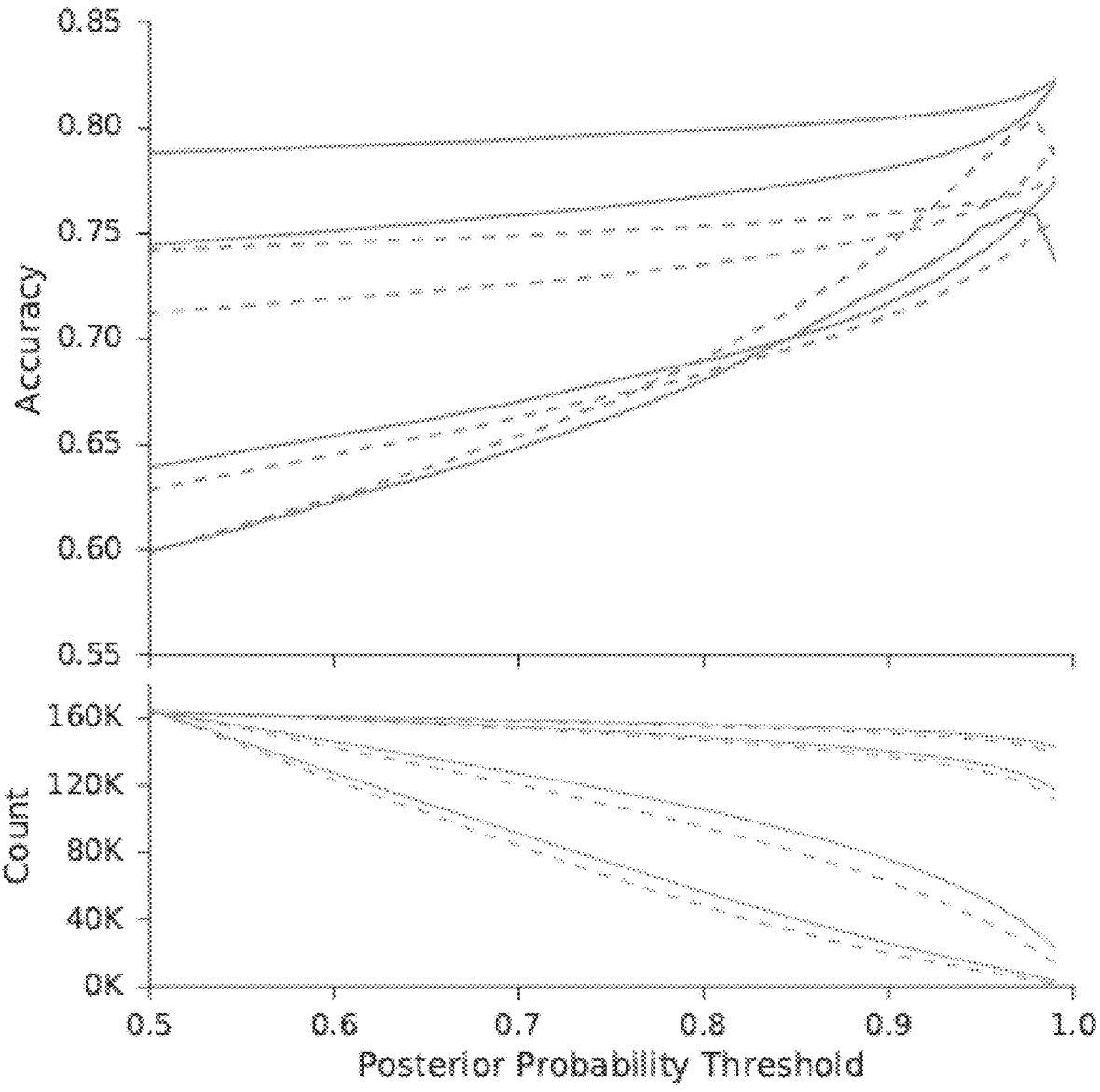
Figure 3B:
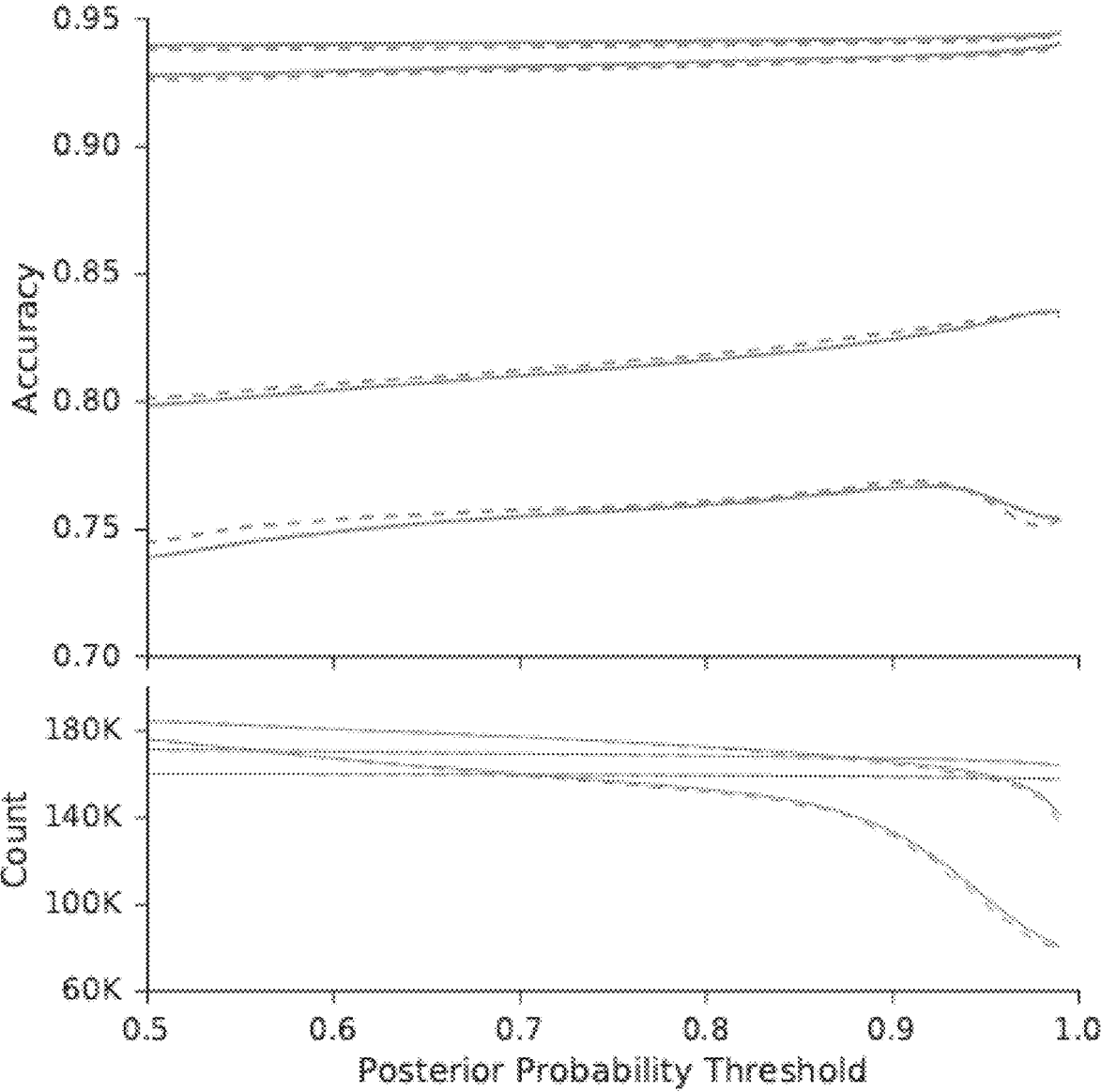
Figure 3C:
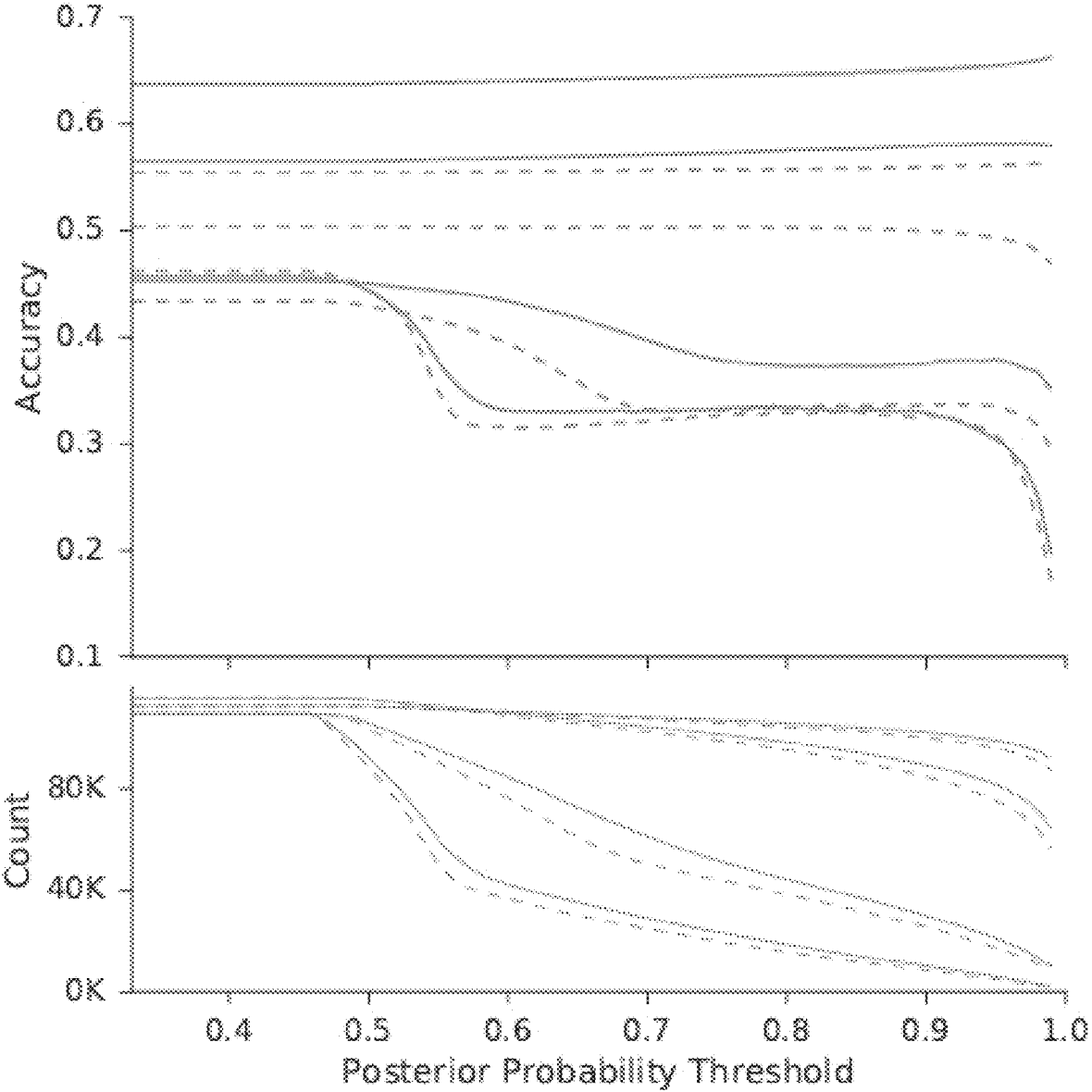
Figure 5A:
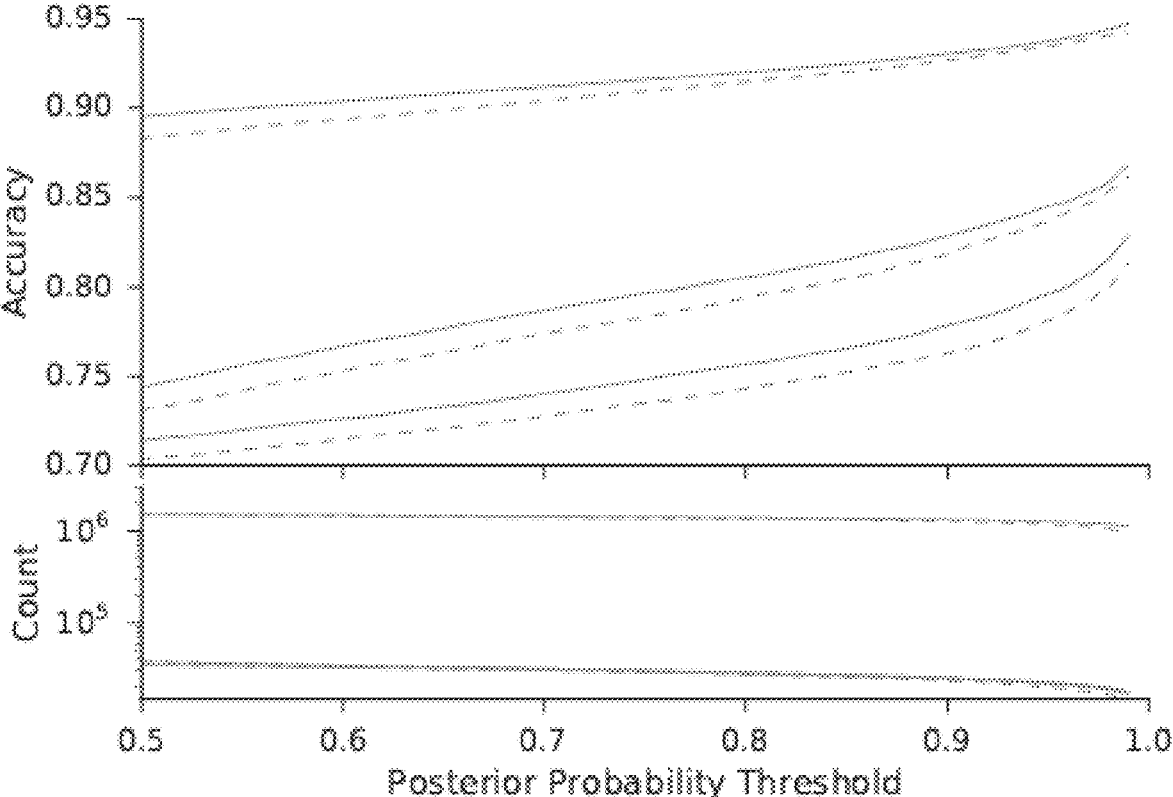
FIGS. 5A-G show performance over SNPs and indels in first-trimester cases, as obtained in experiments performed according to some embodiments of the present invention. Accuracies are presented for loci with posterior probabilities that are higher than the thresholds appearing in the x-axis. Findings of families sequenced in the experiments are presented for SNPs (FIGS. 5A-C) and indels (FIGS. 5D-F), according to the previously used loci categories. The total accuracy for each category is the accuracy at the leftmost point on the x-axis (0.5 in A-B and D-E, and 0.3 in C and F). The total counts from which the accuracy at each threshold was calculated are also presented.
Figure 5B:
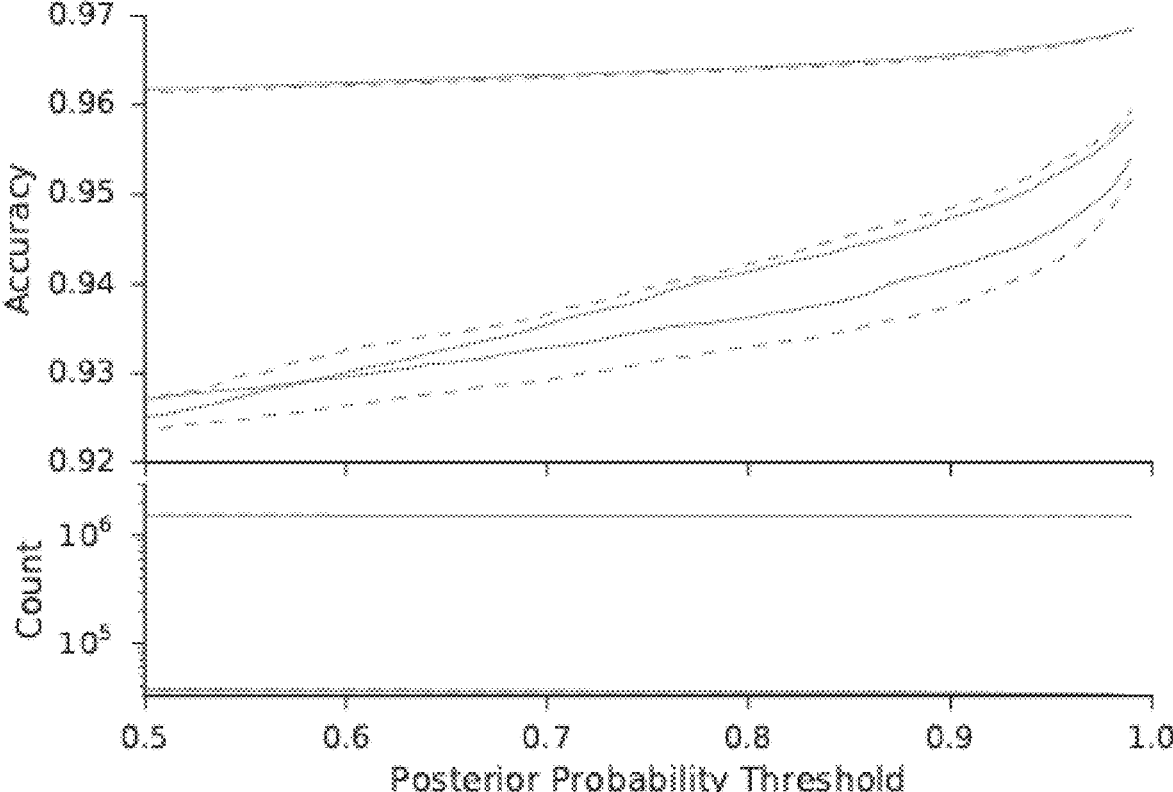
Figure 5C:
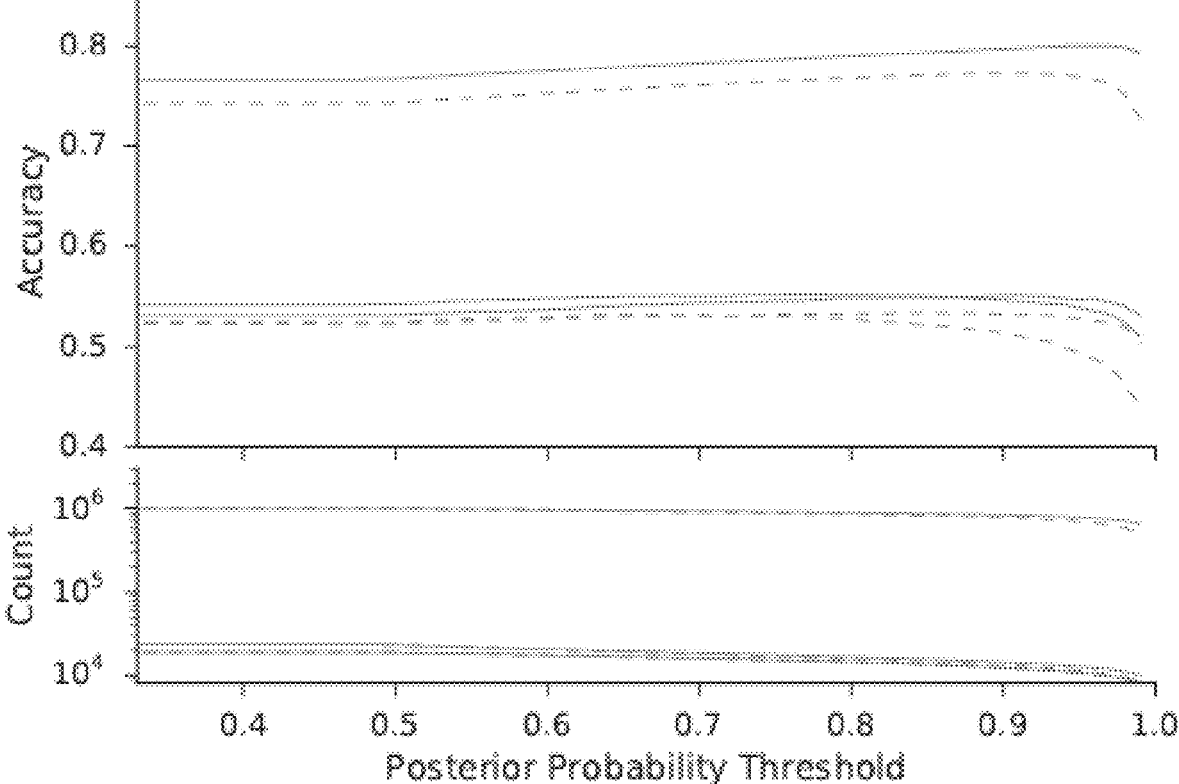
Figure 5D:
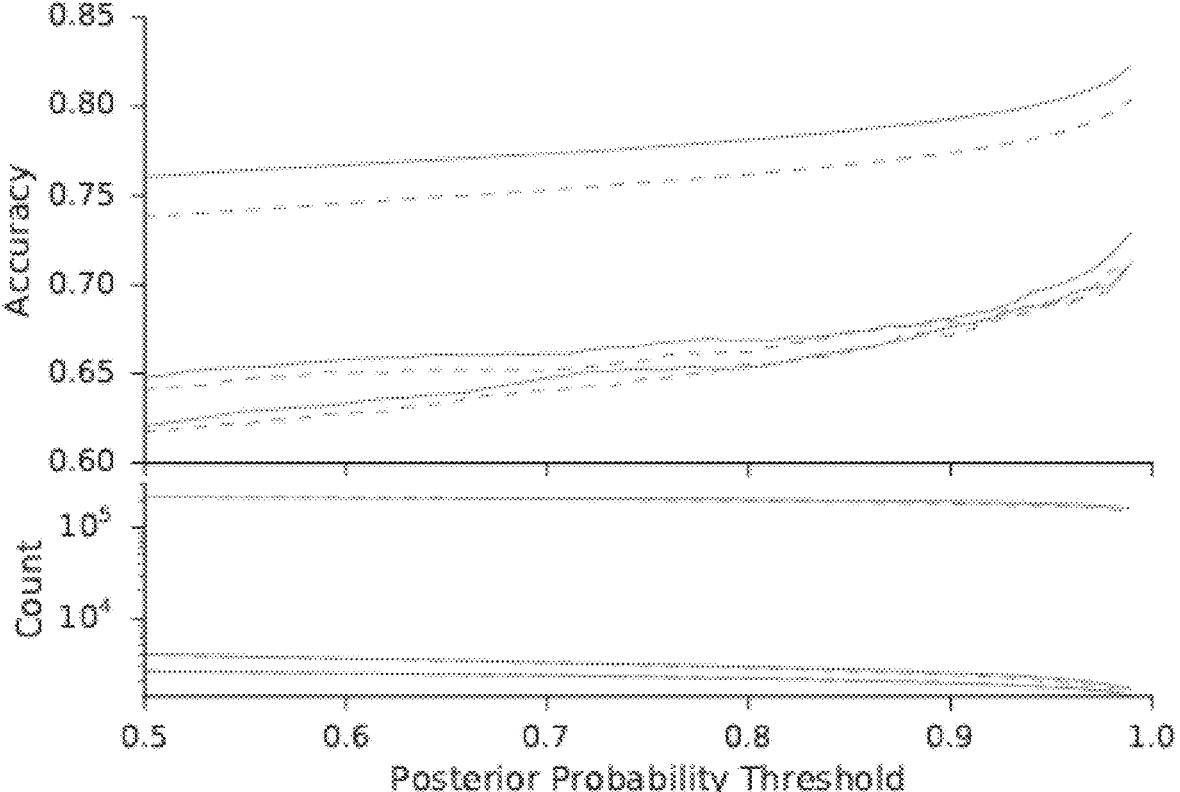
Figure 5E:
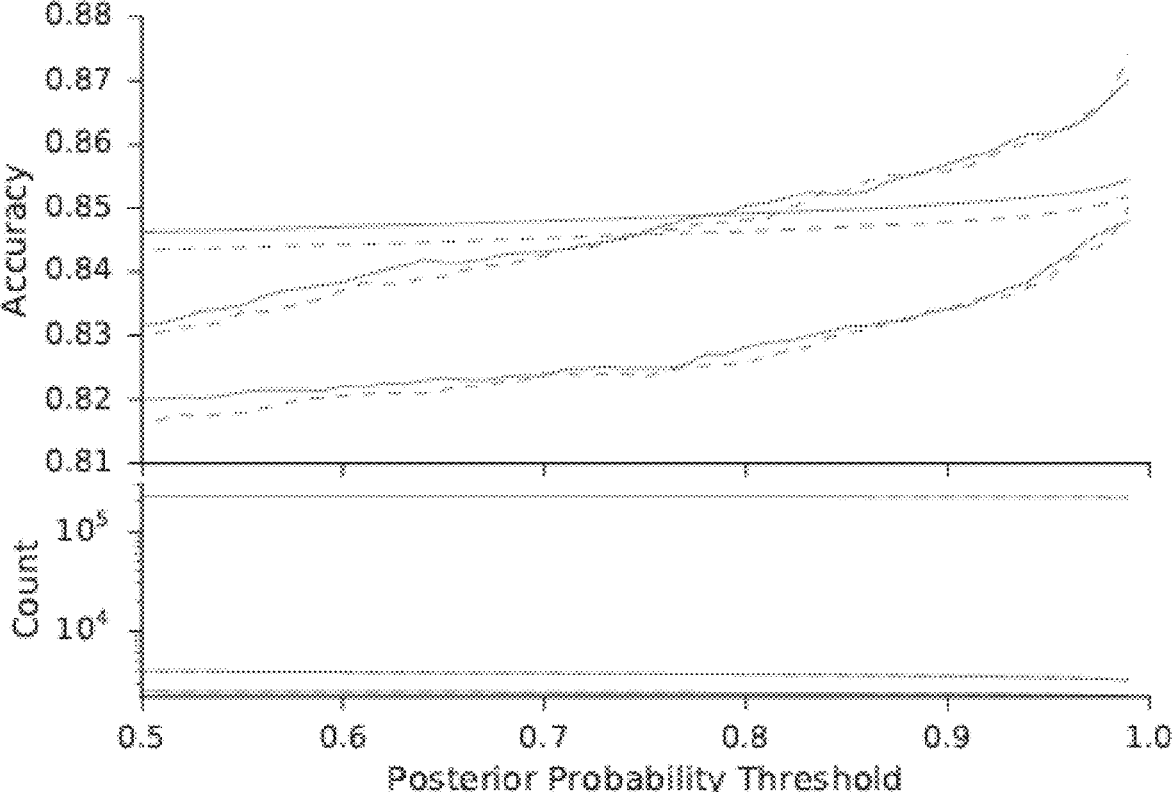
Figures 5F, 5G:
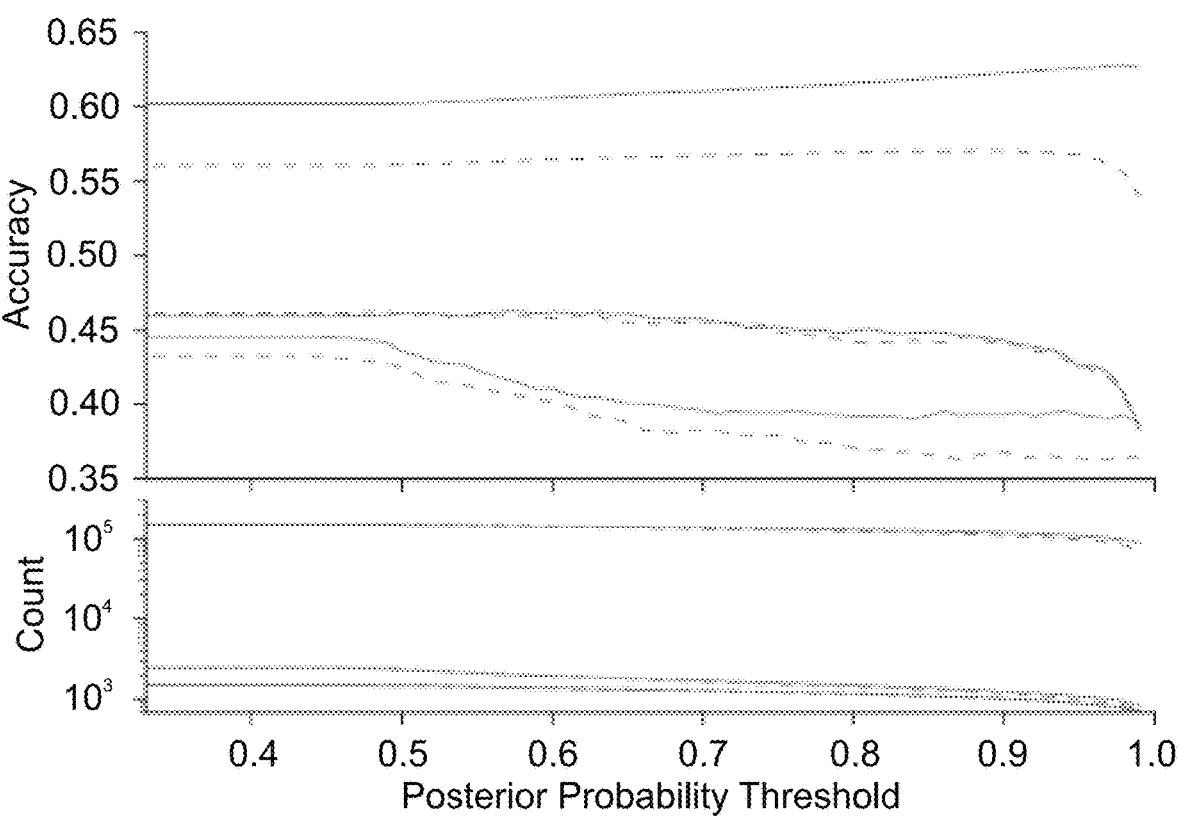
Figure 6A:
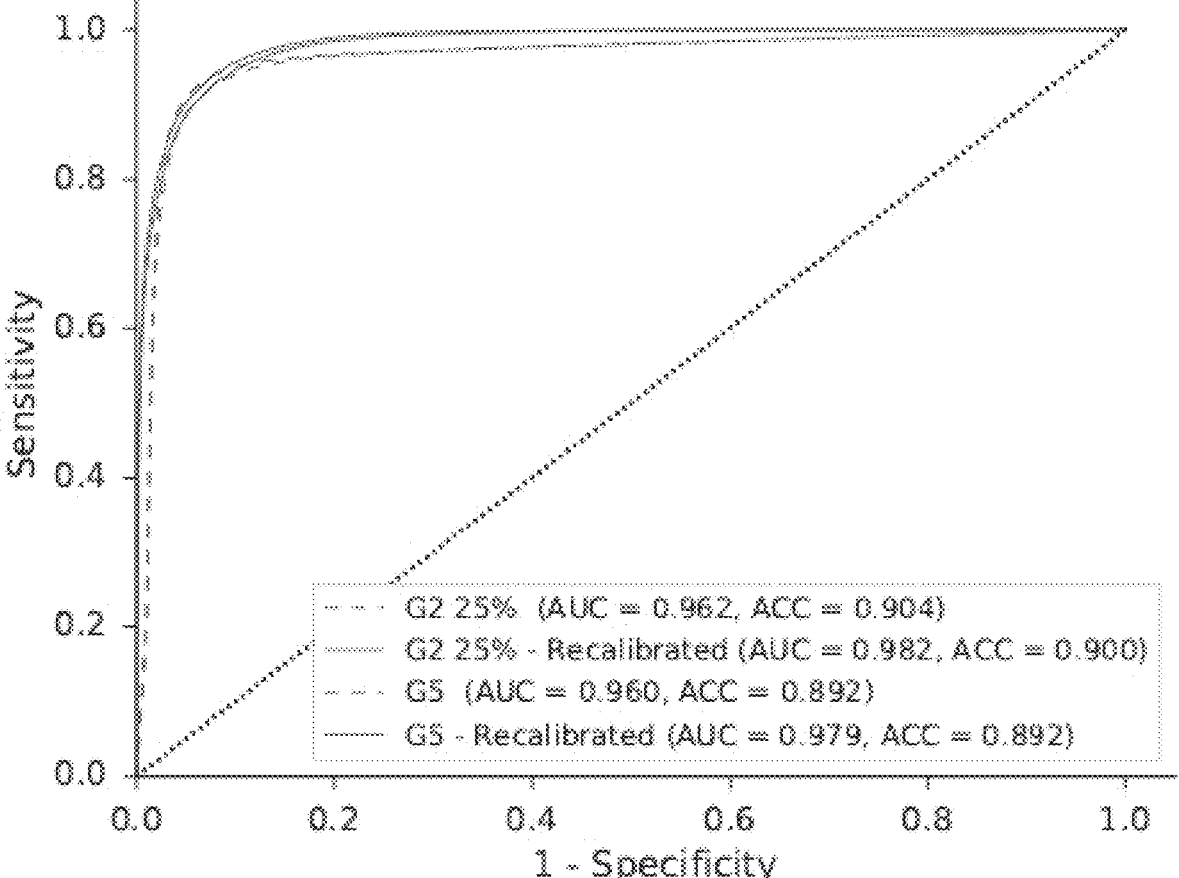
FIGS. 6A-F show receiver operating characteristic (ROC) curves of variant probability recalibration, as obtained in experiments performed according to some embodiments of the present invention. Presented are ROC curves of the two test sets, before and after a machine learning-based variant recalibration step, for the same previously used loci categories. For each curve, the micro-averaged area under the curve (AUC) and the total accuracy (ACC) are presented as well.
Figure 6B:
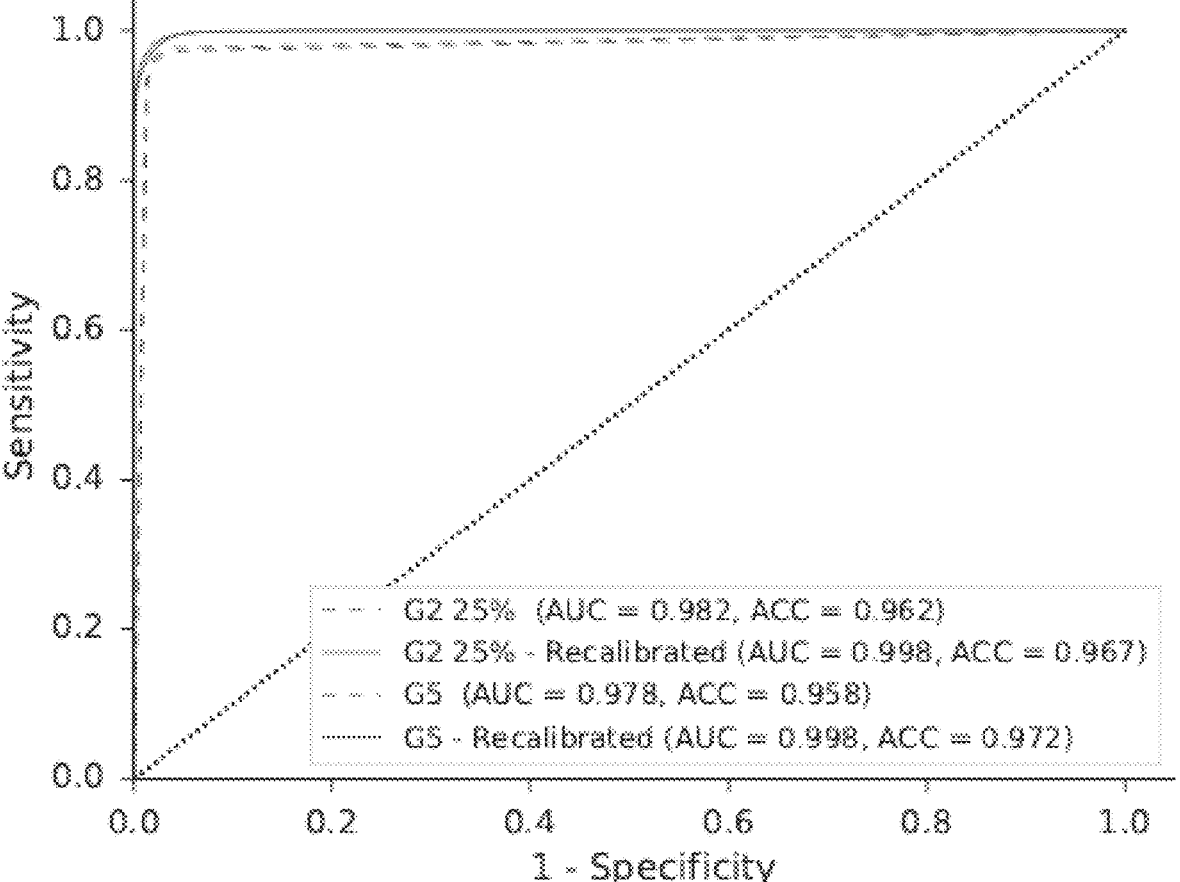
Figure 6C:
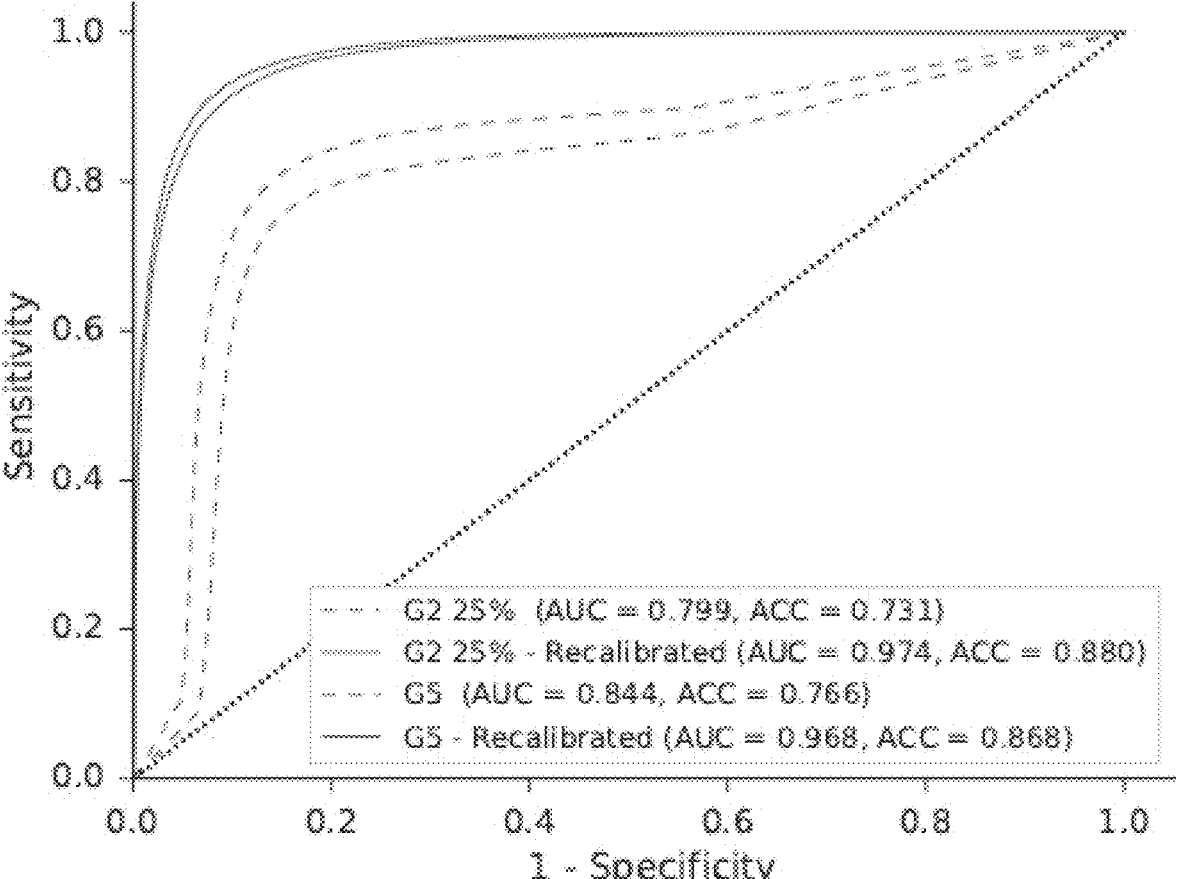
Figure 6D:
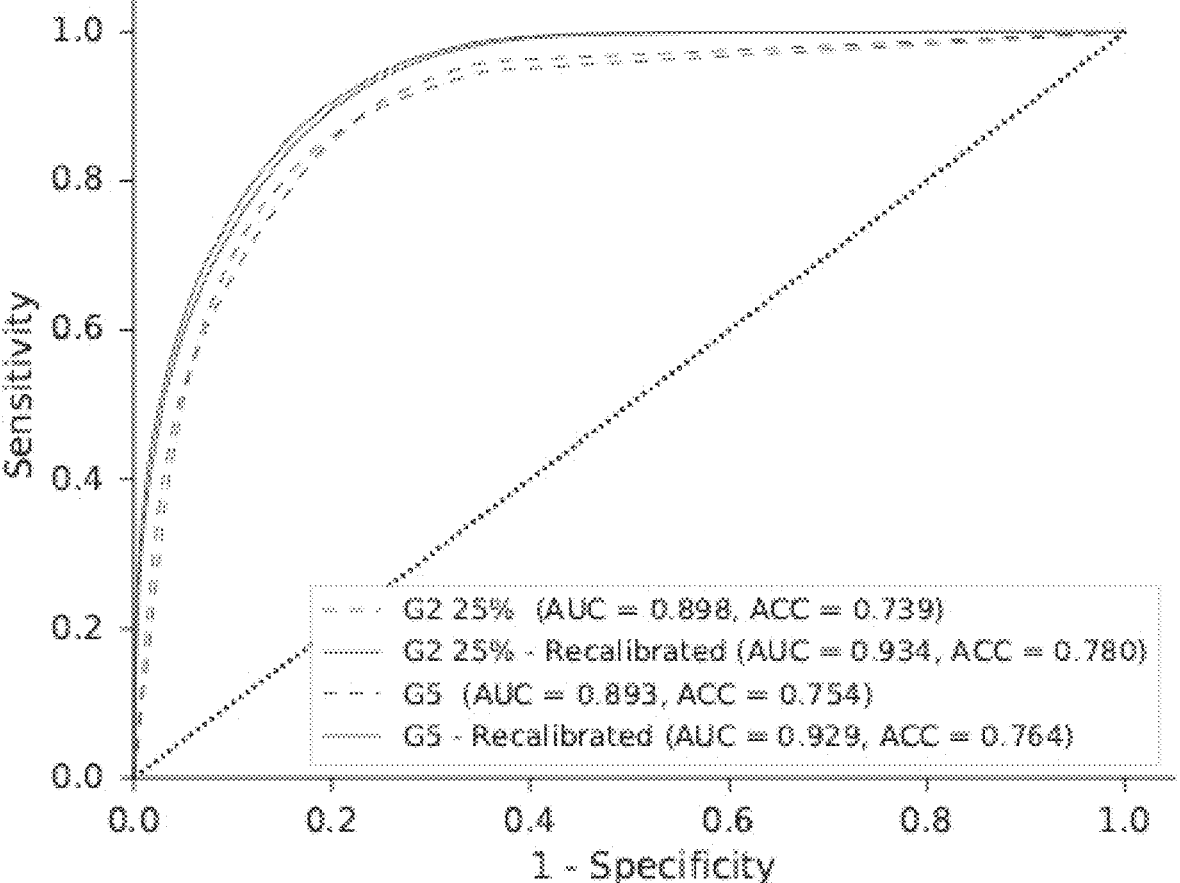
Figure 6E:
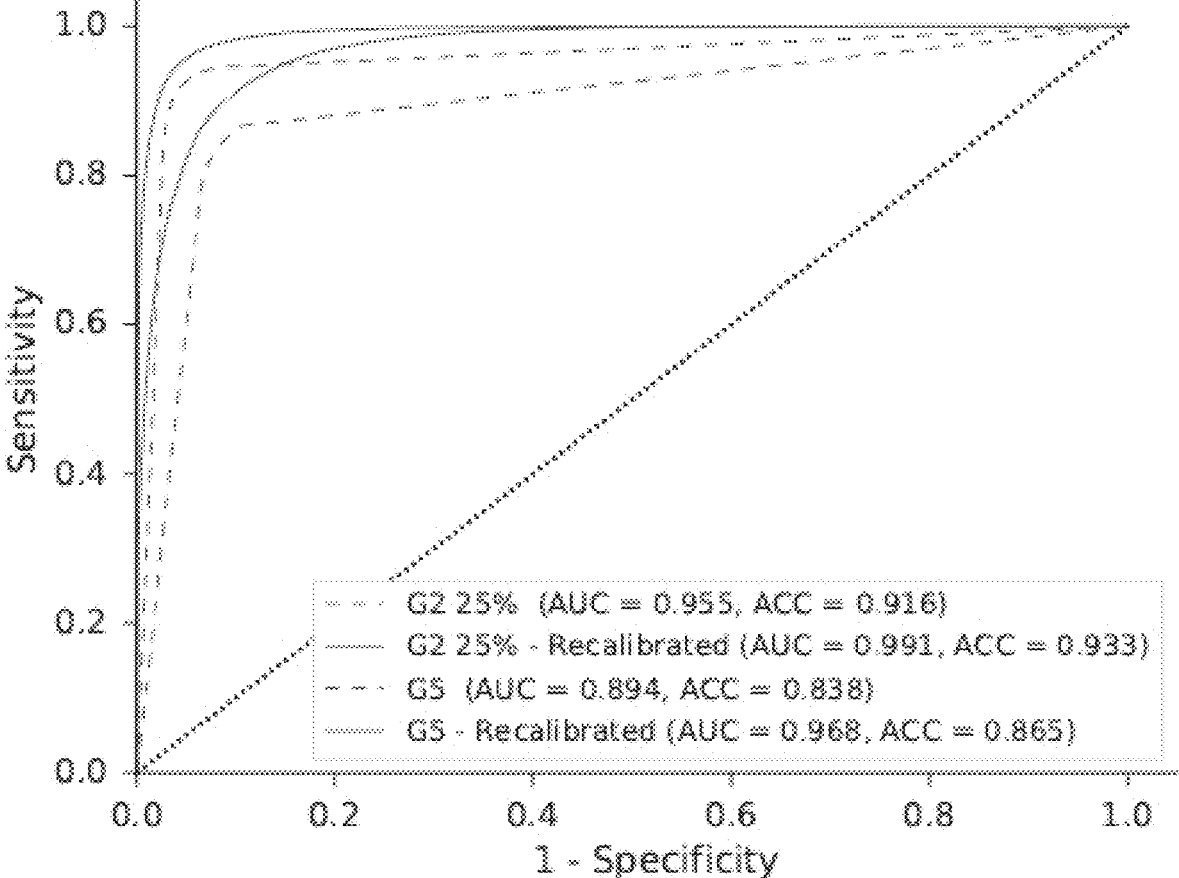
Figure 6F:
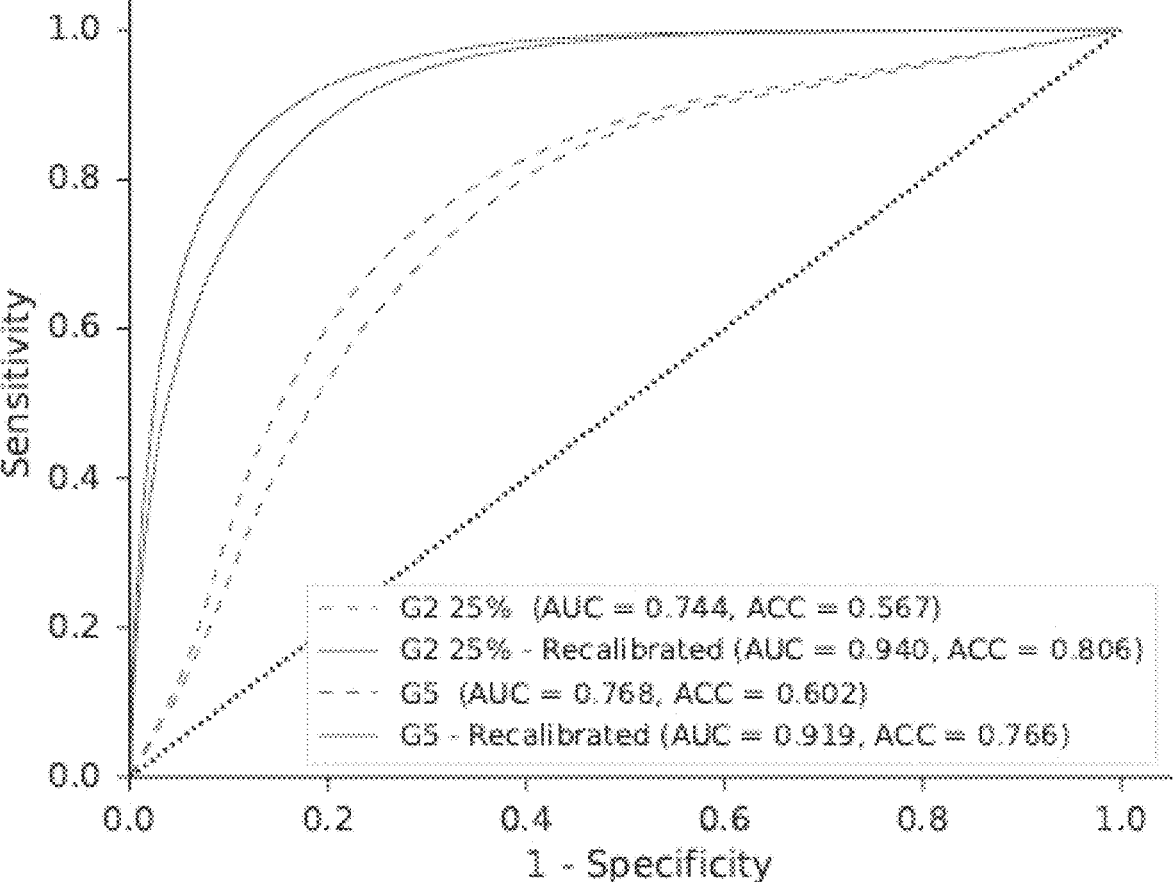

The method of the present embodiments was also utilized for parental indel calling. Again, the method was executed using the total fetal fraction as a fixed parameter, and then with a per-fragment size fetal fraction. FIGS. 3A-C (color codes in FIG. 3D) show calibration of the model at indel sites in which the mother is heterozygous. The accuracy as a function of the maximal posterior probability threshold of each site, is shown in indel sites that are either maternal-only heterozygous (paternal homozygous) (FIG. 3A) or paternal-only heterozygous (maternal homozygous) (FIG. 3B), or where both parents are heterozygous (FIG. 3C), for cases G1-G4. Method executions with a per-fragment size fetal fraction are shown in red, and method executions with a fixed fetal fraction are shown in blue.

With a fixed fetal fraction, the low-coverage families exhibited low accuracy and the calibration was inconsistent, whereas the high coverage families exhibited much higher accuracy and very good calibration. However, a considerable improvement in both accuracy and calibration was achieved when the fragment size information was used (FIGS. 3A-C). When the method was applied to sites where the father was heterozygous to an indel and the mother was homozygous to either the reference or the indel, the accuracy was higher compared with the maternal heterozygous indel sites (FIGS. 3A-C). With the size information, all families exhibited a better calibration, and the accuracy was improved in the high coverage family.

Analysis of Simulated Data

Figure 4A:
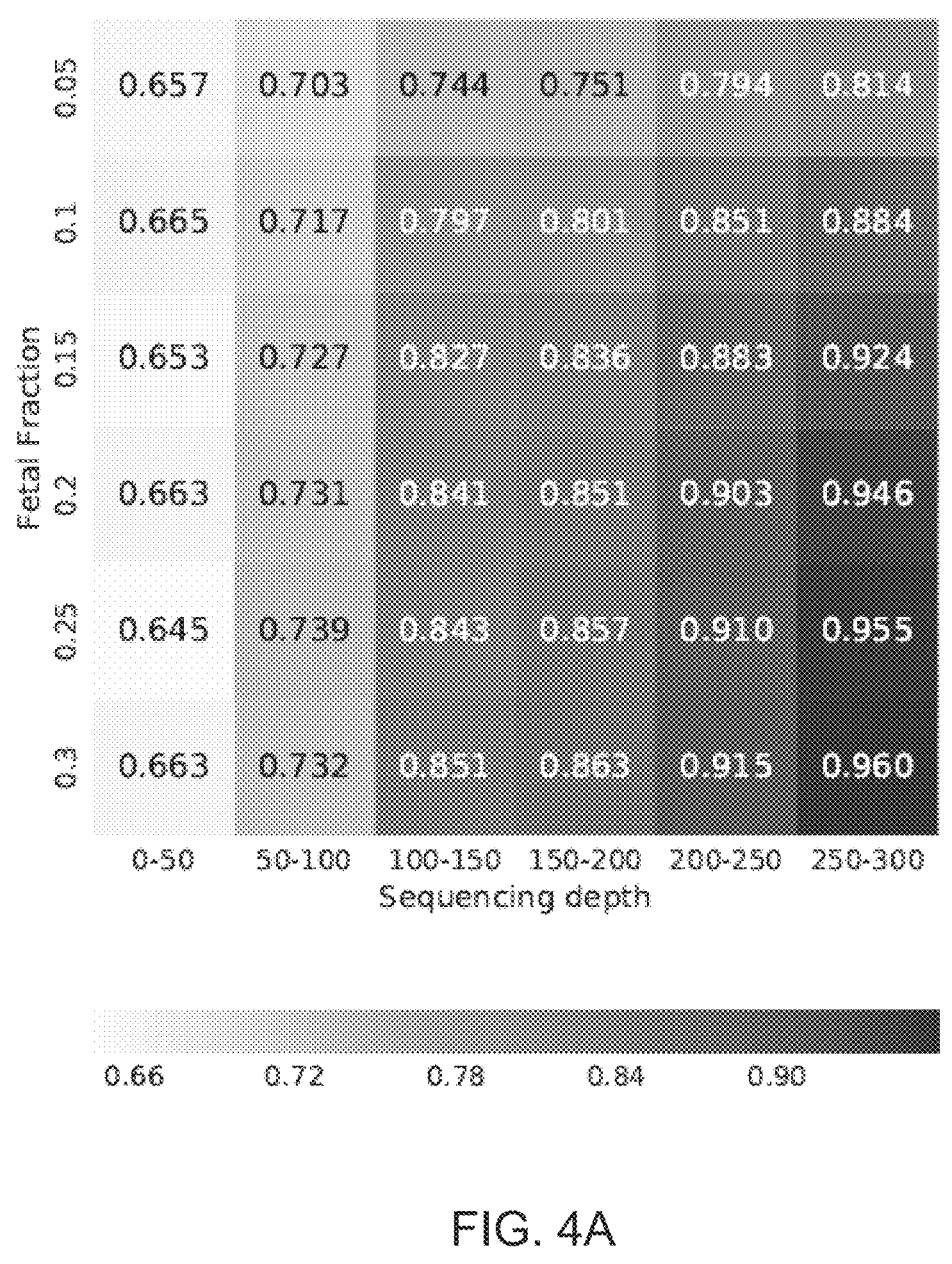
Figure 4B:
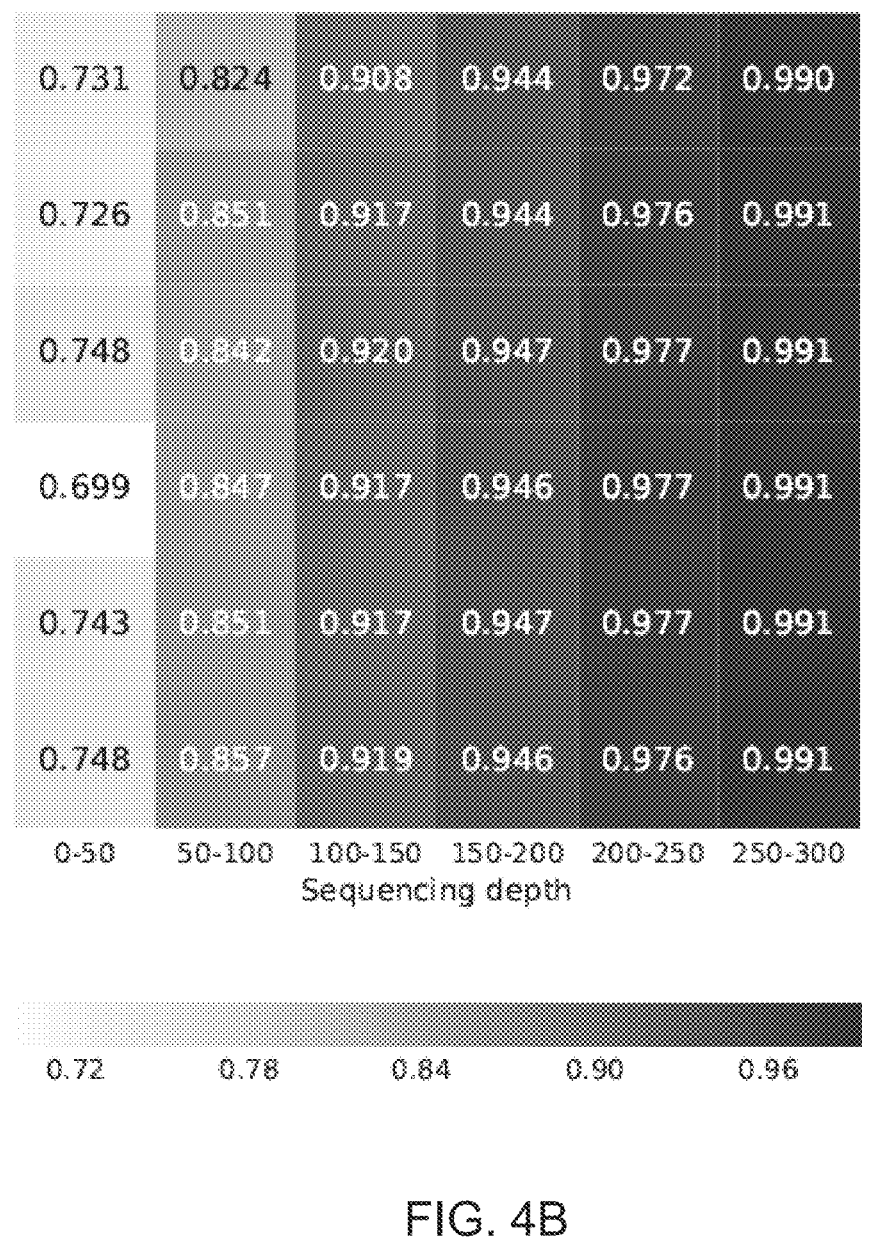

Robustness of the model of the present embodiments at low fetal fractions with high sequencing depth was examined using simulated data. Six triplicates of cfDNA samples with ranging values of fetal fraction were sub-sampled from family G1, while maintaining its sequencing depth. Each fetal fraction was further categorized based on sequencing depths. At the highest fetal fraction with the greatest depth, results showed high accuracy for each loci category: 96.0% for maternal-only heterozygous loci, 99.1% for paternal-only heterozygous loci and 91.1% for loci where both parents are heterozygous (FIGS. 4A-C). For fetal fraction values that are more common in the first trimester, i.e. 10-15%, the accuracy at the greatest sequencing depth was 88.4-92.4%, 99.1% and 82.8-87.1% for the same categories, respectively.

Analysis of Three First Trimester Cases Using Deep WES/WGS

Three families were sequenced (see Table 2, below) and their data were fed to the method of the present embodiments. In two cases, to achieve a deep coverage of the sequenced area, WES was used (about 2-3% of the genome). In the third case, deep-WGS was used. In family E1, the parents were carriers of a mutation that causes congenital chloride diarrhea (CCD), an autosomal recessive condition

TABLE 2

| Summary of sequenced samples | | | | |
| --- | --- | --- | --- | --- |
| Family | Individual | Sample | Sequenced Area | Depth of Coverage* |
| E1 | Mother | White blood cells | WES | 99 |
| | | Plasma (11 weeks) | WES | 735 |
| | Father | White blood cells | WES | 93 |
| | Offspring | Chorionic villus | WES | 97 |
| E2 | Mother | White blood cells | WGS | 36 |
| | | Plasma (11 weeks) | WES | 664 |
| | Father | White blood cells | WGS | 35 |
| | Offspring | Chorionic villus | WGS | 36 |
| G5 | Mother | White blood cells | WGS | 38 |
| | | Plasma (11 weeks) | WGS | 310 |
| | Father | White blood cells | WGS | 41 |
| | Offspring | Chorionic villus | WGS | 38 |

*Median, on target.

Similar as before, the method of the present embodiments was tested on SNPs and indels at sites where the mother is heterozygous. FIGS. 5A-F (see color codes in FIG. 5G) show calibration at SNP sites (FIGS. 5A-C) and indel sites (FIGS. 5D-F) for families E1, E2 and G5. Shown is the accuracy as a function of the maximal posterior probability threshold.

The calculated fetal fractions in the cfDNA sample of families E1, E2 and G5 were 15.8%, 12.8% and 18.5%, respectively. FIGS. 5A-F demonstrate that the method is well calibrated. Moreover, an improvement was achieved by the addition of fragment length information in all cases, even though the overall accuracy was limited. In family E2, an improvement in the calibration was gained as well. The algorithm was generally better calibrated for SNPs, although the results were somewhat lower in family E2, in which WGS was used for validating variants. For indels, the model had a very good calibration in the family E2. Family G5 showed the highest results in all categories of SNPs and indels.

Among the predicted SNPs, the fetal genotype of the mutation in SLC26A3 was successfully predicted. The prediction showed that the fetus is homozygous to the mutant allele, a result that matched the WES of the chorionic villus sampling (CVS). This was further validated using Sanger sequencing. The certainty of the prediction was higher when the information about fragment lengths was included. In the relevant site, the posterior probability was 61% with length information compared to 56% without it. As expected, the mutation was not detected in family E2.

Machine Learning-Based Variant Probability Recalibration

During this step, the results of each new processed sample are improved using a newly trained machine learning model. The features in this model were taken from the metadata that is available when genotyping the parents and the cfDNA (see Table A.1, in ANNEX 1). Family G1, in which the sequencing depth and fetal fraction were the highest, was selected as the first training set. Family G2 was randomly divided, and 75% of the variants were used as a validation set for the different models that were trained over G1. It was found that the Random Forest algorithm to have the best results. It was found that in maternal-only and double-heterozygous SNPs, the training should be performed using loci within the same category, e.g. a model that aims to improve the results of maternal-only heterozygous SNPs will only be trained over maternal-only heterozygous SNPs. In paternal-only heterozygous SNPs, all loci in which at least one parent is heterozygous should be used for training. Indels should be trained on both SNPs and Indels within the same category.

The chosen model was tested once over the remaining 25% of G2. The same model was trained again on families G1 and G2 combined and tested once over family G5, i.e. on a different data-set. The area under the receiver operating characteristic curve (AUC) was improved in all categories of loci, and accuracy was improved in almost all cases (FIGS. 6A-F). Prominent improvement was seen in loci where both parents were heterozygous, a condition that originally presented low accuracy. It was also found that following recalibration, the prediction probabilities better represented the actual accuracy, i.e. when the posterior probability is 0.9, the expected accuracy is ~0.9 as well. Furthermore, the accuracy at each prediction probability threshold improved considerably, suggesting that filtering of loci can indeed be performed using recalibration rather than setting stringent thresholds for specific features. At the threshold of 0.7, for instance, the accuracy in family G5 is improved to 98.3-99.8% over SNPs, from a total of 722.630 maternal-only heterozygous loci, 1,358,503 paternal-only heterozygous loci, and 358,114 double-heterozygous loci. Indel prediction accuracy is improved to 94.3-97.1%, from 42,726 maternal-only heterozygous loci, 142,577 paternal-only heterozygous loci, and 20,388 double-heterozygous loci. It was also found that Hoobari-derived features, such as the prior and posterior probabilities, the likelihood and the predicted genotype, have the greatest importance, followed by features related to the allelic balance in the cfDNA.

Figure 7A:
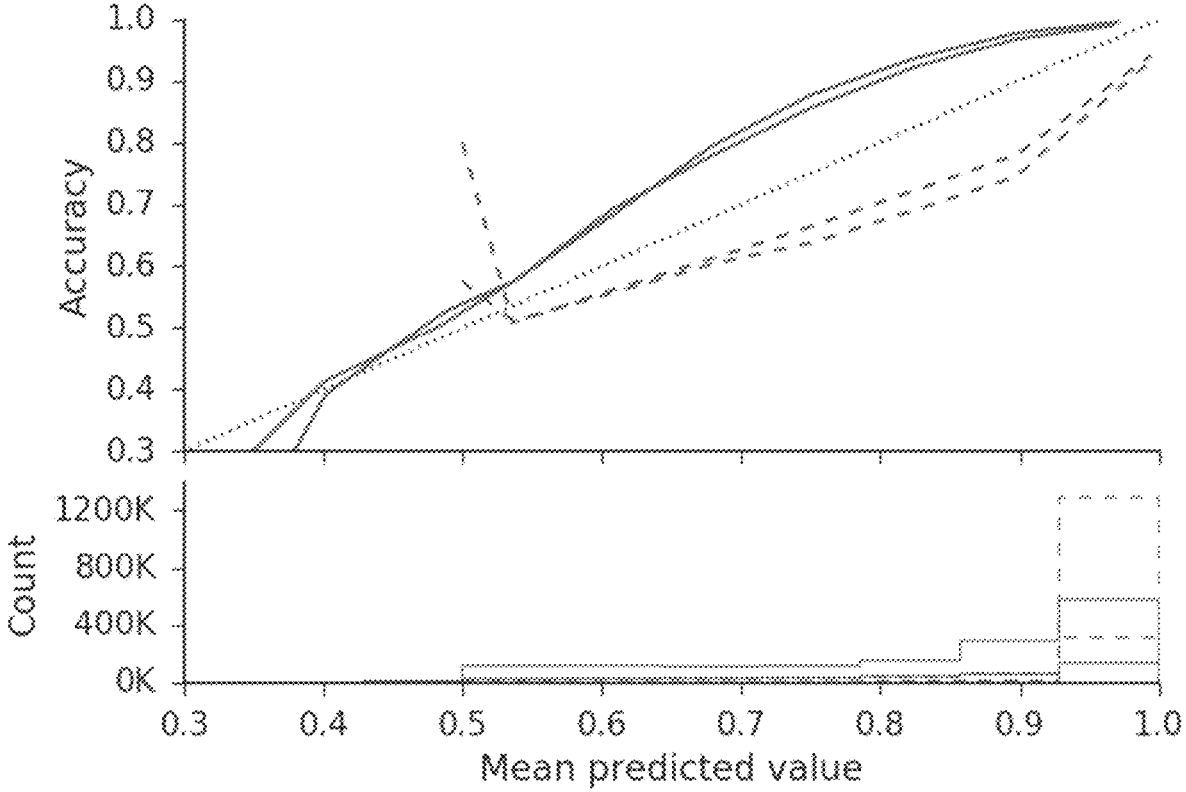
FIGS. 7A-G show calibration of the accuracy, as obtained in experiments performed according to some embodiments of the present invention. Shown is the accuracy as a function of the prediction probability, before and after variant recalibration. The "perfectly calibrated" line represents a situation in which the probability assigned to a prediction perfectly describes the probability of being correct (in terms of accuracy). Also presented are marginal distribution of loci in each bin.
Figure 7B:
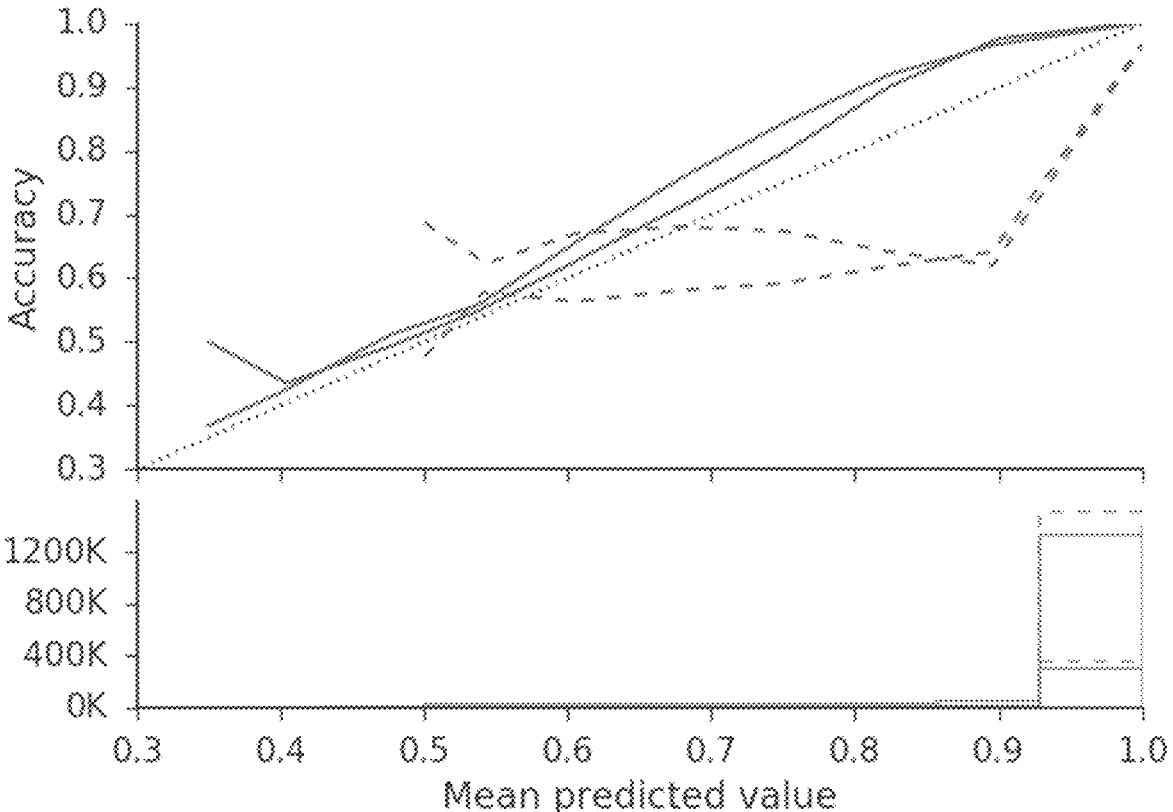
Figure 7C:
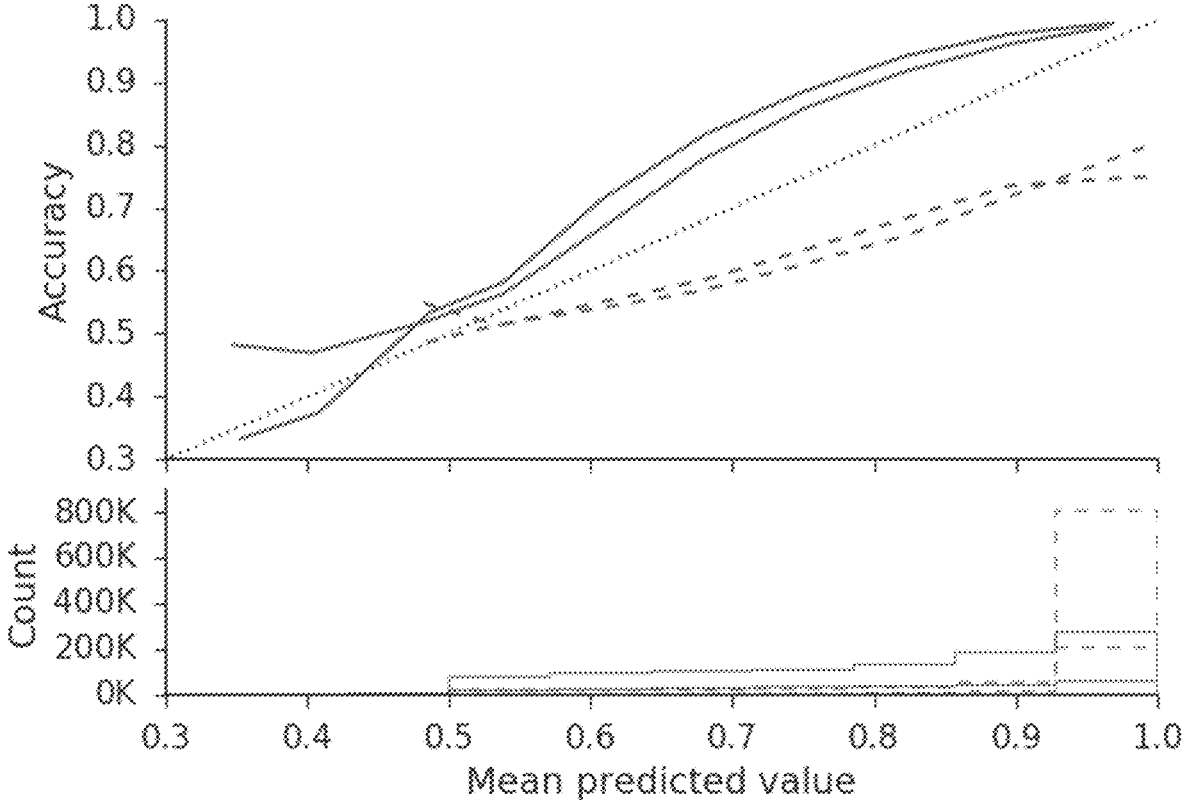
Figure 7D:
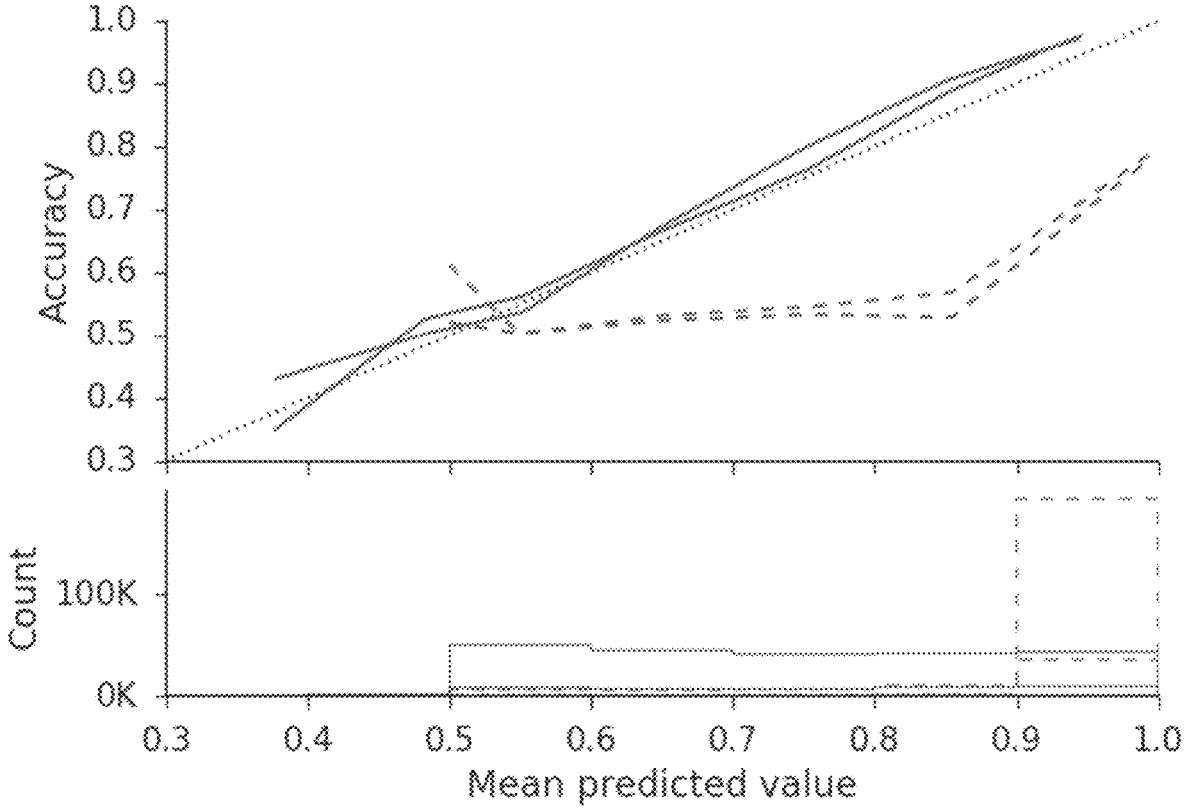
Figure 7E:
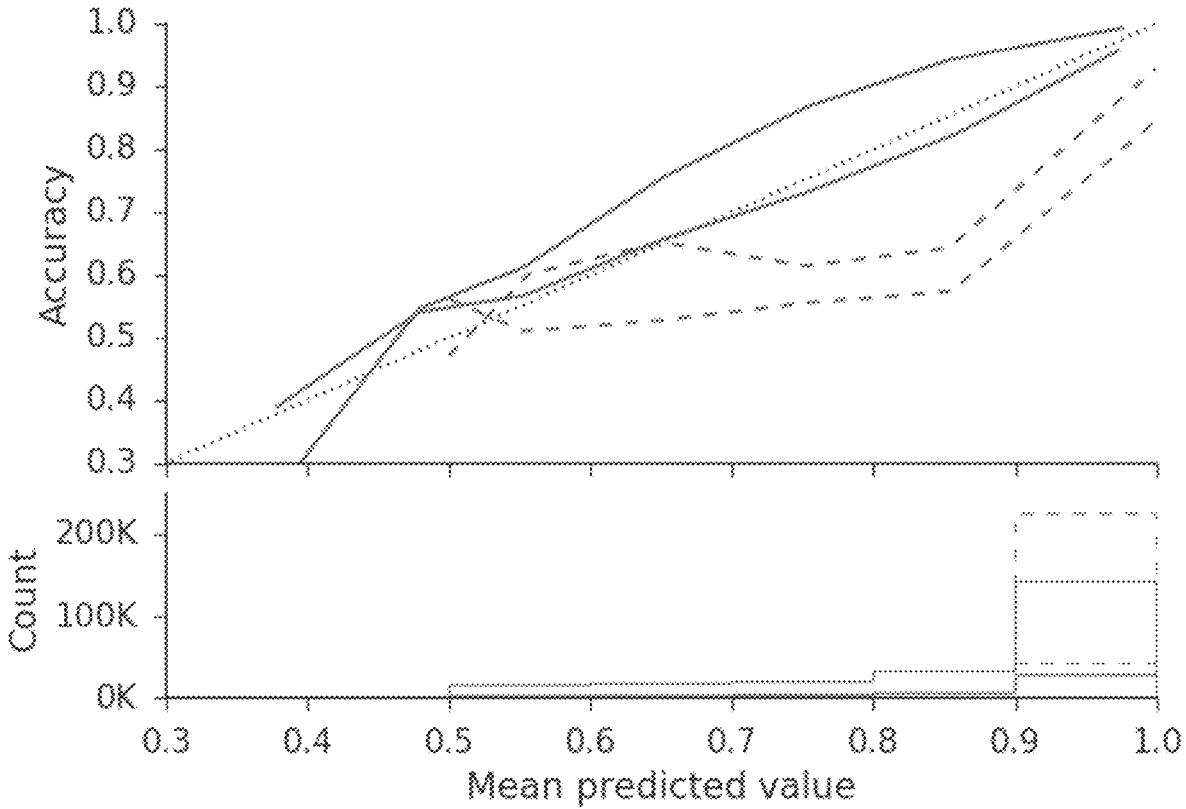
Figures 7F, 7G:
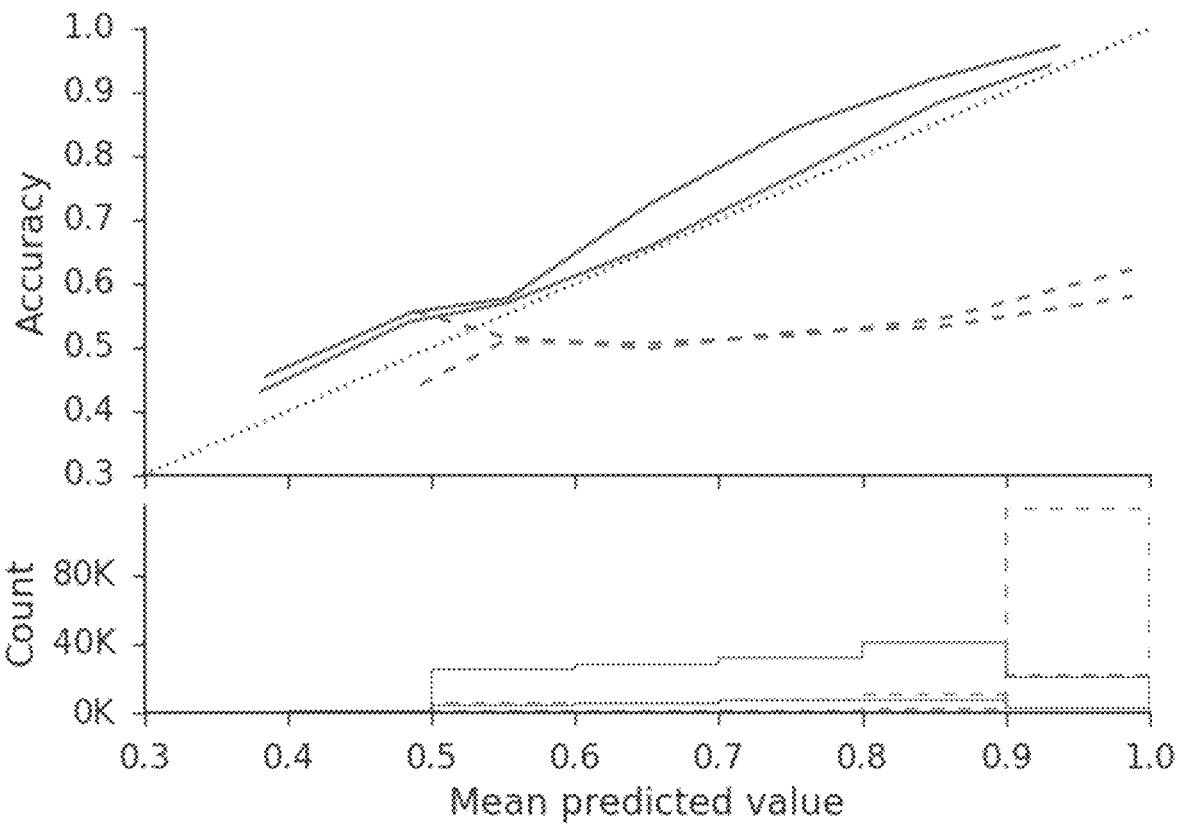

FIGS. 7A-F show calibration of the model's accuracy (color codes in FIG. 7G).

Shown is the accuracy as a function of the prediction probability, before and after variant recalibration. The "perfectly calibrated" line represents a situation in which the probability assigned to a prediction perfectly describes the probability of being correct (in terms of accuracy). Presented in the lower pane of each figure are is marginal distribution of loci in each bin. FIG. 7A corresponds to maternal-only heterozygous SNPs. FIG. 7B corresponds to paternal-only heterozygous SNPs, FIG. 7C corresponds to both-parents heterozygous SNPs, FIG. 7D corresponds to maternal-only heterozygous indels, FIG. 7E corresponds to paternal-only heterozygous indels, and FIG. 7F corresponds to both-parents heterozygous indels.

Figure 8A:
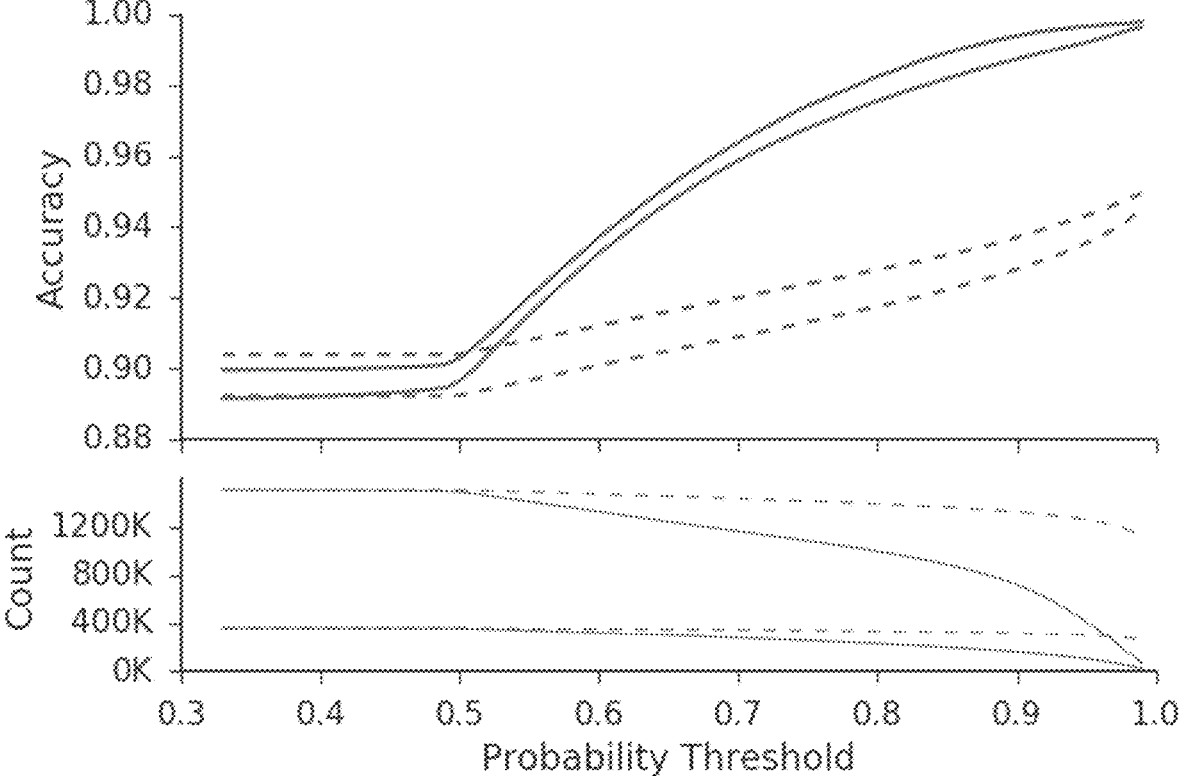
FIGS. 8A-G demonstrate the ability to perform machine learning-based variant recalibration for the filtering of variants. Accuracies are presented for loci with a posterior probabilities that are higher than the thresholds appearing in the x-axis. Findings are presented before and after variant recalibration. The total accuracy for each category is the accuracy at the leftmost point on the x-axis. The total counts from which the accuracy at each threshold was calculated are also presented.
Figure 8B:
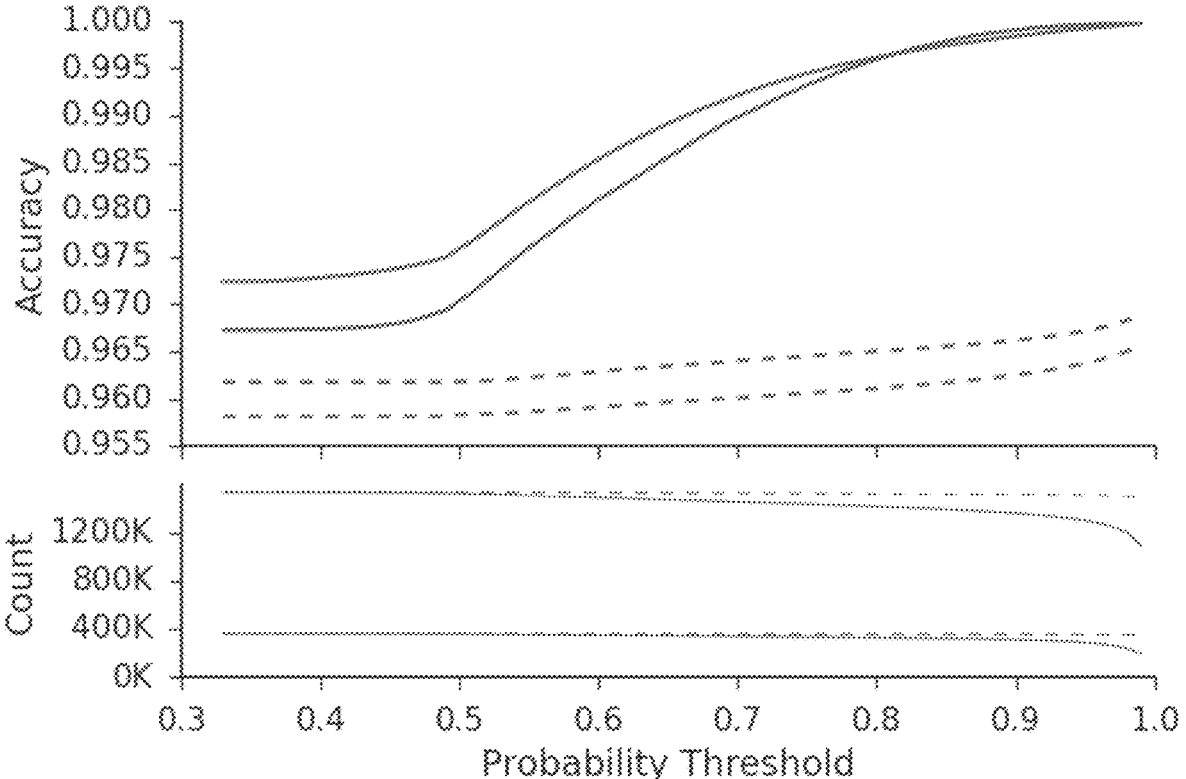
Figure 8C:
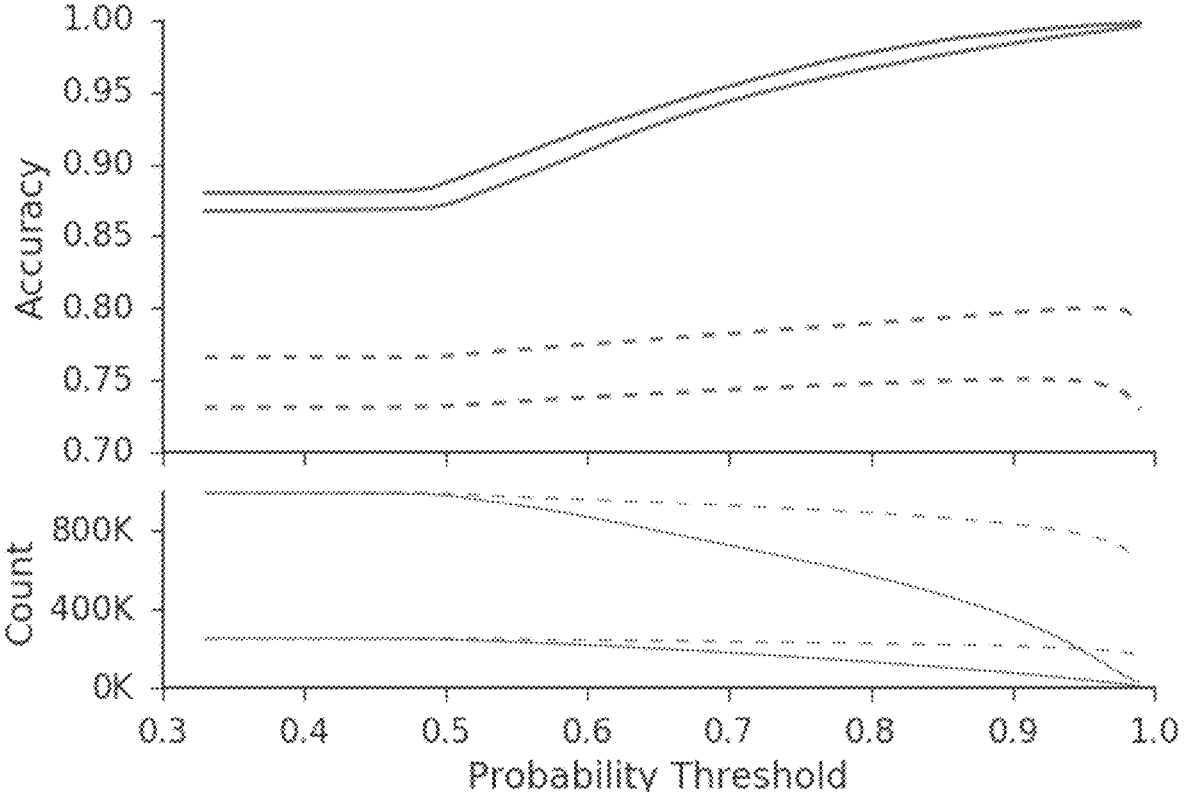
Figure 8D:
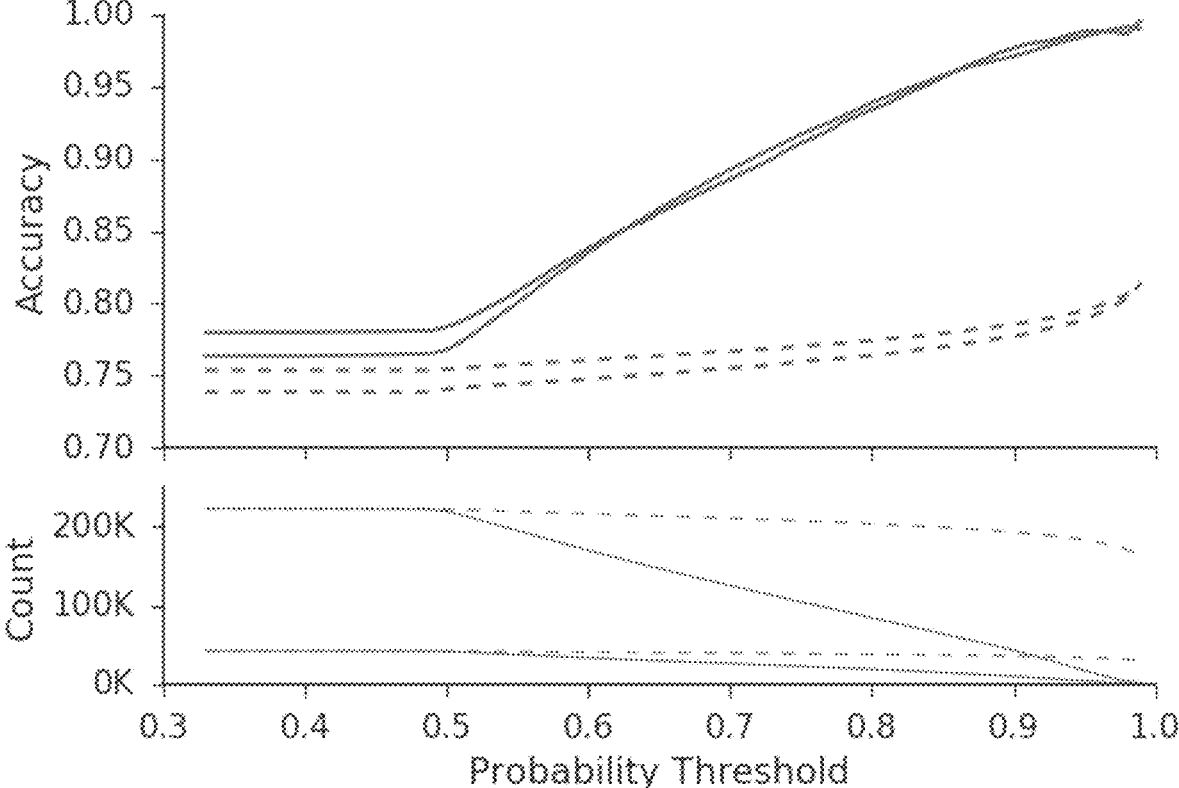
Figure 8E:
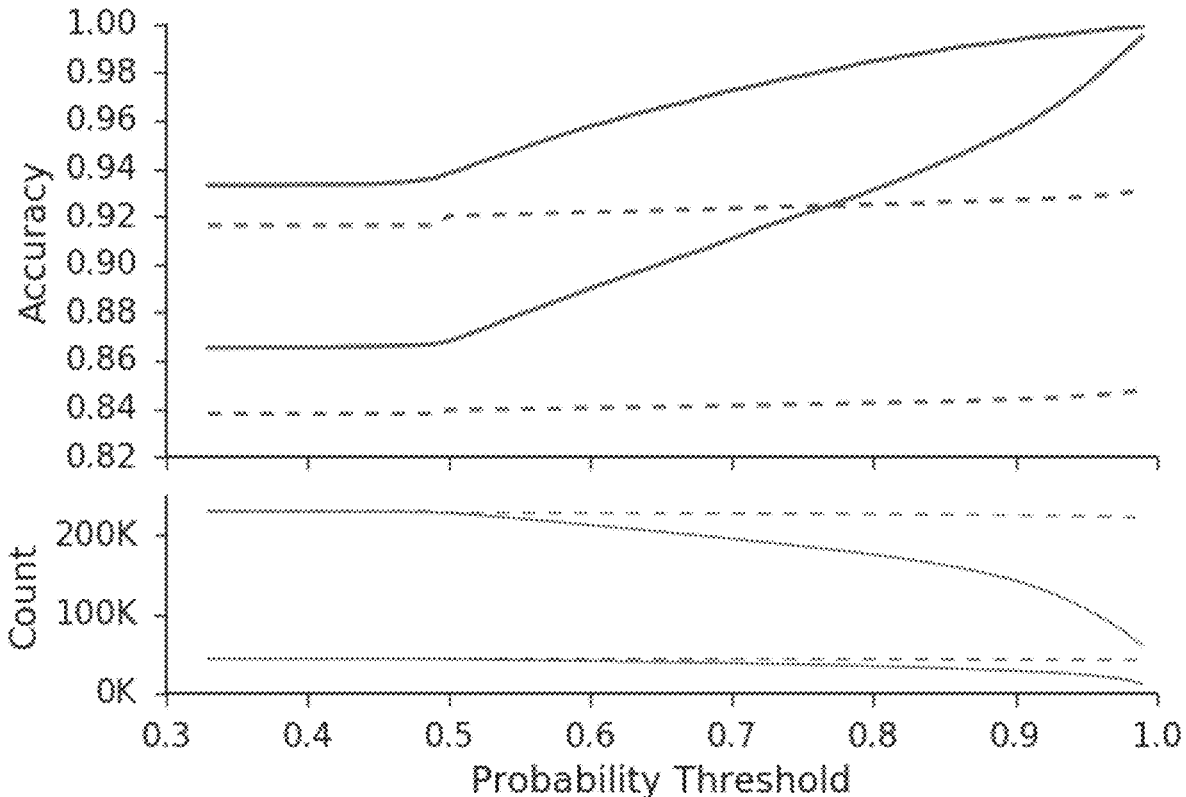
Figures 8F, 8G:
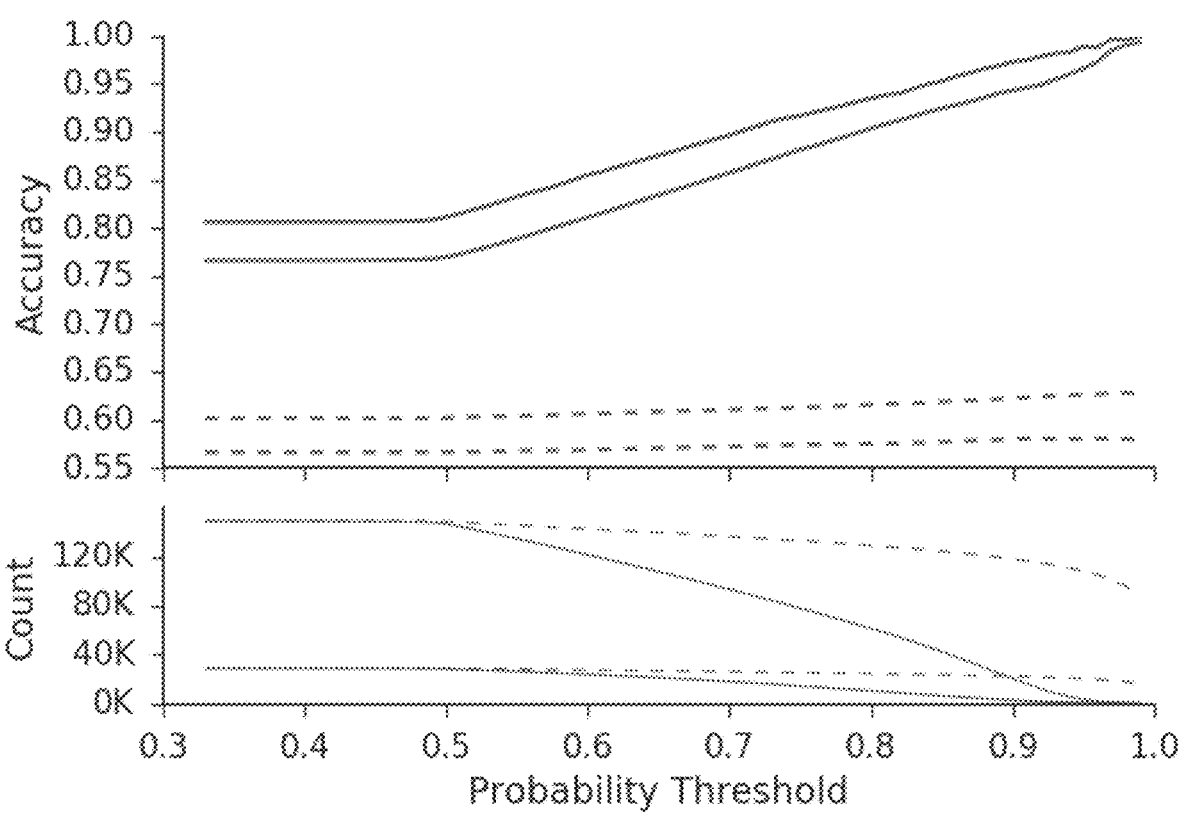
Figure 9A:
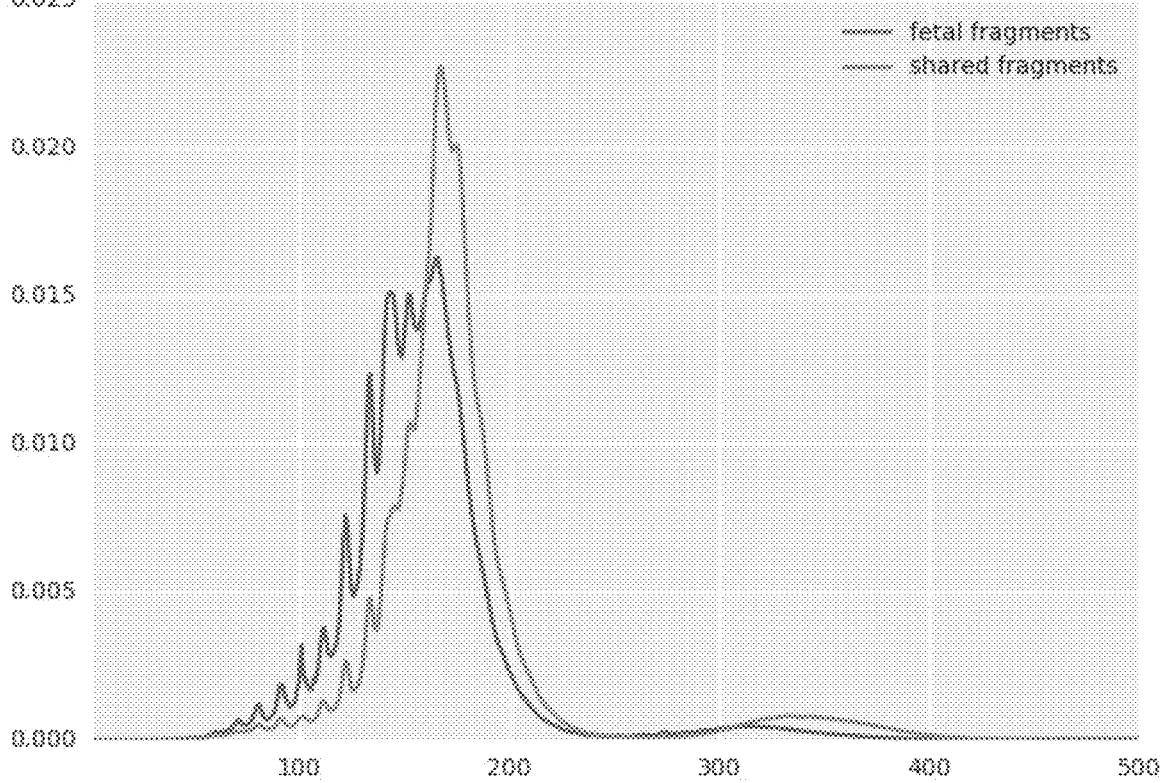
FIGS. 9A-G show cell-free DNA fragment length distributions as obtained in experiments performed according to some embodiments of the present invention. Presented are fetal (blue) and maternal (green) fragment length distributions for families included in these experiments.
Figure 9B:
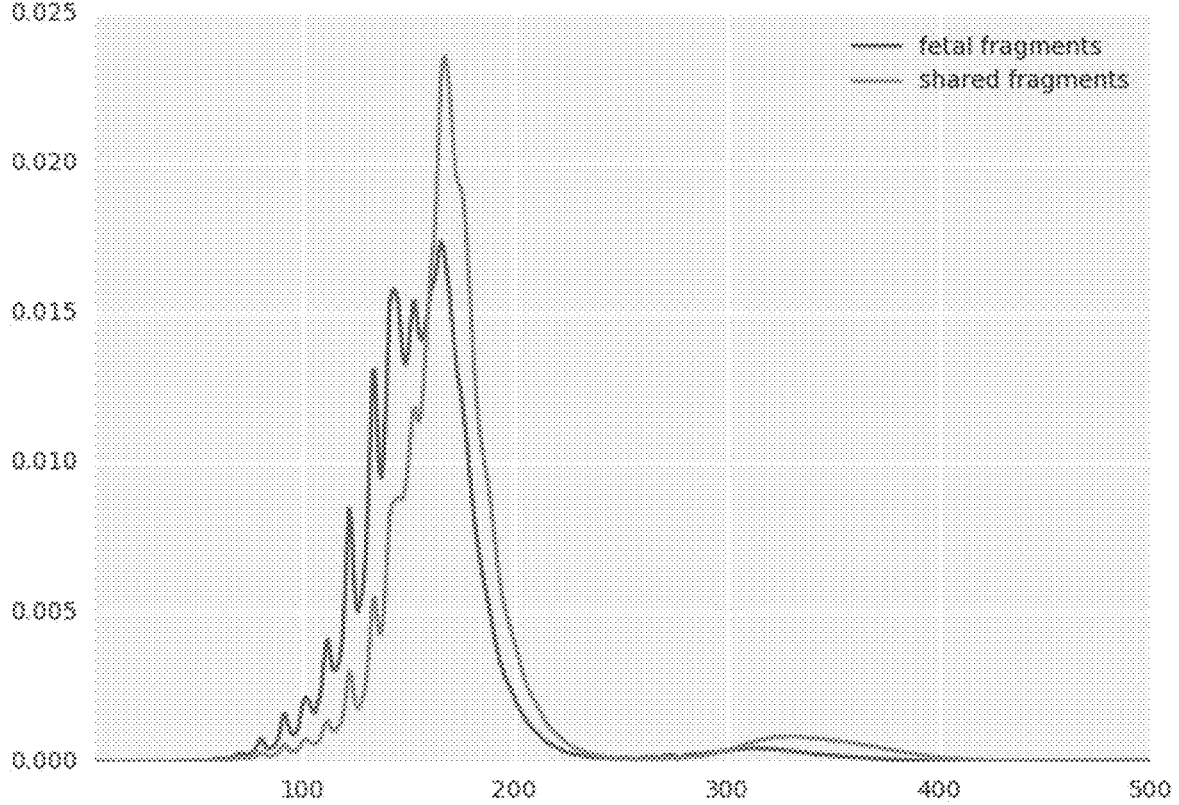
Figure 9C:
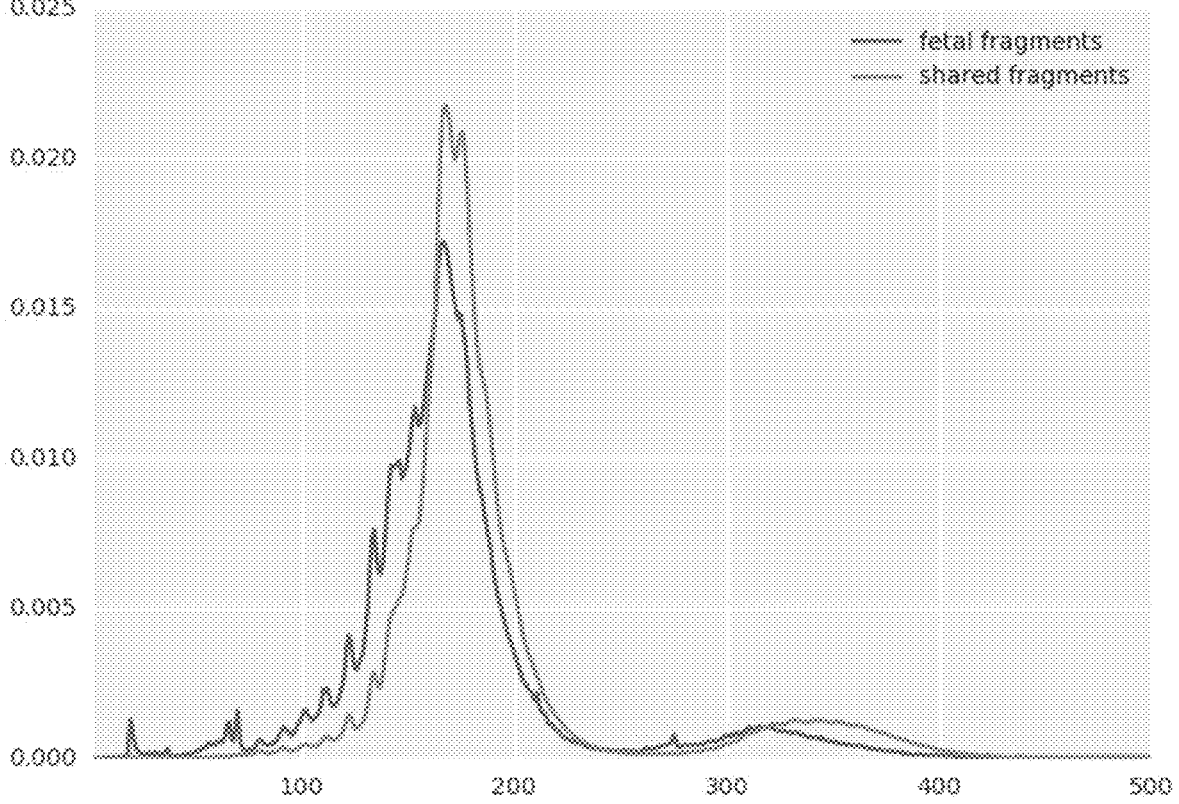
Figure 9D:
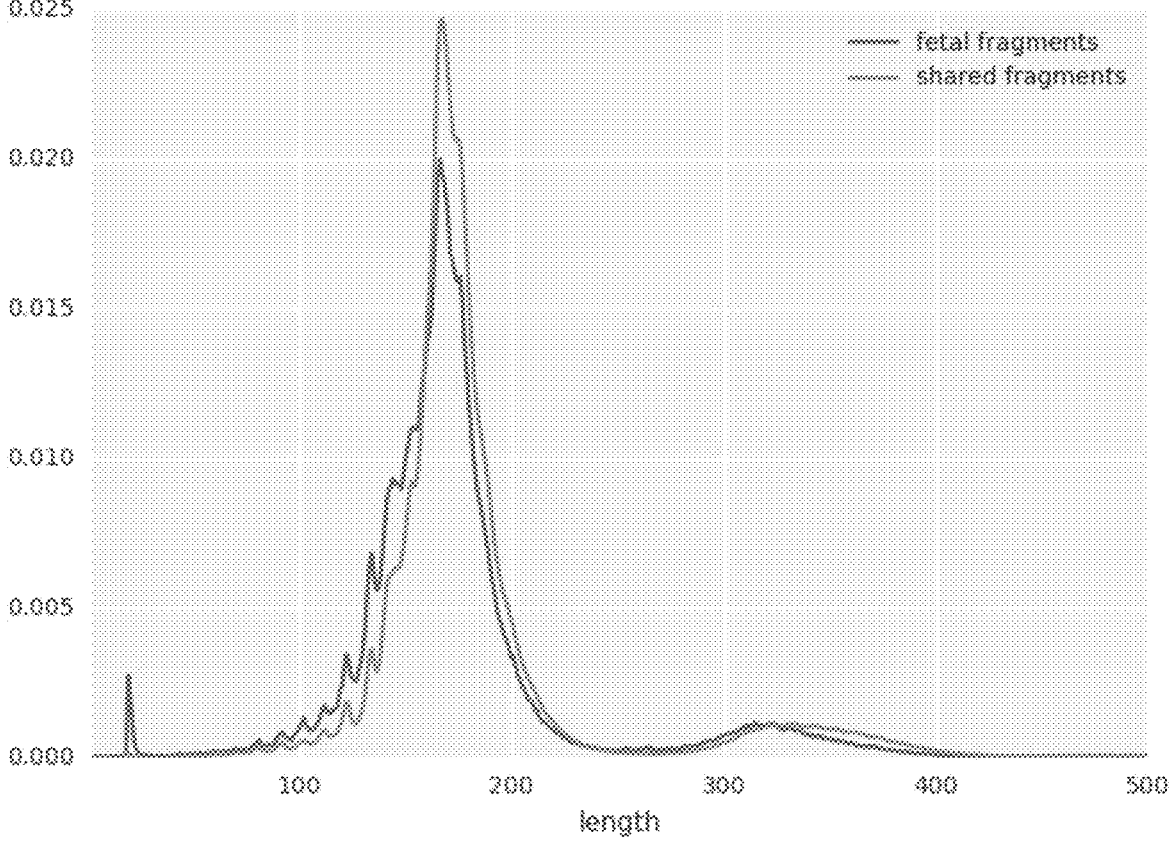
Figure 9E:
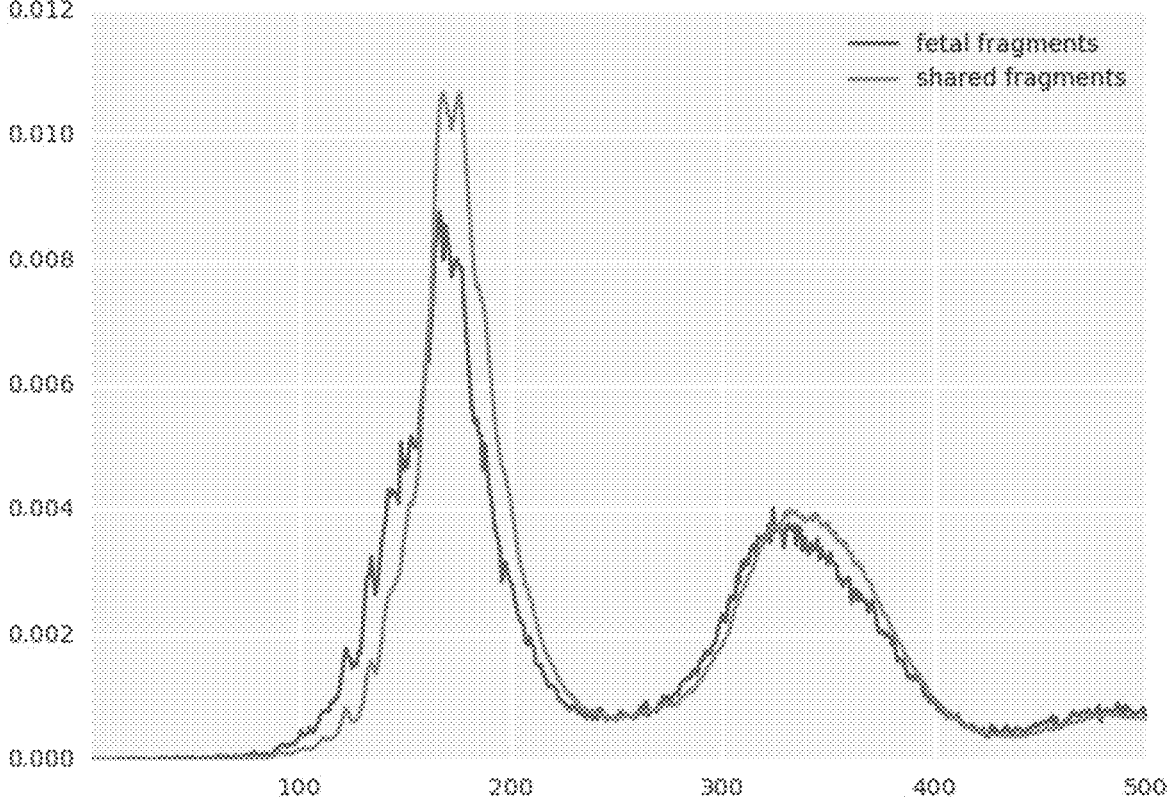
Figure 9F:
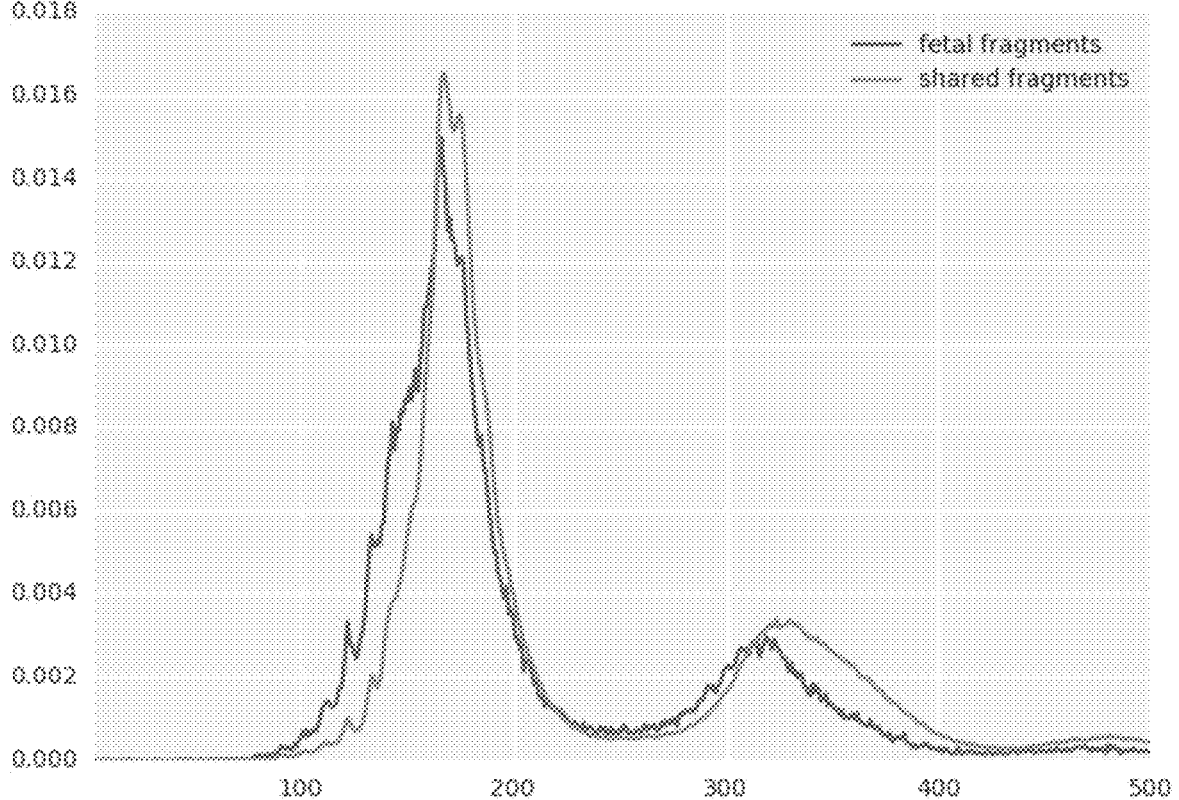
Figure 9G:
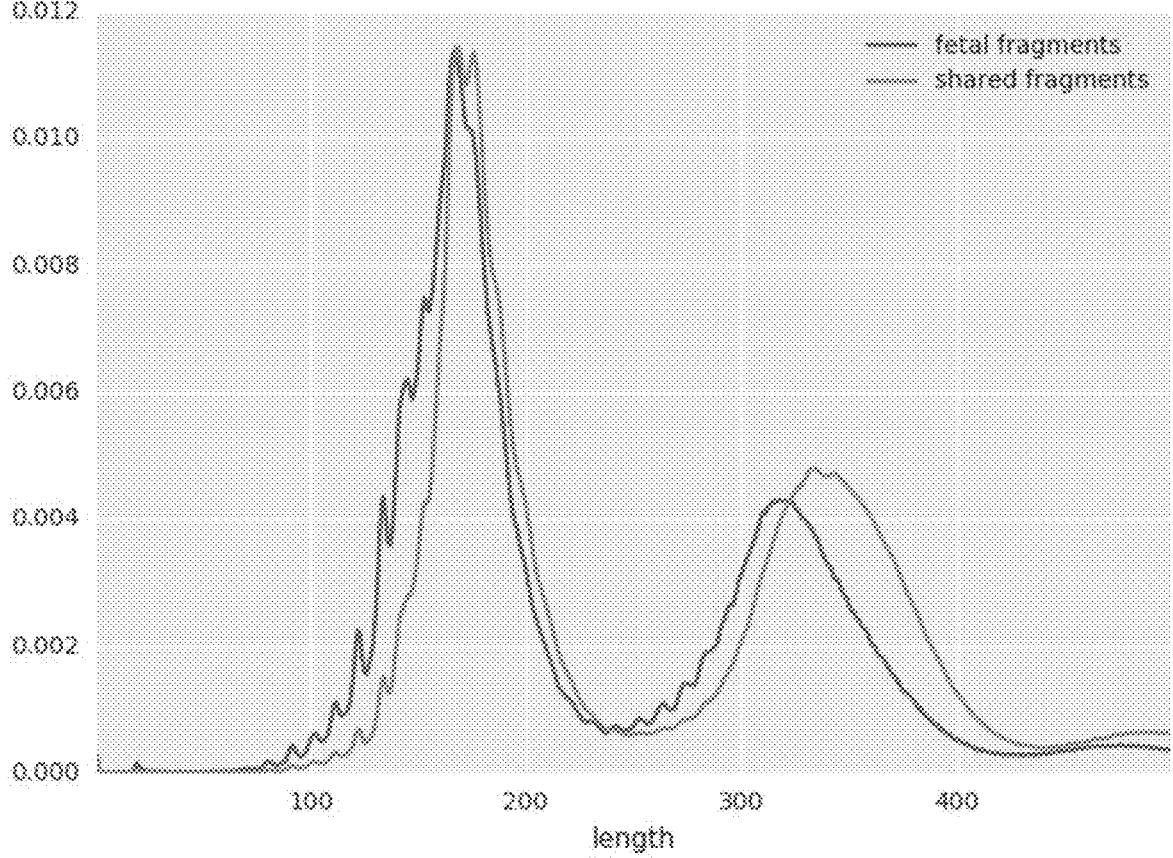

FIGS. 8A-F show performance of the model after recalibration (color codes in FIG. 8G). FIGS. 8A-F demonstrate the ability to perform machine learning-based variant recalibration for the filtering of variants. As in FIGS. 2A-D, 3A-D and 5A-G, accuracies are presented here for loci with a posterior probabilities that are higher than the thresholds appearing in the x-axis. Findings are presented before and after variant recalibration. The total accuracy for each category is the accuracy at the leftmost point on the x-axis. The total counts from which the accuracy at each threshold was calculated are presented at the bottom of each figure. FIG. 8A corresponds to maternal-only heterozygous SNPs. FIG. 8B corresponds to paternal-only heterozygous SNPs. FIG. 8C corresponds to both-parents heterozygous SNPs. FIG.

8D corresponds to maternal-only heterozygous indels, FIG. 8E corresponds to paternal-only heterozygous indels, and FIG. 8F corresponds to both-parents heterozygous indels.

FIGS. 9A-G are density plots of fragment length distribution of families G1, G2, G3, G4, E1, E2 and G5, respectively.

Figure 10:
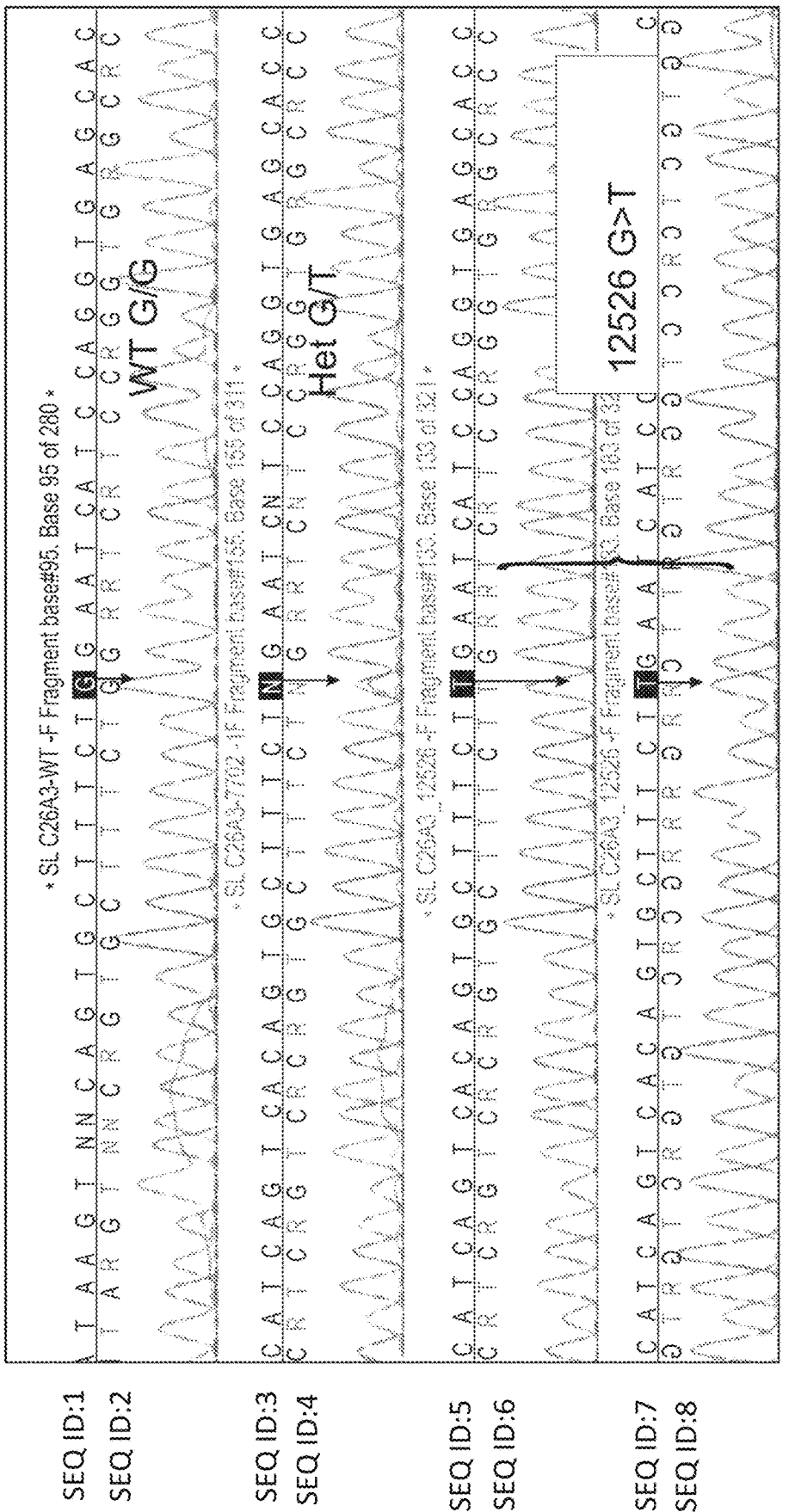
FIG. 10 shows mutation validation sanger results as obtained in experiments performed according to some embodiments of the present invention. The mutations families E1 and G5 were confirmed using Sanger. The first row demonstrates a control that is homozygous to the reference allele (G). The second row shows the father, who is a carrier of the alternate allele (T). The third and fourth rows show the results of the fetus, once using a forward primer and once using a reverse primer. The fetus is homozygous to the alternate allele. The numbers SEQ ID: 1-SEQ ID: 8 at the lefthand side represent SEQ ID Nos 1-8, respectively.

FIG. 10 shows confirmation results of the mutation in gene SLC26A3 for family E1, as obtained using Sanger sequencing. The first row demonstrates a control that is homozygous the reference allele (G). The second row shows the father, who is a carrier of the alternate allele (T). The third and fourth rows show the results of the fetus, using a forward primer (third row) and using a reverse primer (fourth row). The fetus is homozygous to the alternate allele.

DISCUSSION

In this Example, noninvasive fetal genotyping was demonstrated using the method of the present embodiments. This Example demonstrated that the size differences between maternal- and fetal-derived fragments improve cfDNA-based fetal genotyping. These results were prominent at sites where the mother is heterozygous, which currently pose the greatest identification challenge. This Example also demonstrated the ability of the method of the present embodiments to predict fetus indels. Indels are the second most common type of variants and can be deleterious, especially when they affect the reading frame.

One advantage of the Bayesian approach is that it is modular, in the sense that it allows one to add any available information. In the present case, fragment size information was used, but other features can additionally or alternatively be also included. These include other characteristics of cffDNA, e.g., clusters of preferred ending positions. Also contemplated, is haplotype information. Cell-free DNA that is enriched for cffDNA can also be processed by the method according to some embodiments of the present invention.

The accuracy calculations shown in the analysis of this Example are based on raw, unfiltered results, so that the actual accuracy is higher than that reported herein. The accuracy depends also on features that were not optimized in this study. In this Example, prediction was applied to all sites, even those with low confidence, and returned all the relevant information that was used at each site. Then, different annotations, statistical tests, and machine learning methods can be applied, so that the low confidence results are filtered out, as demonstrated in the machine learning recalibration step. This consistency with the accepted process of variant calling is another advantage that is allowed by the Bayesian approach, since the posterior probabilities constitute the calibrated parameter that is used for filtering.

This Example demonstrates both exome and genome sequencing. Compared to deep WGS data, the accuracy achieved when applying the method of the present embodiments on deep WES data was not high at positions where the mother is heterozygous. These results were obtained in an early, clinically relevant week of pregnancy, in which DNA-amplification was required. With amplification-free WGS this example showed that the method is accurate even in this early stage of pregnancy. To achieve high accuracy also in smaller regions of the genome, other library preparation and sequencing methods will be tested.

This Example demonstrates that the NIPD of a large range of SGDs can be obtained with available technology such as NGS. The probabilistic scaling used in this Example ensures that some percentage of the predicted sites has a certain prediction. These sites can be used in downstream analysis in order to find rare variants that are yet to be discovered. WES can be used according to some embodiments of the present invention for a large cohort study owing to its low cost. This is advantageous over conventional techniques since with WES it is possible to create a large and uniform dataset that can be further analyzed in order to improve the model.

Example 2

This Example shows that a deep learning procedure can be used for accurate detection of small variants in the fetus in a noninvasive manner. The deep learning procedure can in some embodiments of the present invention replace the Bayesian model and the machine learning recalibration procedure used in Example 1, and can be used in an end-to-end framework. One of the advantages of these embodiments is that deep learning procedure can automatically model systematic errors. This is useful in data that is harder to interpret, such as low-depth sequencing. The Inventors found that the end-to-end deep learning outperforms the Bayesian model. For example, the deep learning procedure can handle low fetal fraction and sequencing coverage, which are the main limiting factors in this task.

Unlike in the case of Bayesian model, the deep learning procedure can provide an approximation of an unknown interdependent likelihood function. This function utilizes the relationship between reads covering a position, as well as adjacent nucleotides, in all three individuals. The Inventors of the present invention found that the use of deep learning procedure can be applied to utilize characteristics other than lengths (e.g., the nucleotide sequence itself). The deep learning procedure can be applied for a variety of sequencing platforms (Illumina, Nanopore, etc.) and methods (WES, WGS, panels, etc.).

Figure 11:
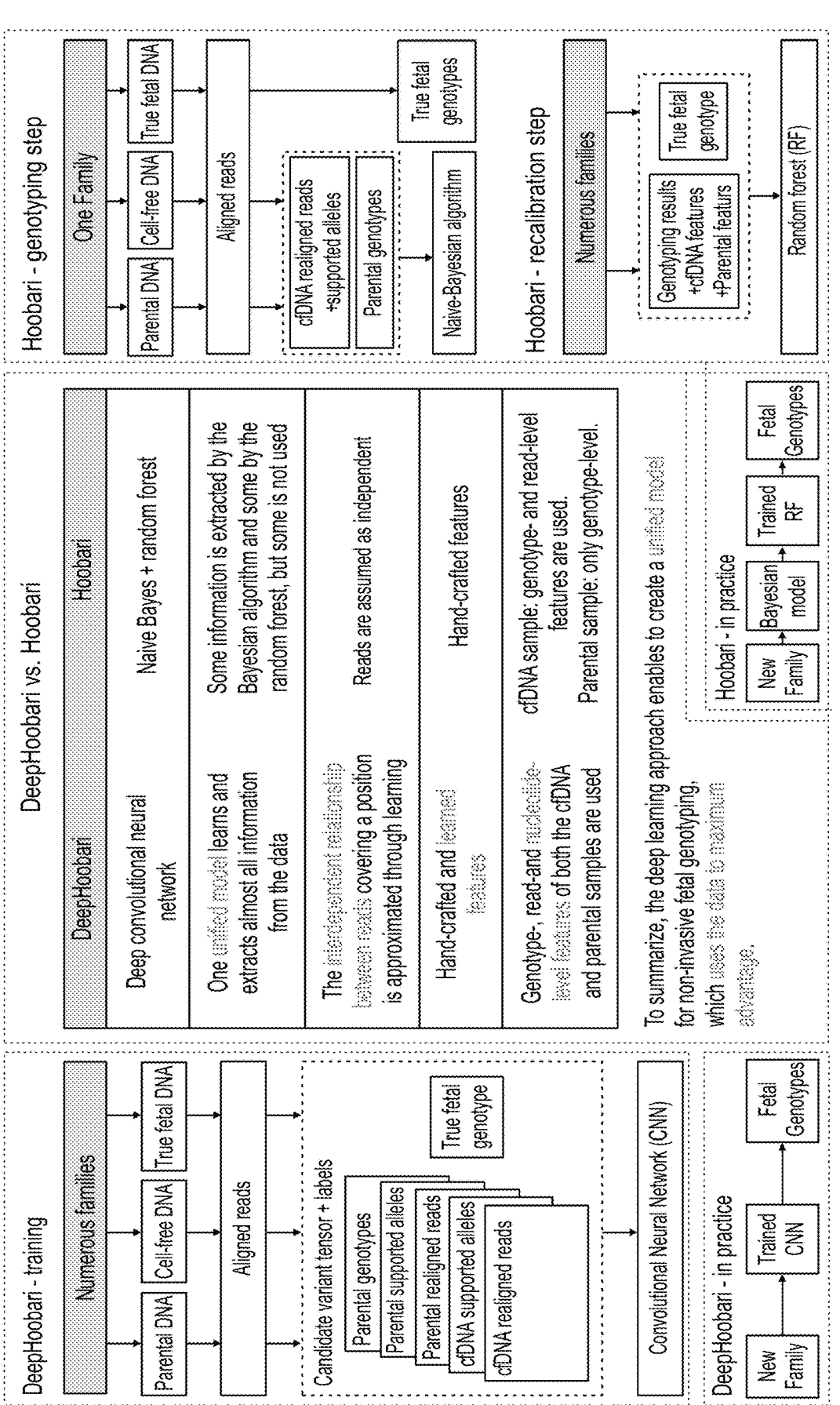
FIG. 11 is a diagram summarizing the differences between a Bayesian model (referred to as Hoobari in FIG. 11), and the end-to-end deep learning model (referred to as Deep-Hoobari in FIG. 11).

FIG. 11 summarizes the differences between the Bayesian model (referred to as Hoobari in FIG. 11), and the end-to-end deep learning model (referred to as DeepHoobari in FIG. 11).

Artificial Neural Network

The artificial neural network is optionally and preferably a convolutional neural network (CNN).

Feature Extraction

The data from the cfDNA and the parental DNA can be represented using the aligned reads and their metadata, such as their base qualities (nucleotide-level information) or mapping qualities (read-level information) or any one of the features listed in Table A.1 of ANNEX 1. Alternatively, or additionally, variant calling software such as, but not limited to, GATK's HaplotypeCaller, Google's Deep Variant or Freebayes, can be used to extract information about possibly supported alleles. This information is the level of the genomic locus. Different levels of data can be used for the cfDNA, the mother and the father. In some embodiments of the present invention data sources are reduced, for example, by reducing the used depth of coverage, and/or avoiding the utilization of the parental information.

Pileup Tensor for cfDNA

In the learning stage, all the data corresponding to a certain locus in the genome is optionally and preferably represented by an input multi-dimensional tensor that is associated with a label comprising the true fetal genotypes that are found using an invasive test. The CNN receives a batch of input multi-dimensional tensors and their labels in each iteration (forward and backward propagation).

The tensor can be, for example, a pileup of reads that cover a candidate SNP, centered around the assessed SNP.

This way, the first two dimensions of the tensor (e.g., width and height), correspond to the length of the pileup and the number of reads. The reads can be encoded in any technique, including, without limitation, one-hot encoding, group-hot encoding, and the like. The third dimension of the tensor (e.g., depth) is the number of input channels of the CNN, each channel providing metadata for the SNP. In some embodiments of the present invention the representation of information by channels is processed by multiplication functions wherein the outputs of the multiplication functions constitute the channels within the tensor.

Experimental Design

Datasets

The datasets used in this study are listed in Tables 3A and 3B, below. The study was designed to prevent overfitting of the predicting model. Four families were analyzed: families G1-G2 included high quality data, and were sequenced in a previous study; family G5 included high quality data, but is biologically more challenging, as it was sequenced from a first trimester pregnancy; family E1 is also challenging, as it was sequenced using WES, which has been shown to be more erroneous.

TABLE 3A

| | | Sequencing[2] | | Depth of coverage[3] | | |
| | | Parents + | | | | |
| Dataset | #Variants[1] | cfDNA | Fetus | cfDNA | Mother | Father |
|---|---|---|---|---|---|---|
| G1[a] | 3830890 | WGS | WGS | 270 | 40 | 45 |
| G2[a] | 4086308 | WGS | WGS | 195 | 40 | 60 |
| G5 | 4326937 | WGS | WGS | 310 | 38 | 41 |
| E1 | 71579 | WES | WES | 735 | 99 | 93 |

TABLE 3B

| | | | Ground truth (fetus) | |
| Dataset | Fetal fraction | Week[4] | Source | Depth |
|---|---|---|---|---|
| G1[a] | 30% | 38 | Cord blood | 50 |
| G2[a] | 23% | 18 | Placenta | 60 |
| G5 | 18% | 11 | Placenta | 38 |
| E1 | 12% | 11 | Placenta | 97 | a) Chan et al., 2016; b) Kitzman et al., 2013; 1) biallelic variants found on autosomes, with lenient filtering of parental and fetal depth ≥5, and cfDNA depth ≥20; 2) Whole genome sequencing (WGS) was performed following a PCR-free library-preparation protocol; 3) Median, on target; 4) Gestational age.

Phase 1

The first phase of the study the represtation of the data, the structure of the tensor, and the network's infrastructure were selected, based on dataset G1, which was divided to a training set (80% of the variants) and a test set (20% of the variants). The training was further divided to 90% training and 10% validation sets. As these number of variants are still very large, they are further sampled for most of the experiment. Once a satisfying architecture was chosen, it was tested only once over the test set. The architecture was also tested over G2 to present a best-case scenario, in which the technical differences between families were the smallest (families were sequenced using the same method by the same lab).

Phase 2

Datasets G1 and G2 are merged to one dataset. This dataset is divided to training, validation and test sets. The architecture selected in Phase 1 is trained and tested. Thereafter, the architecture is tested over dataset G5, to show a more challenging scenario, in which there are technical differences between the families used for training and those used as test. This demonstrates the model's generalizability.

Phase 3

Dataset E1 is similarly divided, but with a larger test set, to maintain a sufficient amount of variants. The model from the previous phases is used for transfer learning, where the trained-model was further trained and fine-tuned. In a separate or alternative process, the architecture from the previous phases is trained solely based on the training set of E1.

Additional Experiments

The experiments in phases 1-3 can be repeated using Indels. Further experiments can include (1) down-sampling of both sequencing depth and fetal fraction; (2) excluding data from the father; (3) excluding data from both parents; and (4) reducing the required parental information to genotype-only, such that NGS is required only for the cfDNA.

Results

Figures 12A, 12B, 12C, 12D:
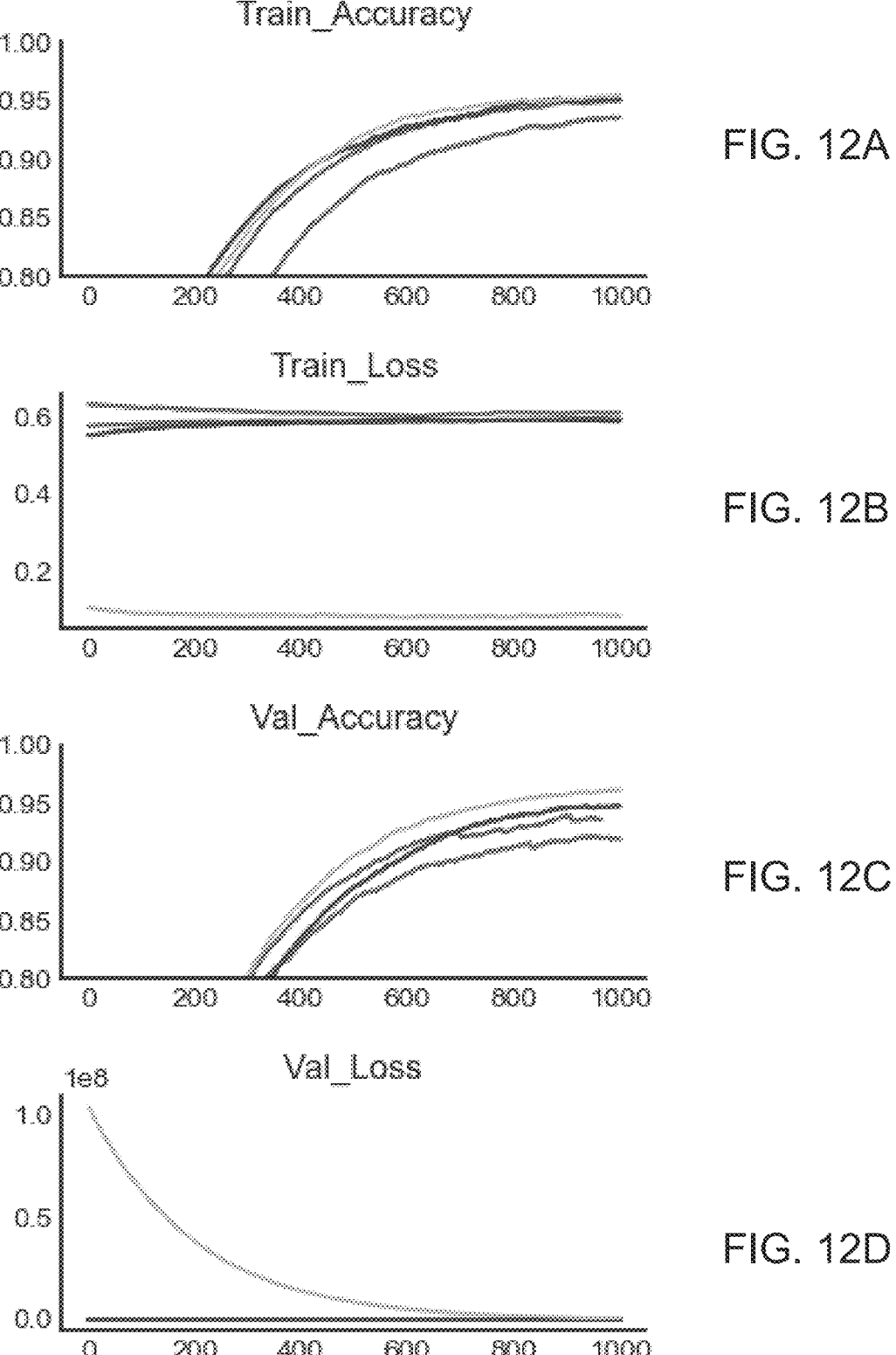
FIGS. 12A-P show results of a first phase of an experiment, preformed according to some embodiments of the present invention using a machine deep learning procedure. Shown are accuracy and loss results over SNPs in sub-sampled dataset G1, using four tested networks.
Figures 12E, 12F, 12G, 12H:
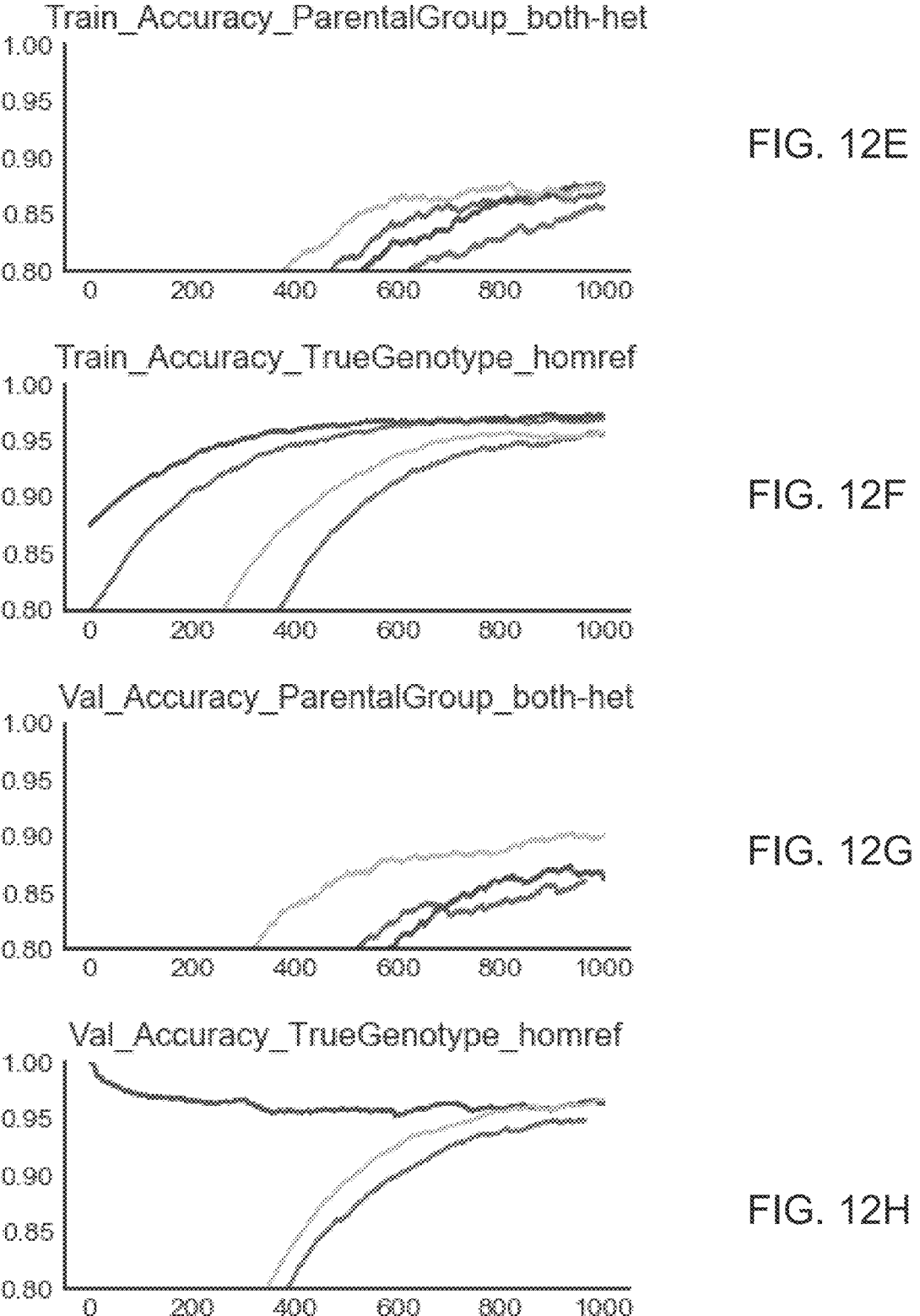
Figures 12I, 12J, 12K, 12L:
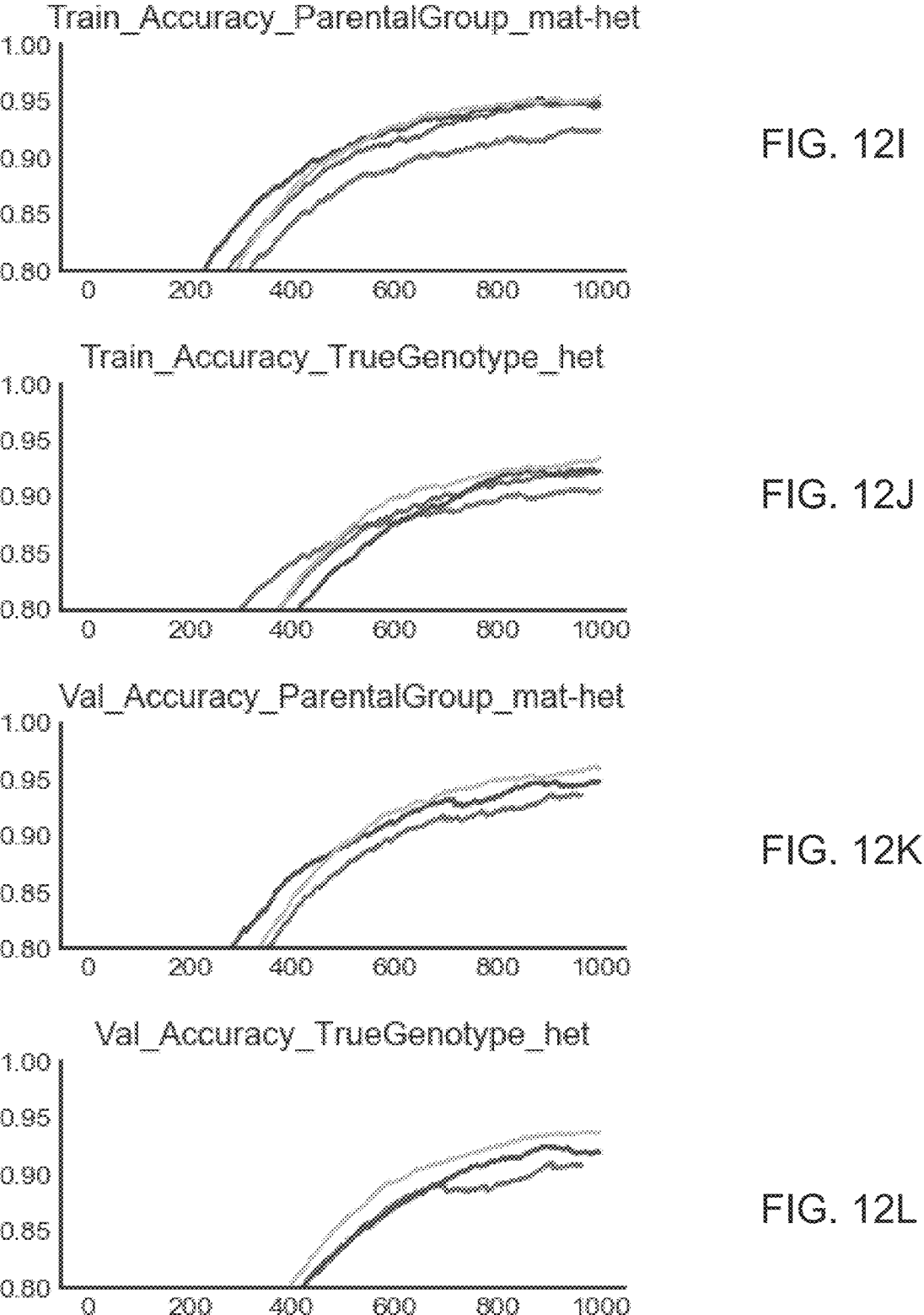
Figures 12M, 12N, 12O, 12P:
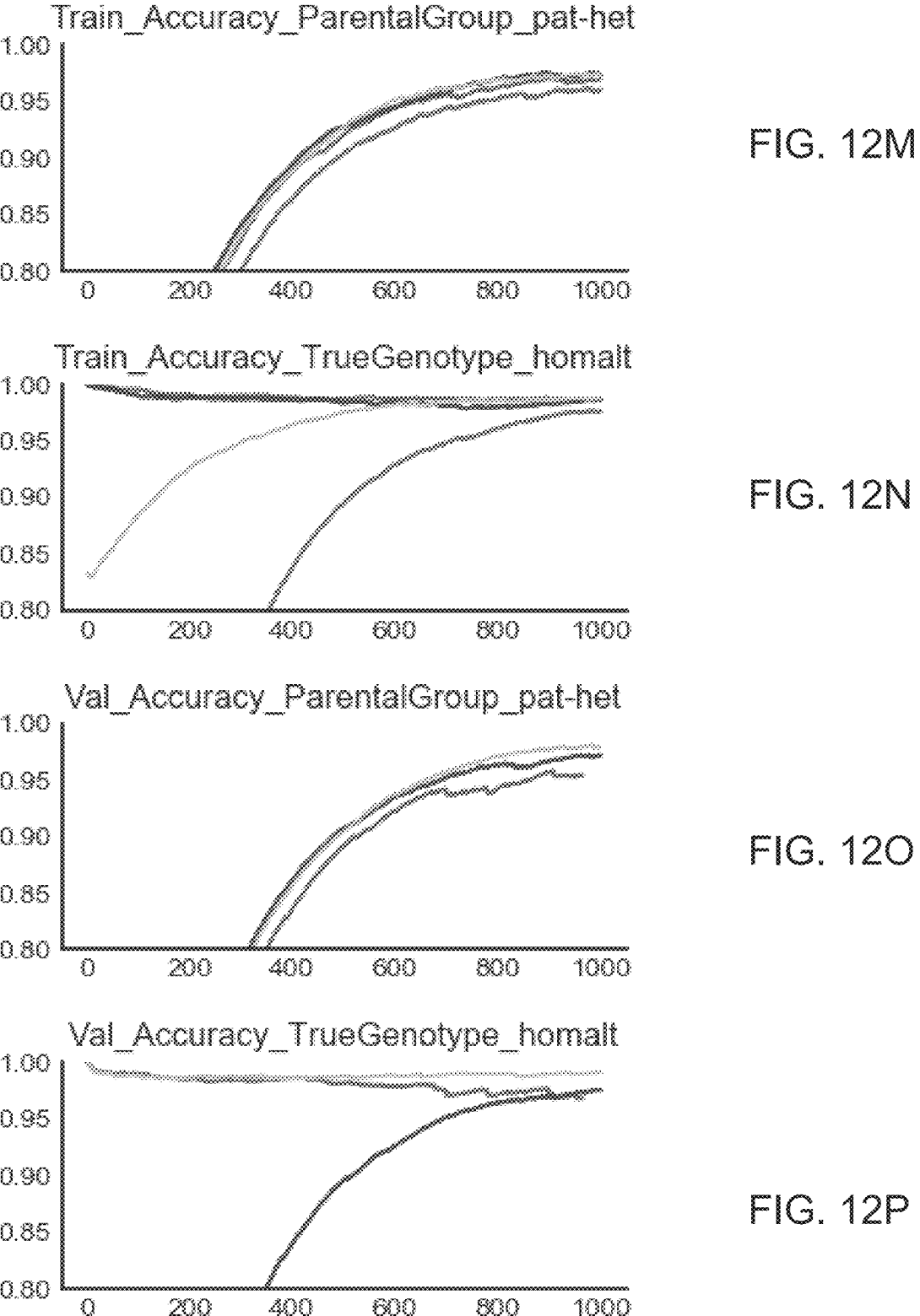

In phase 1, the tensor was based on aligned reads, and GATK's HaplotypeCaller was used to perform a more accurate realignment and to assign each read with its supported allele. The assignment of alleles was without calling the genotype, since HaplotypeCaller is not designed for pregnancy cfDNA samples and would treat the samples as if they originate from one individual. A tensor that is based on such read alignments from the cfDNA and parents was found to match the accuracy of Hoobari. The results are presented in FIGS. 12A-P, showing simple CNN (red). CNN with cfDNA reads sorted by fragment length (green). CNN with cfDNA reads sorted by fragment length and parental reads sorted by supported allele (blue), and Inception v3 CNN (yellow), for the training set (FIGS. 12A, 12B, 12F, 12F, 12I, 12J, 12M, 12N), and for and for the validation set (FIGS. 12C, 12D, 12G, 12H, 12K, 12L, 12O, 12P). Accuracy is presented in FIGS. 12A-P for the training set (FIG. 12A); for the validation set (FIG. 12C); for 3 groups of variants by parental genotype: maternal-only heterozygous (mat-het), paternal-only heterozygous (pat-het) or both parents are heterozygous (both), and for the 3 possible fetal genotypes: homozygous to the reference allele (homref), the alternate allele (homalt), and the heterozygous (het). The results of the loss (FIGS. 12B, 12D) are not comparable among these models, and are therefore not considered.

In positions where both parents are heterozygous, where the fetal genotype was formerly shown as the hardest to predict, results showed a prominent improvement compared with Hoobari. The results were improved when the parental reads were sorted by supported allele, and the cfDNA were sorted by fragment length (each read originates from fragment with a different length).

Figure 13A:
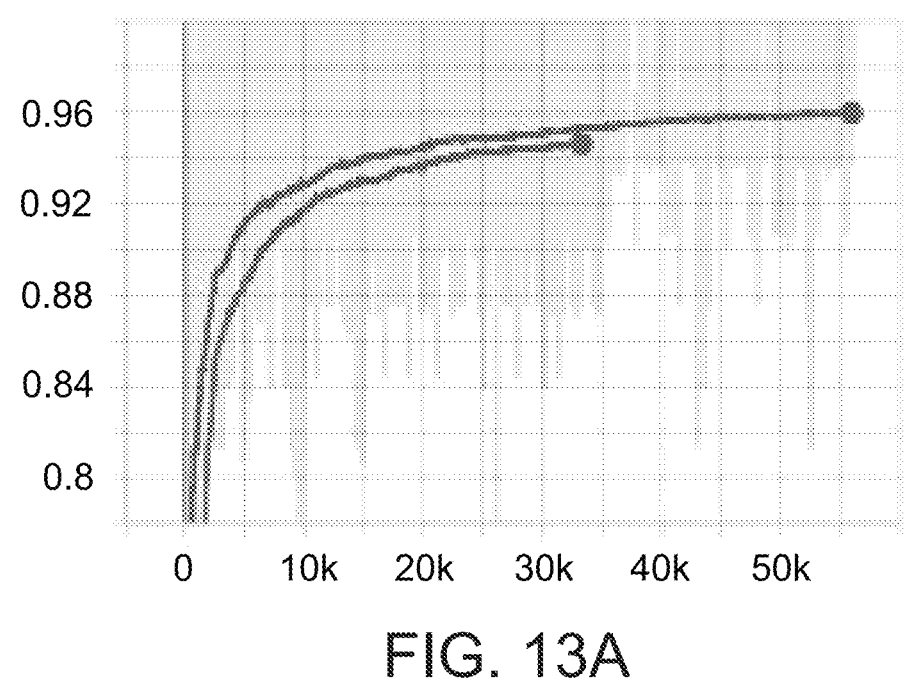
FIG. 13A-P show one-hot and group-hot encoding results of an experiment, preformed according to some embodiments of the present invention using a machine deep learning procedure.
Figure 13B:
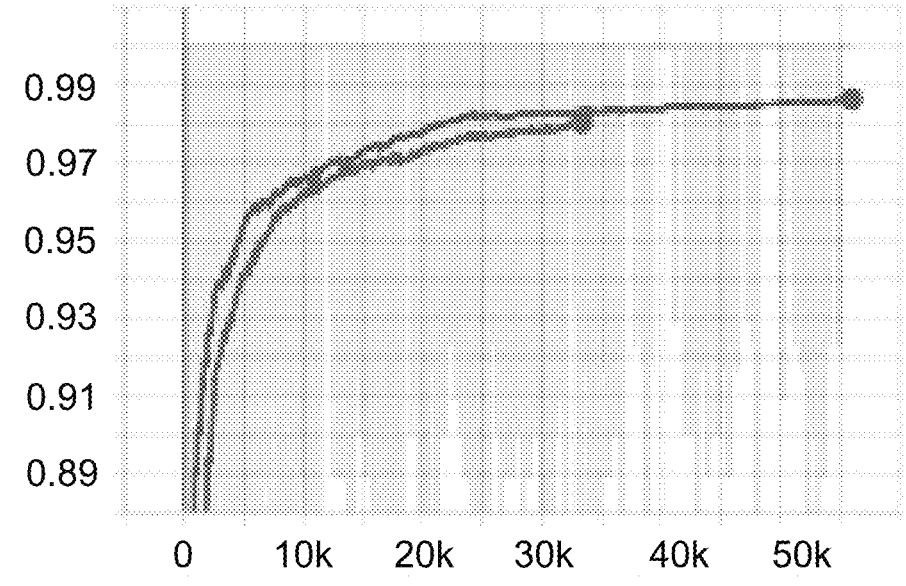
Figure 13C:
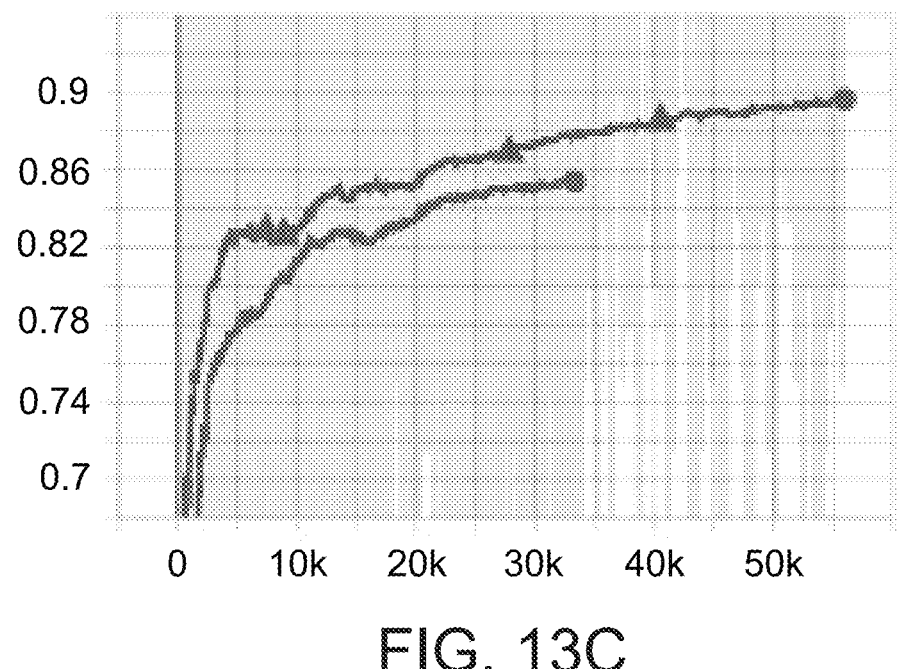
Figure 13D:
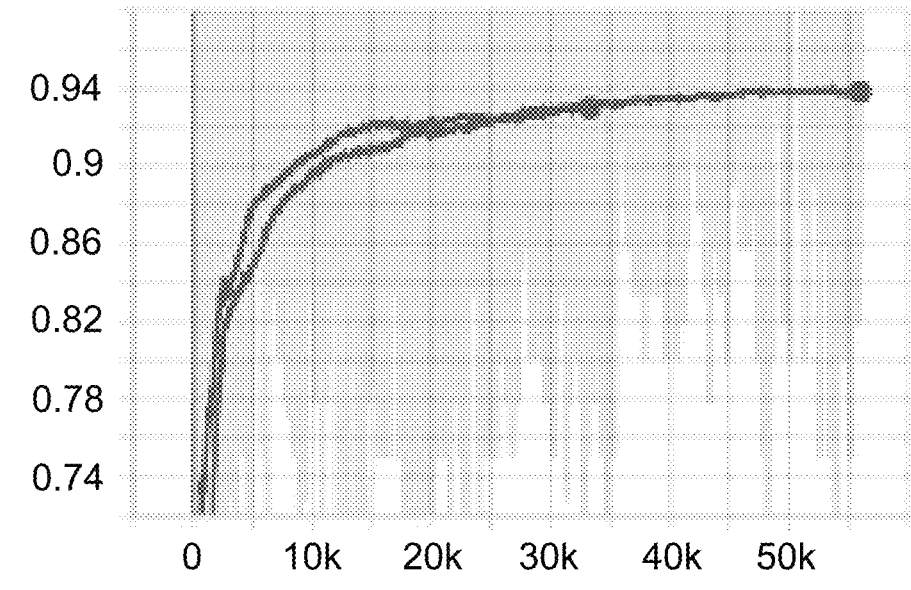
Figure 13E:
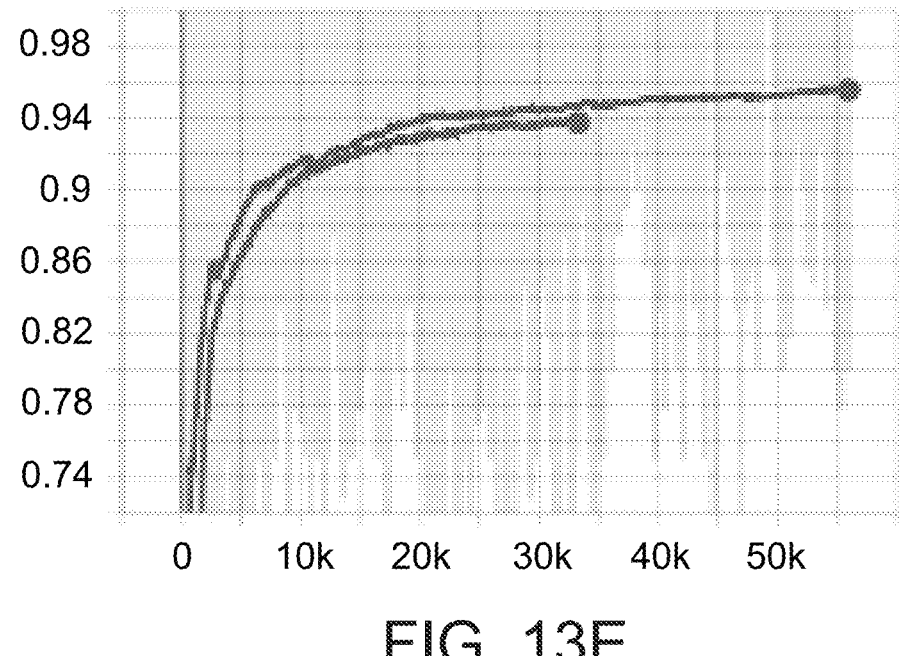
Figure 13F:
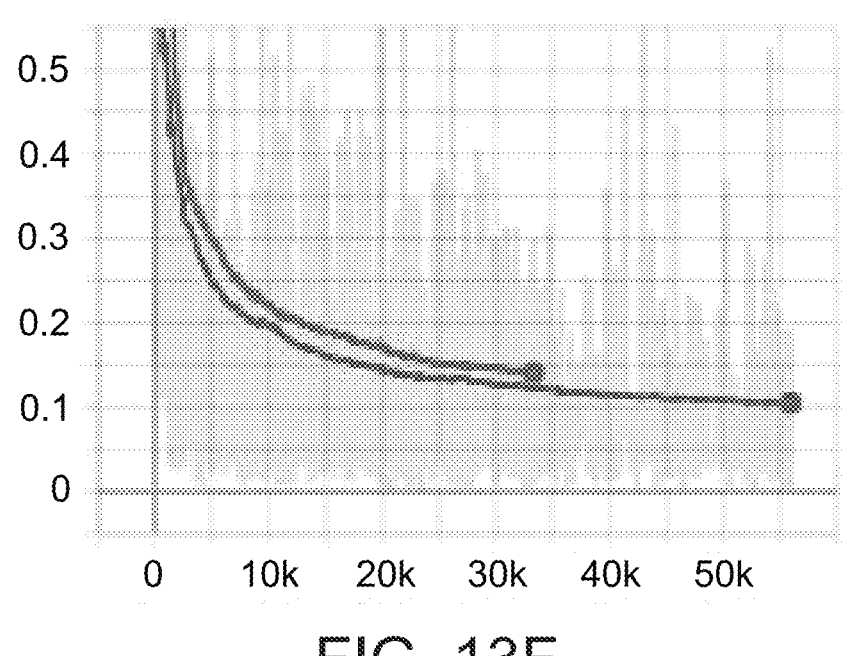
Figure 13G:
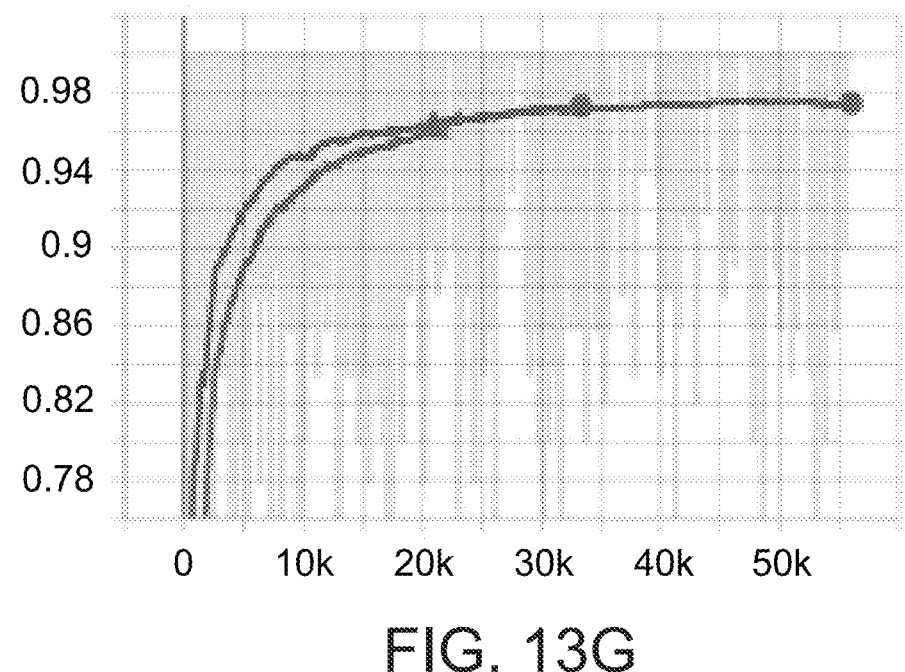
Figure 13H:
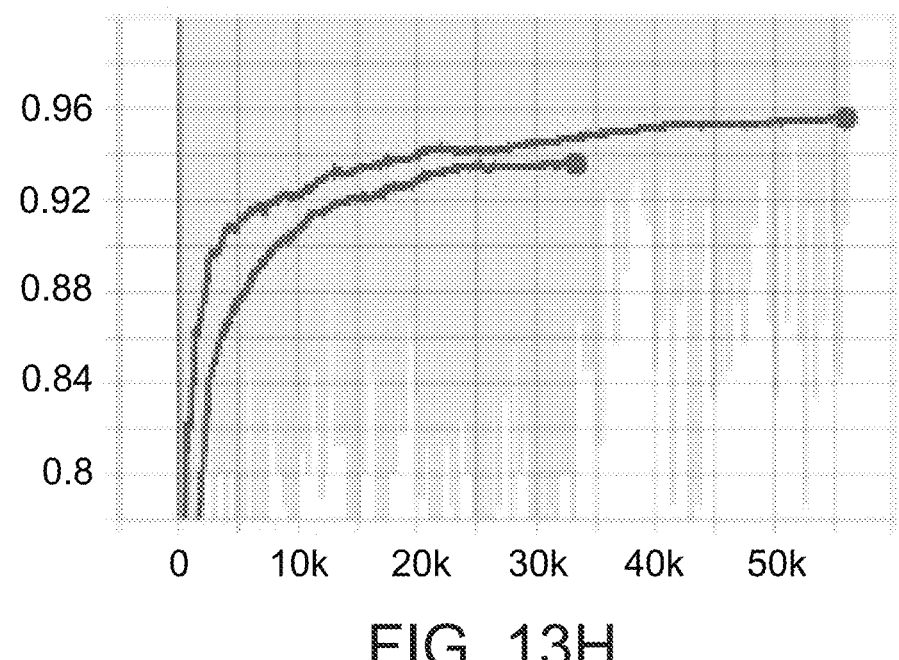
Figure 13I:
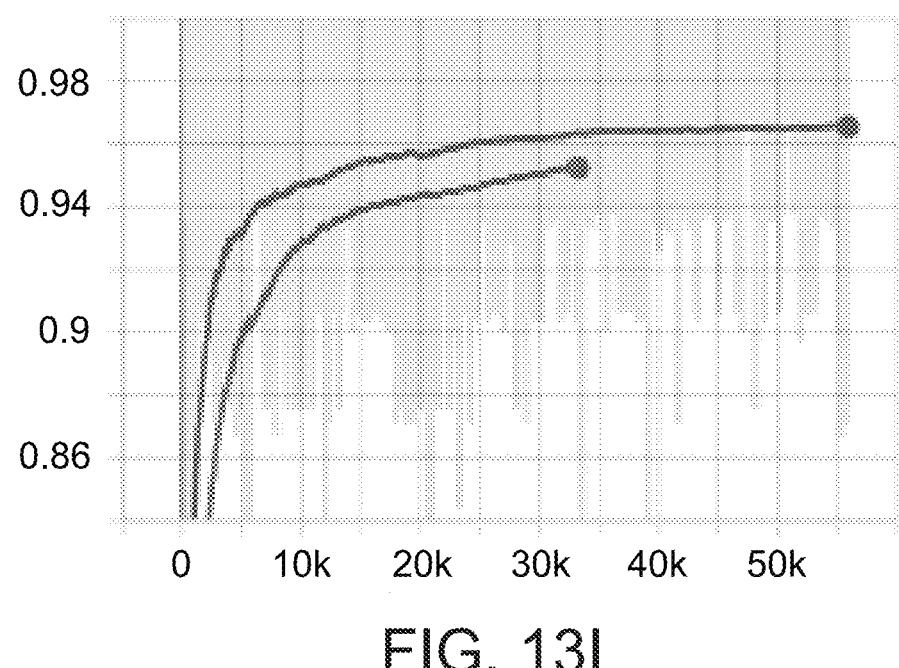
Figure 13J:
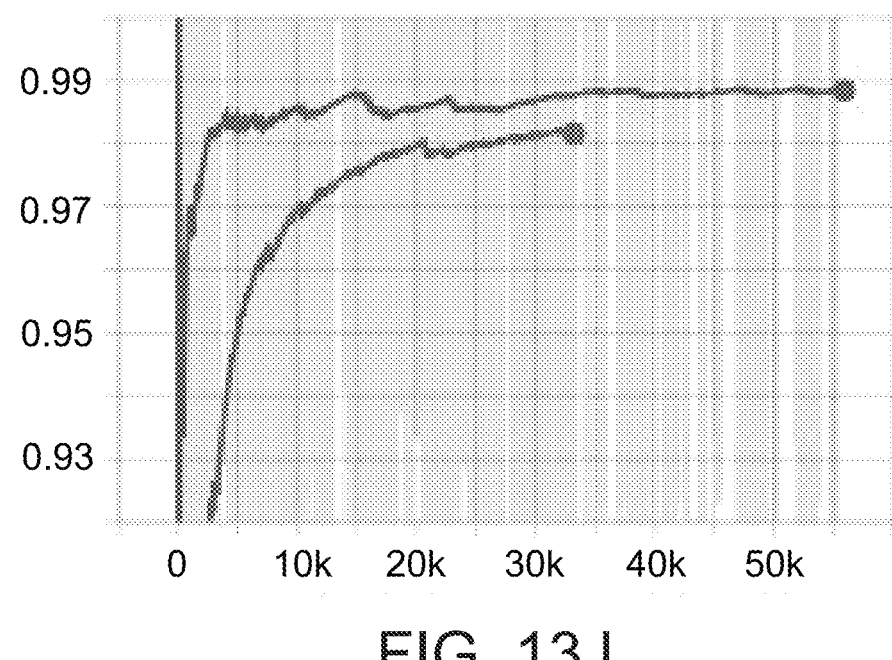
Figure 13K:
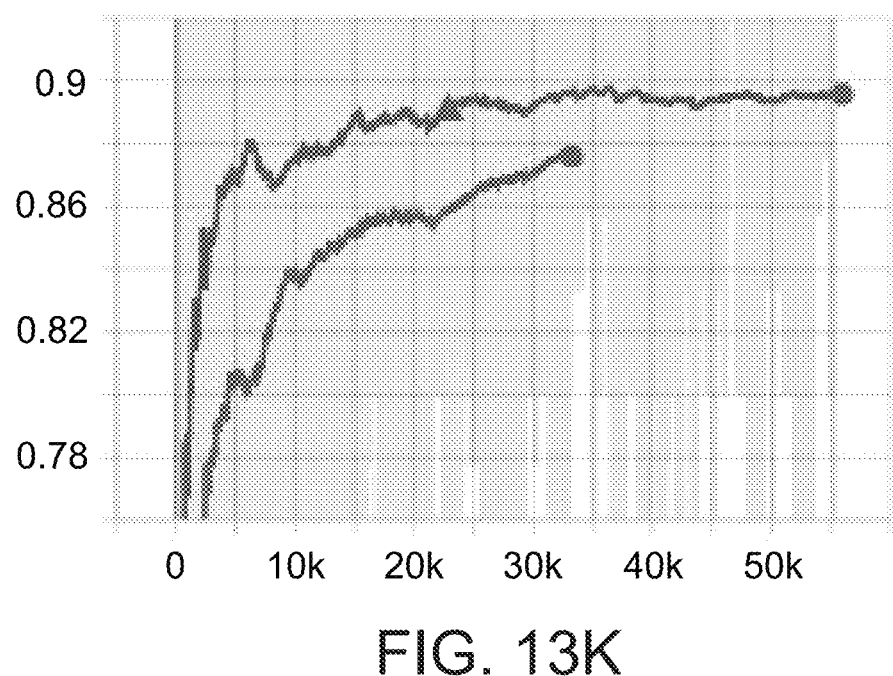
Figure 13L:
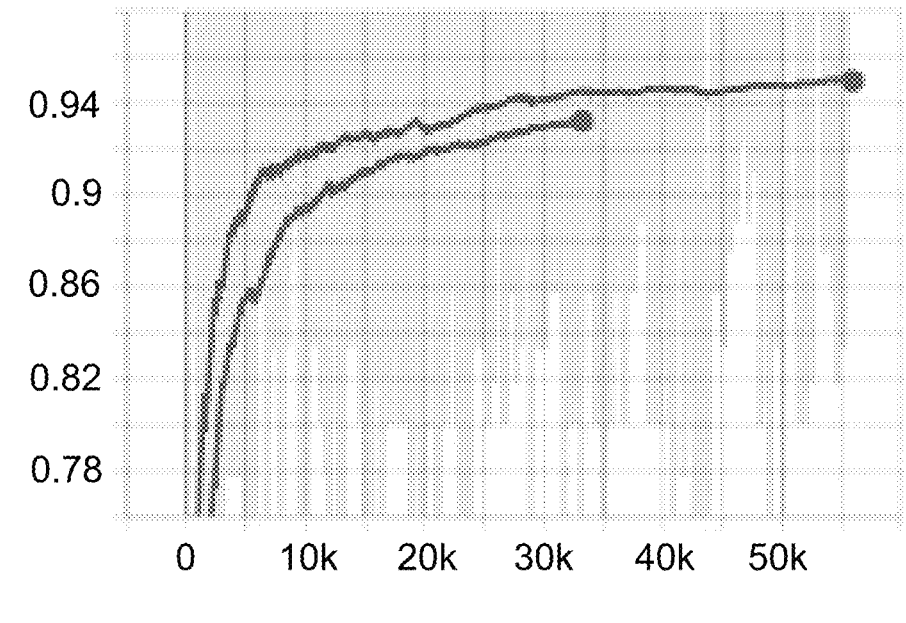
Figure 13M:
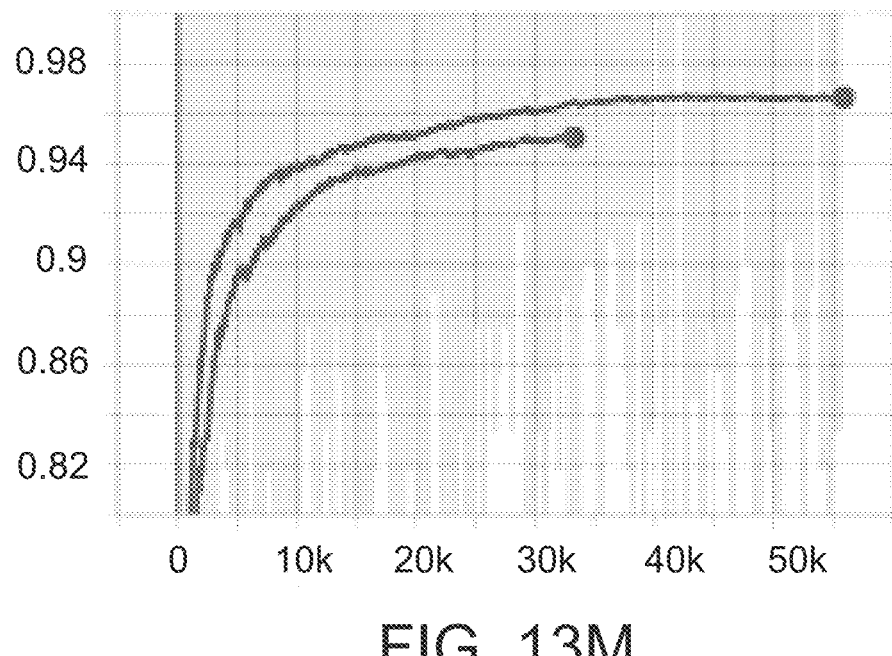
Figure 13N:
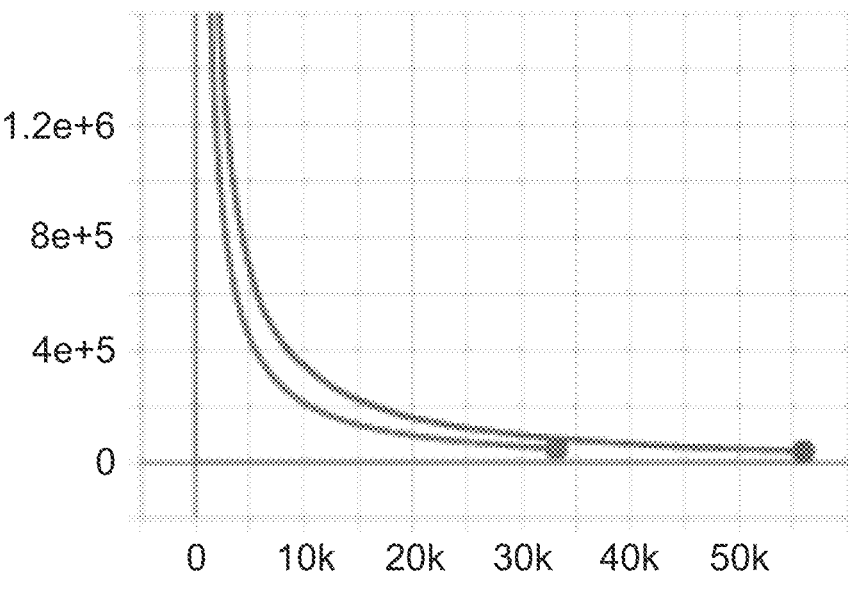
Figure 13O:
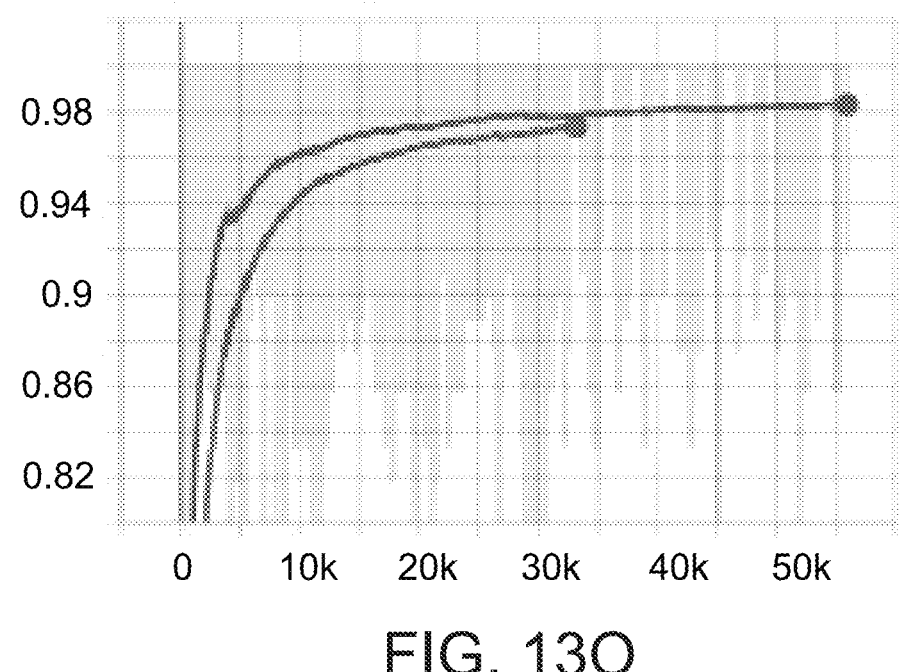
Figure 13P:
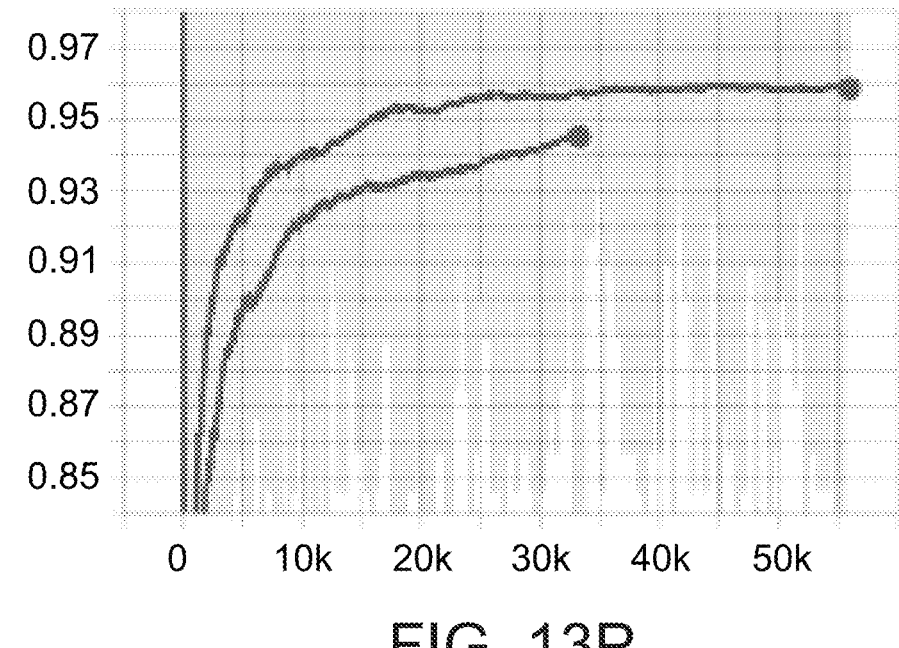

It is to be understood that more complex tensor and network architectures can be employed. For example, in a one-hot encoded tensor, each nucleotide is presented by a combination of 1's and 0's representing its base quality, multiplied by the respective confidence. The bases A, C, G and T can be encoded over four channels, e.g., as 1000, 0100, 0010 and 0001, respectively. If, for example, the base A was sequenced with confidence of 0.999, then the first channel is assigned with 1*0.999=0.999, and the other channels will show 0*0.999=0. Another examples is a group-hot encoded model, in which the one-hot encoded nucleotide is multiplied by a vector of all the other features. The results for these representations of the data are shown in FIGS. 13A-P, for the one-hot (blue) and group-hot (pink) representations. Accuracy and loss are presented for the same groups as in FIGS. 12A-P. As demonstrated in FIGS. 13A-P, the one-hot and group-hot representations improve the CNN's ability to learn the features of the data.

Figure 14A:
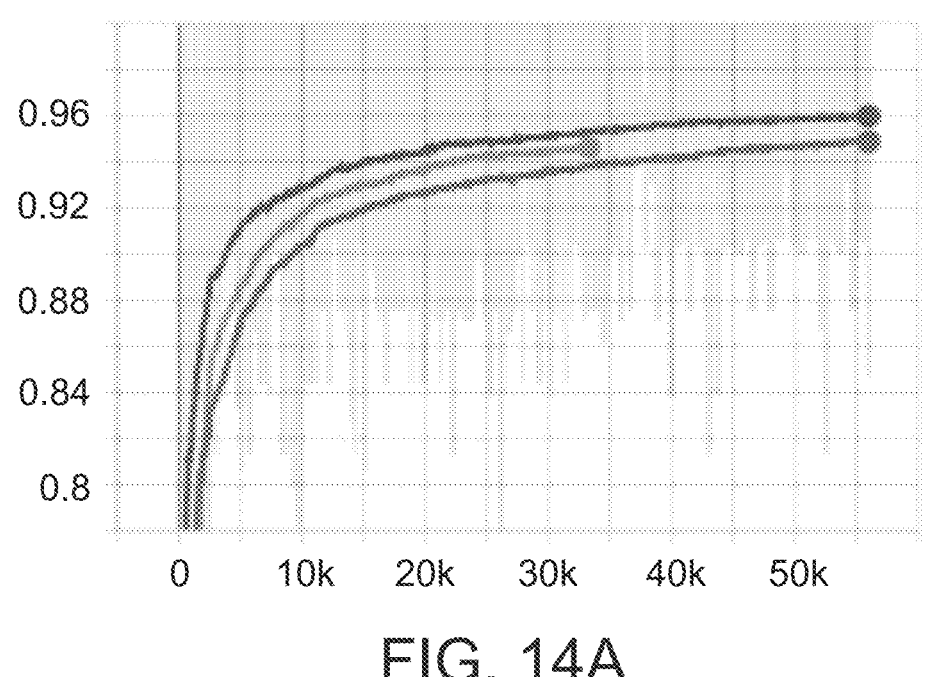
FIG. 14A-P show results of a first phase of an experiment, preformed according to some embodiments of the present invention using a machine deep learning procedure, when using only genotypes for the parental information.
Figure 14B:
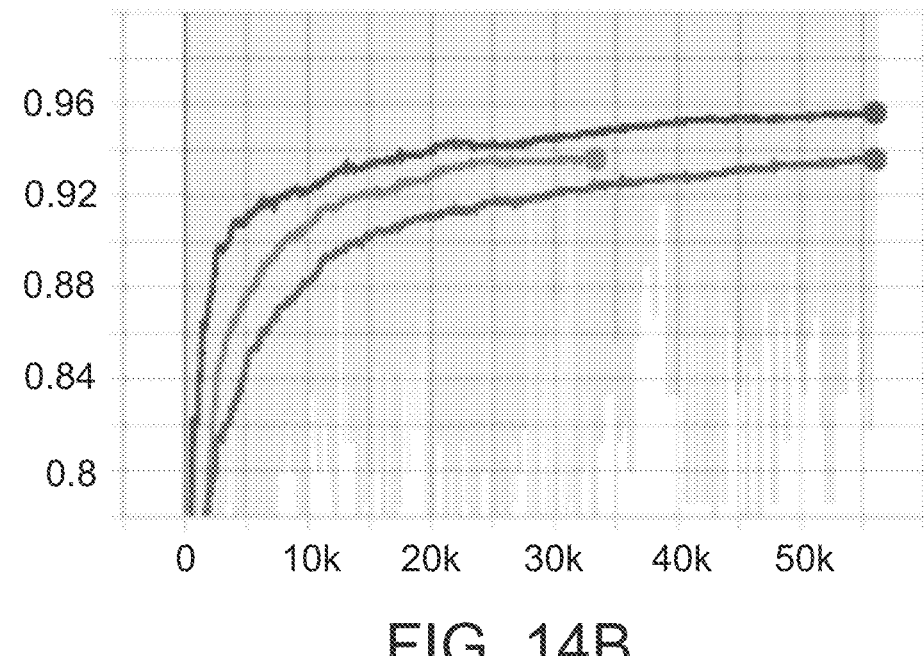
Figure 14C:
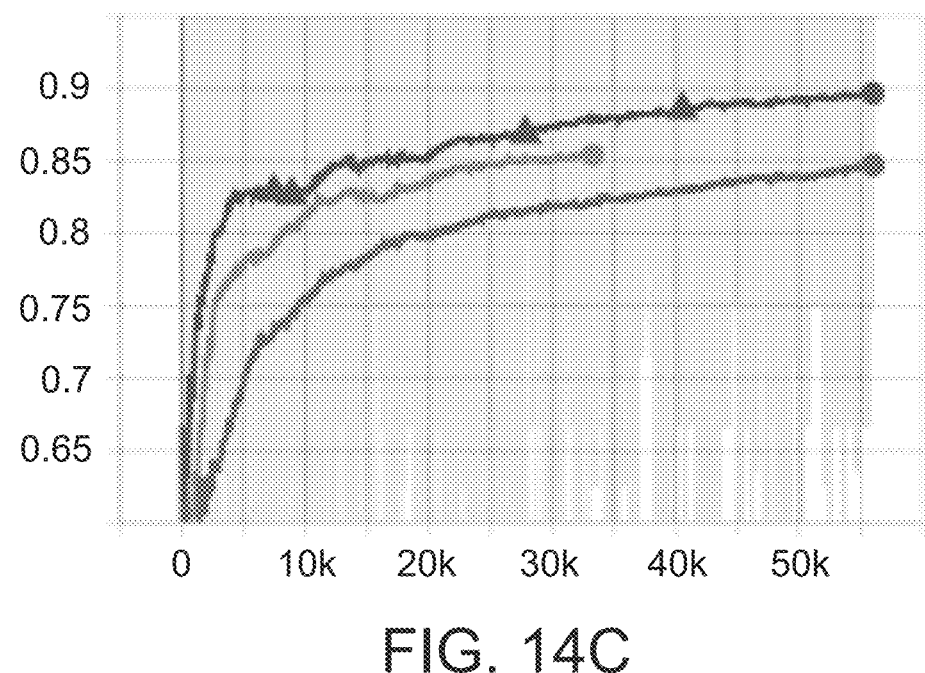
Figure 14D:
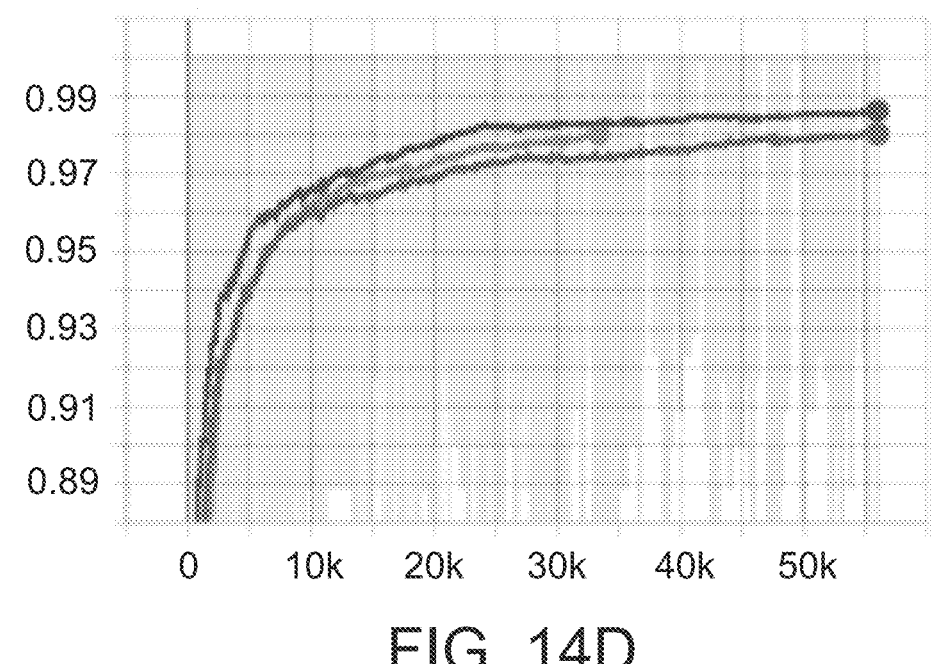
Figure 14E:
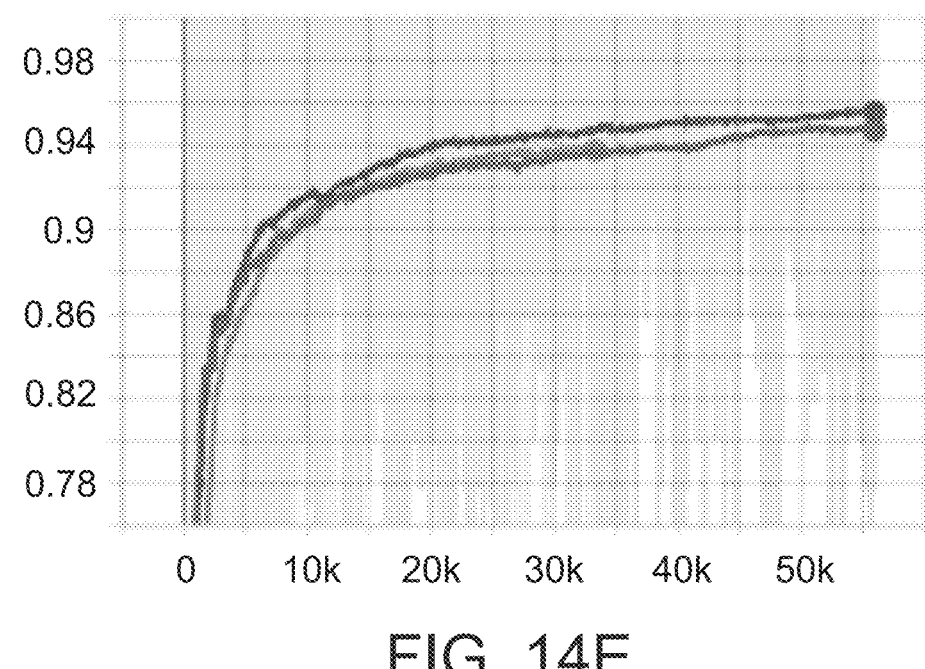
Figure 14F:
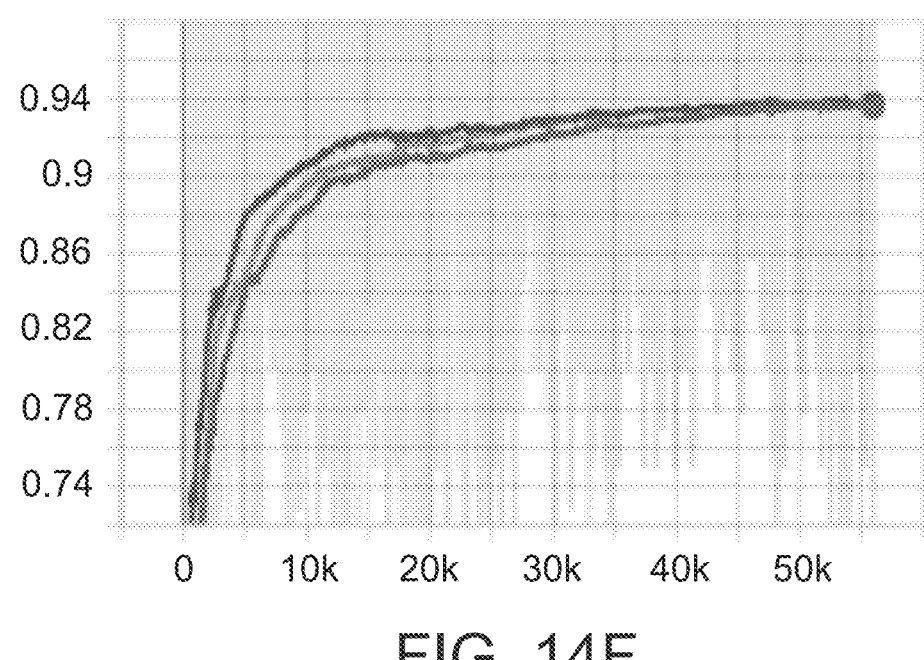
Figure 14G:
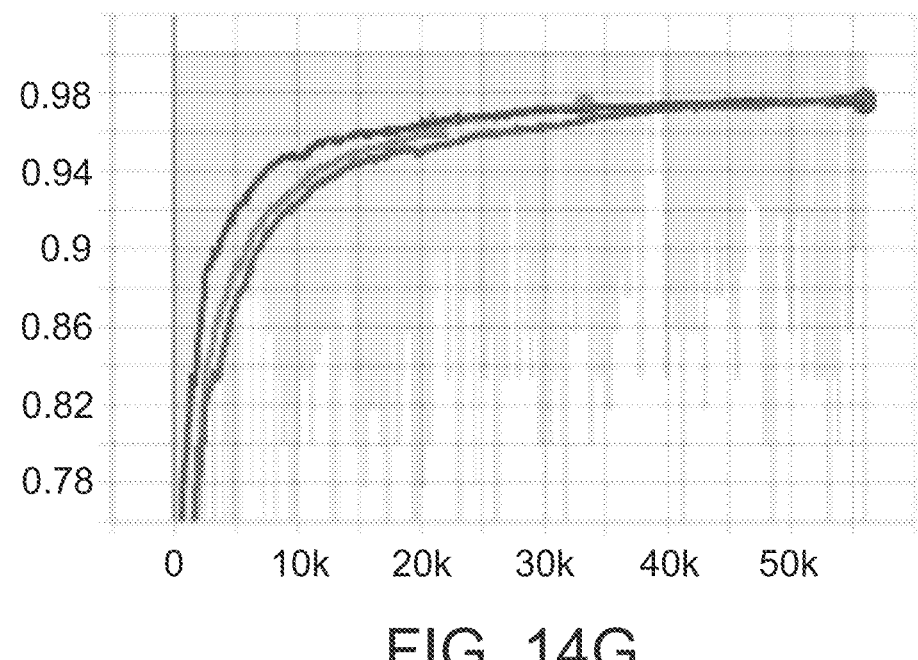
Figure 14H:
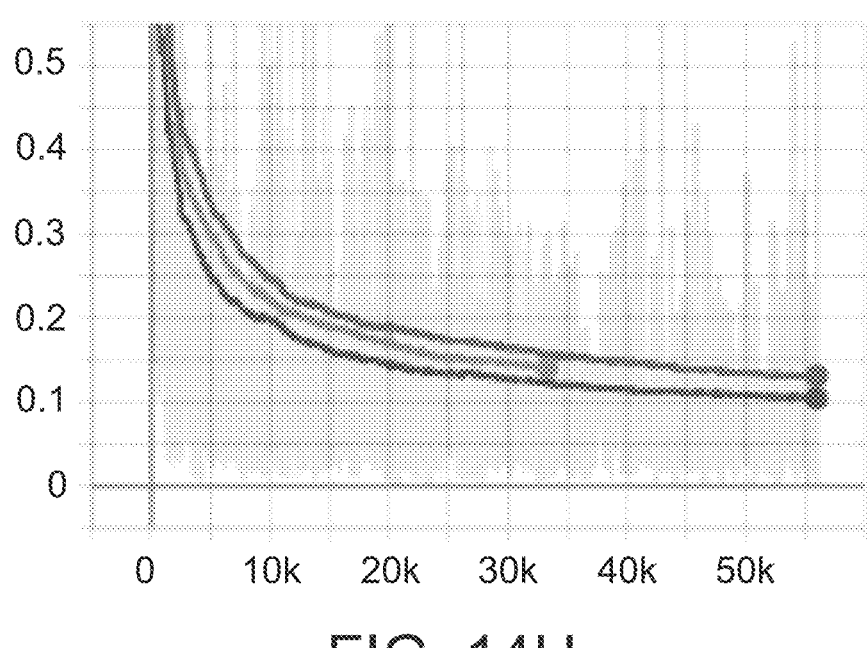
Figure 14I:
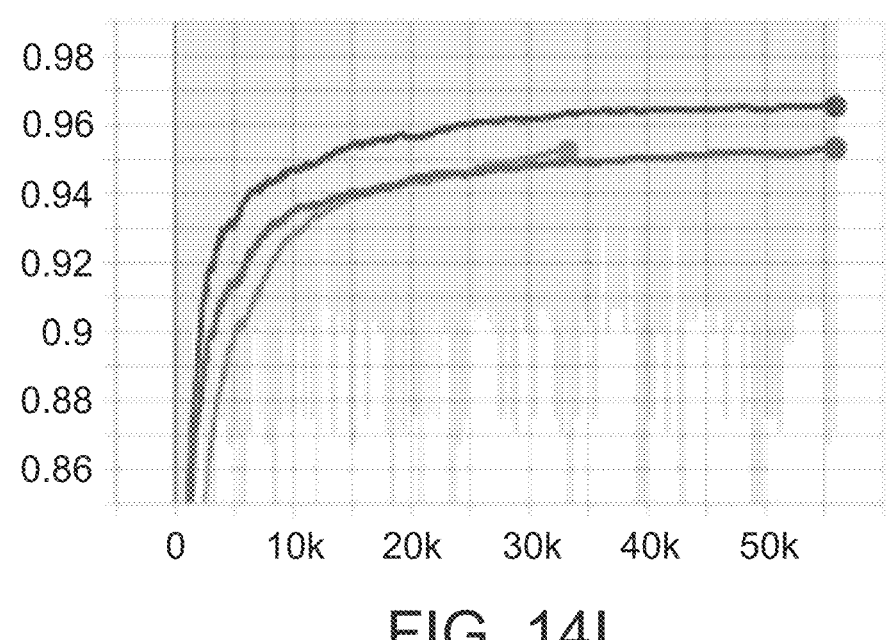
Figure 14J:
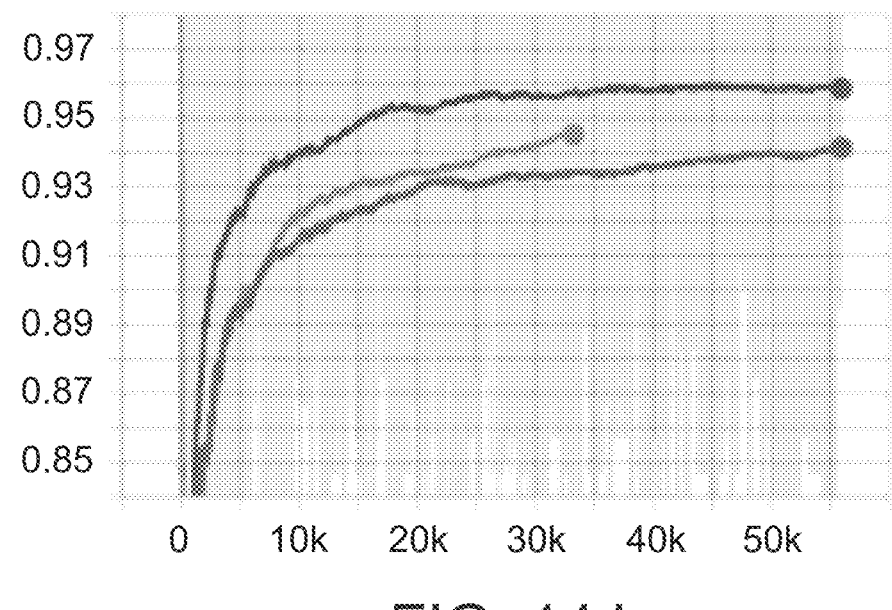
Figure 14K:
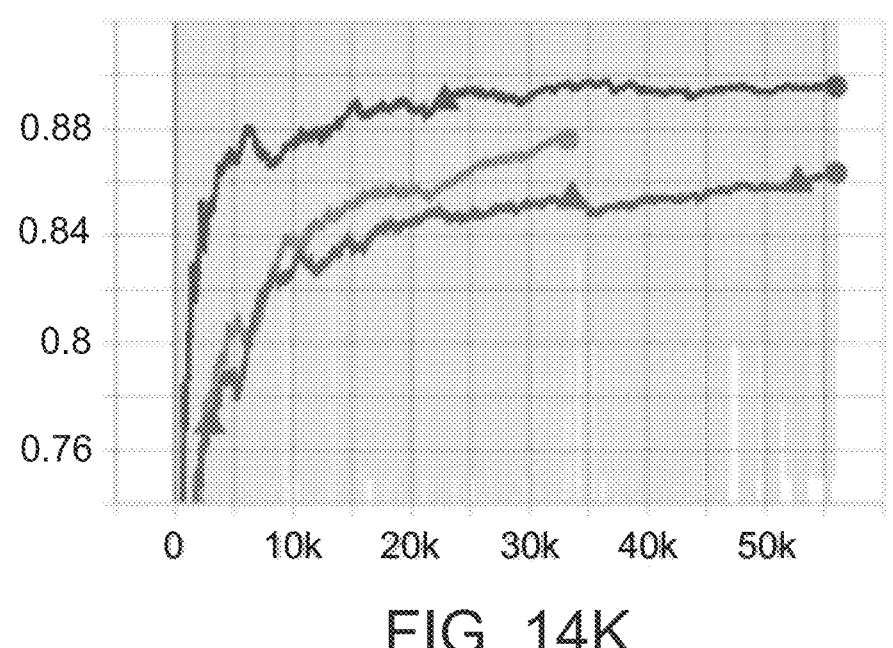
Figure 14L:
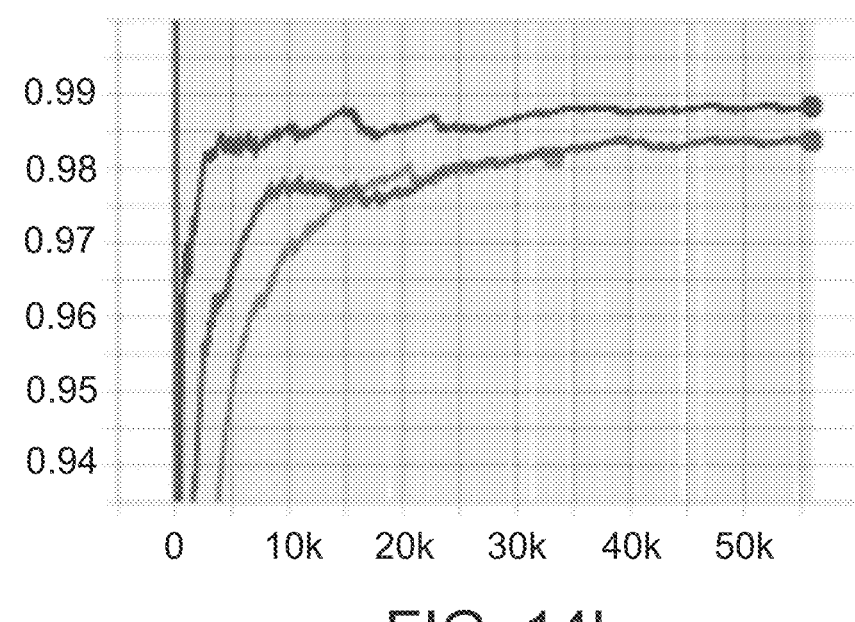
Figure 14M:
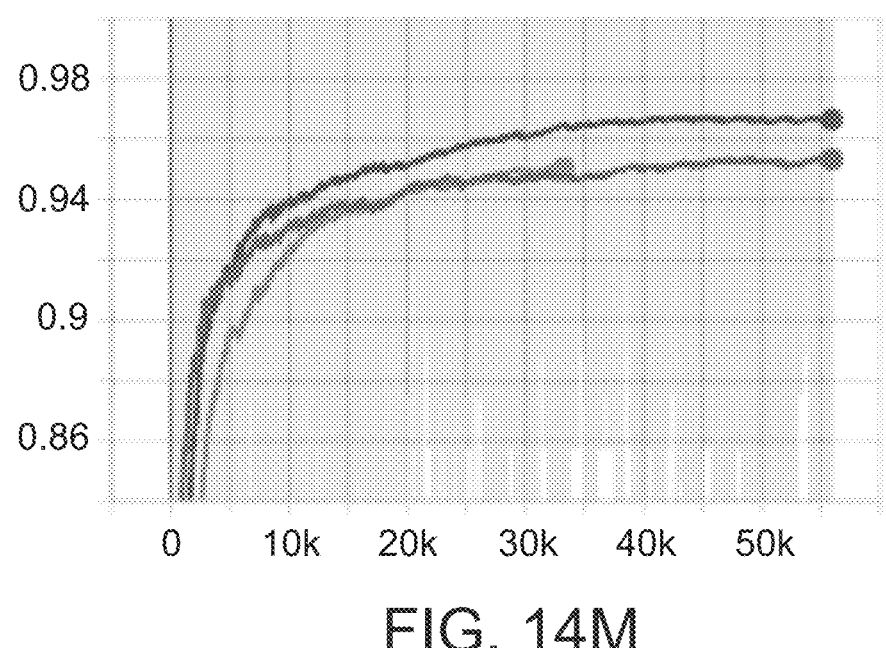
Figure 14N:
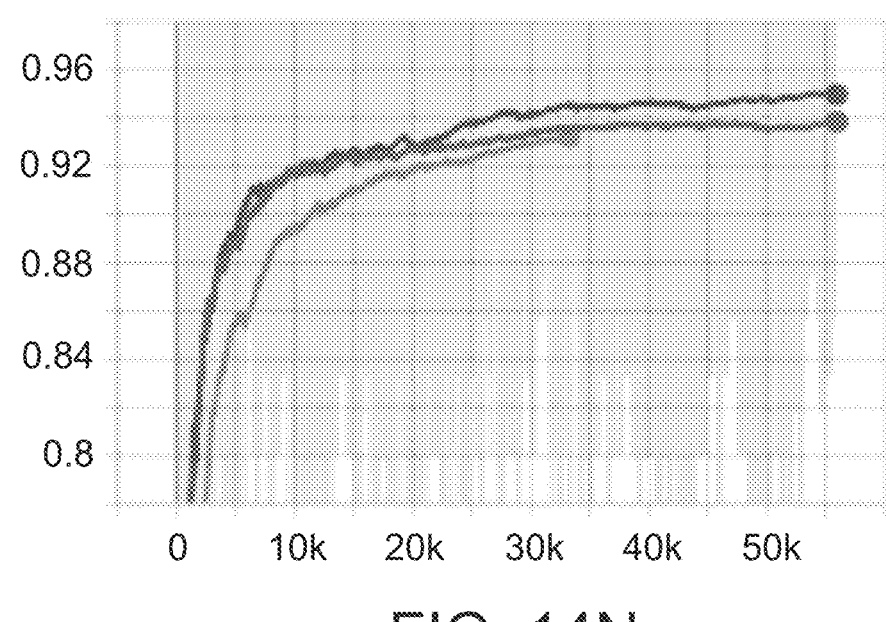
Figure 14O:
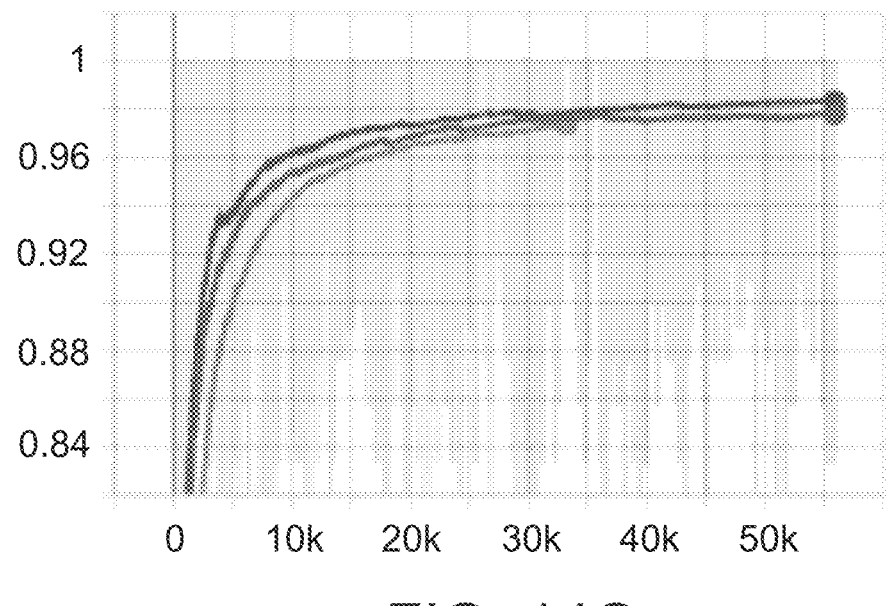
Figure 14P:
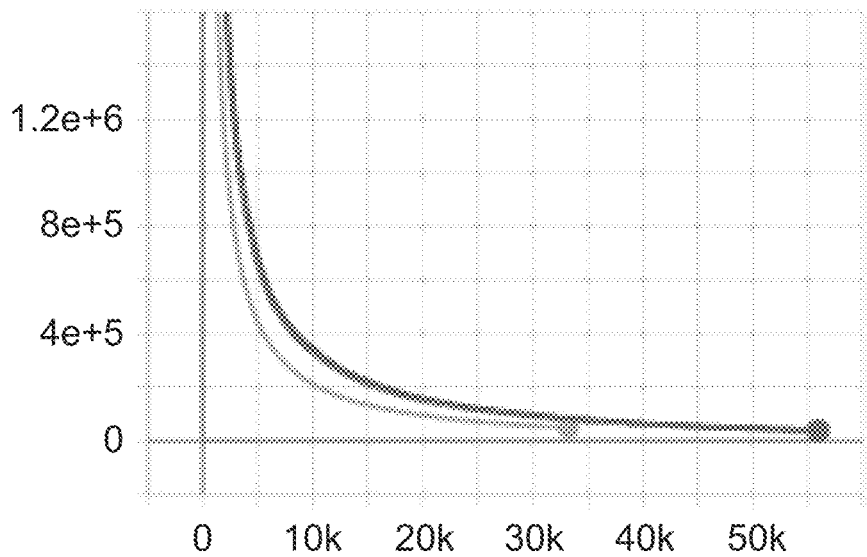

FIGS. 14A-P show results obtained using a model in which the parental information includes only their genotype, with no read-level or nucleotide-level information. The results for these representations of the data are shown in FIGS. 13A-P, for the one-hot (blue), group-hot (light blue)

representations, and for the case (pink) in which the only parental information that was used was the parental genotypes (homozygous to the reference or alternate allele, or heterozygous). Accuracy and loss are presented for the same groups as in FIGS. 12A-P.

FIGS. 14A-P demonstrate that high accuracy is obtained even by using only the parental genotypes. This means that it is not necessary to sequence the parents using NGS, and that other technologies can suffice. Yet, read- and nucleotide-level information from NGS appears to improve the results.

ANNEX 1

TABLE A.1

| Features used in the machine learning models. | | |
| --- | --- | --- |
| Name | Source | Description |
| CHROM | cfDNA preprocessing (Freebayes) | Chromose |
| POS | cfDNA preprocessing (Freebayes) | Start position |
| REF | cfDNA preprocessing (Freebayes) | Reference allele |
| ALT | cfDNA preprocessing (Freebayes) | Alternate allele |
| GT | Hoobari | Genotype |
| DP | cfDNA preprocessing (Freebayes) | Read Depth |
| AD | cfDNA preprocessing (Freebayes) | Number of observation for each allele |
| RO | cfDNA preprocessing (Freebayes) | Reference allele observation count |
| QR | cfDNA preprocessing (Freebayes) | Sum of quality of the reference observations |
| AO | cfDNA preprocessing (Freebayes) | Alternate allele observation count |
| QA | cfDNA preprocessing (Freebayes) | Sum of quality of the alternate observations |
| QUAL | Hoobari | Fetal prediction QUAL score |
| GL | Hoobari | Genotype Likelihood, log10-scaled likelihoods of the data given the called genotype for each possible genotype generated from the reference and alternate alleles given the sample ploidy |
| PG | Hoobari | P(Genotype), Per-site genotype prior probabilities |
| PP | Hoobari | P(Posterior), Per-site genotype posterior probabilities |
| MGT | Parental variant calling (Freebayes) | Mother's Genotype |
| MGQ | Parental variant calling (Freebayes) | Mother's Genotype Quality, the Phred-scaled marginal (or unconditional) probability of the called genotype |
| MGL | Parental variant calling (Freebayes) | Mother's Genotype Likelihood, log10-scaled likelihoods of the data given the called genotype for each possible genotype generated from the reference and alternate alleles given the sample ploidy |
| MAD | Parental variant calling (Freebayes) | Mother's Number of observation for each allele |
| MDP | Parental variant calling (Freebayes) | Mother's Read Depth |
| MRO | Parental variant calling (Freebayes) | Mother's Reference allele observation count |
| MQR | Parental variant calling (Freebayes) | Mother's Sum of quality of the reference observations |
| MAO | Parental variant calling (Freebayes) | Mother's Alternate allele observation count |
| MQA | Parental variant calling (Freebayes) | Mother's Sum of quality of the alternate observations |
| FGT | Parental variant calling (Freebayes) | Father's Genotype |
| FGQ | Parental variant calling (Freebayes) | Father's Genotype Quality, the Phred-scaled marginal (or unconditional) probability of the called genotype |

TABLE A.1-continued

Features used in the machine learning models.

| Name | Source | Description |
|------|--------|-------------|
| FGL | Parental variant calling (Freebayes) | Father's Genotype Likelihood, log10-scaled likelihoods of the data given the called genotype for each possible genotype generated from the reference and alternate alleles given the sample ploidy |
| FAD | Parental variant calling (Freebayes) | Father's Number of observation for each allele |
| FDP | Parental variant calling (Freebayes) | Father's Read Depth |
| FRO | Parental variant calling (Freebayes) | Father's Reference allele observation count |
| FQR | Parental variant calling (Freebayes) | Father's Sum of quality of the reference observations |
| FAO | Parental variant calling (Freebayes) | Father's Alternate allele observation count |
| FQA | Parental variant calling (Freebayes) | Father's Sum of quality of the alternate observations |
| MFQ | Parental variant calling (Freebayes) | Mother's and Father's QUAL score from the parental vcf |
| NS | cfDNA preprocessing (Freebayes) | Number of samples with data |
| DP | cfDNA preprocessing (Freebayes) | Total read depth at the locus |
| DPB | cfDNA preprocessing (Freebayes) | Total read depth per bp at the locus; bases in reads overlapping/bases in haplotype |
| AC | cfDNA preprocessing (Freebayes) | Total number of alternate alleles in called genotypes |
| AN | cfDNA preprocessing (Freebayes) | Total number of alleles in called genotypes |
| AF | cfDNA preprocessing (Freebayes) | Estimated allele frequency in the range (0, 1] |
| RO | cfDNA preprocessing (Freebayes) | Count of full observations of the reference haplotype. |
| AO | cfDNA preprocessing (Freebayes) | Count of full observations of this alternate haplotype. |
| PRO | cfDNA preprocessing (Freebayes) | Reference allele observation count, with partial observations recorded fractionally |
| PAO | cfDNA preprocessing (Freebayes) | Alternate allele observations, with partial observations recorded fractionally |
| QR | cfDNA preprocessing (Freebayes) | Reference allele quality sum in phred |
| QA | cfDNA preprocessing (Freebayes) | Alternate allele quality sum in phred |
| PQR | cfDNA preprocessing (Freebayes) | Reference allele quality sum in phred for partial observations |
| PQA | cfDNA preprocessing (Freebayes) | Alternate allele quality sum in phred for partial observations |
| SRF | cfDNA preprocessing (Freebayes) | Number of reference observations on the forward strand |
| SRR | cfDNA preprocessing (Freebayes) | Number of reference observations on the reverse strand |
| SAF | cfDNA preprocessing (Freebayes) | Number of alternate observations on the forward strand |
| SAR | cfDNA preprocessing (Freebayes) | Number of alternate observations on the reverse strand |
| SRP | cfDNA preprocessing (Freebayes) | Strand balance probability for the reference allele: Phred-scaled upper-bounds estimate of the probability of observing the deviation between SRF and SRR given E(SRF/SRR) ~0.5, derived using Hoeffding's inequality |
| SAP | cfDNA preprocessing (Freebayes) | Strand balance probability for the alternate allele: Phred-scaled upper-bounds estimate of the probability of observing the deviation between SAF and SAR given E(SAF/SAR) ~0.5, derived using Hoeffding's inequality |
| AB | cfDNA preprocessing (Freebayes) | Allele balance at heterozygous sites: a number between 0 and 1 representing the ratio of reads showing the reference allele to all reads, considering only reads from individuals called as heterozygous |
| ABP | cfDNA preprocessing (Freebayes) | Allele balance probability at heterozygous sites: Phred-scaled upper-bounds estimate of the probability of observing the deviation between ABR and ABA given E(ABR/ABA) ~0.5, derived using Hoeffding's inequality |

TABLE A.1-continued

Features used in the machine learning models.

| Name | Source | Description |
| --- | --- | --- |
| RUN | cfDNA preprocessing (Freebayes) | Run length: the number of consecutive repeats of the alternate allele in the reference genome |
| RPP | cfDNA preprocessing (Freebayes) | Read Placement Probability: Phred-scaled upper-bounds estimate of the probability of observing the deviation between RPL and RPR given E(RPL/RPR) ~0.5, derived using Hoeffding's inequality |
| RPPR | cfDNA preprocessing (Freebayes) | Read Placement Probability for reference observations: Phred-scaled upper-bounds estimate of the probability of observing the deviation between RPL and RPR given E(RPL/RPR) ~0.5, derived using Hoeffding's inequality |
| RPL | cfDNA preprocessing (Freebayes) | Reads Placed Left: number of reads supporting the alternate balanced to the left (5') of the alternate allele |
| RPR | cfDNA preprocessing (Freebayes) | Reads Placed Right: number of reads supporting the alternate balanced to the right (3') of the alternate allele |
| EPP | cfDNA preprocessing (Freebayes) | End Placement Probability: Phred-scaled upper-bounds estimate of the probability of observing the deviation between EL and ER given E(EL/ER) ~0.5, derived using Hoeffding's inequality |
| EPPR | cfDNA preprocessing (Freebayes) | End Placement Probability for reference observations: Phred-scaled upper-bounds estimate of the probability of observing the deviation between EL and ER given E(EL/ER) ~0.5, derived using Hoeffding's inequality |
| DPRA | cfDNA preprocessing (Freebayes) | Alternate allele depth ratio. Ratio between depth in samples with each called alternate allele and those without. |
| ODDS | cfDNA preprocessing (Freebayes) | The log odds ratio of the best genotype combination to the second-best. |
| GTI | cfDNA preprocessing (Freebayes) | Number of genotyping iterations required to reach convergence or bailout. |
| TYPE | cfDNA preprocessing (Freebayes) | The type of allele, either snp, mnp, ins, del, or complex. |
| CIGAR | cfDNA preprocessing (Freebayes) | The extended CIGAR representation of each alternate allele, with the exception that '=' is replaced by 'M' to ease VCF parsing. Note that INDEL alleles do not have the first matched base (which is provided by default, per the spec) referred to by the CIGAR. |
| NUMALT | cfDNA preprocessing (Freebayes) | Number of unique non-reference alleles in called genotypes at this position. |
| MEANALT | cfDNA preprocessing (Freebayes) | Mean number of unique non-reference allele observations per sample with the corresponding alternate alleles. |
| LEN | cfDNA preprocessing (Freebayes) | allele length |
| MQM | cfDNA preprocessing (Freebayes) | Mean mapping quality of observed alternate alleles |
| MQMR | cfDNA preprocessing (Freebayes) | Mean mapping quality of observed reference alleles |
| PAIRED | cfDNA preprocessing (Freebayes) | Proportion of observed alternate alleles which are supported by properly paired read fragments |
| PAIREDR | cfDNA preprocessing (Freebayes) | Proportion of observed reference alleles which are supported by properly paired read fragments |
| MIN_DP | cfDNA preprocessing (Freebayes) | Minimum depth in gVCF output block. |
| END | cfDNA preprocessing (Freebayes) | Last position (inclusive) in gVCF output record. |
| technology.ILLUMINA | cfDNA preprocessing (Freebayes) | Fraction of observations supporting the alternate observed in reads from ILLUMINA |
| PNS | Parental variant calling (Freebayes) | Parents Number of samples with data |
| PDP | Parental variant calling (Freebayes) | Parents Total read depth at the locus |
| PDPB | Parental variant calling (Freebayes) | Parents Total read depth per bp at the locus; bases in reads overlapping/bases in haplotype |

TABLE A.1-continued

| Name | Source | Description |
| --- | --- | --- |
| PAC | Parental variant calling (Freebayes) | Parents Total number of alternate alleles in called genotypes |
| PAN | Parental variant calling (Freebayes) | Parents Total number of alleles in called genotypes |
| PAF | Parental variant calling (Freebayes) | Parents Estimated allele frequency in the range (0, 1] |
| PRO | Parental variant calling (Freebayes) | Parents Reference allele observation count, with partial observations recorded fractionally |
| PAO | Parental variant calling (Freebayes) | Parents Alternate allele observations, with partial observations recorded fractionally |
| PPRO | Parental variant calling (Freebayes) | Parents Reference allele observation count, with partial observations recorded fractionally |
| PPAO | Parental variant calling (Freebayes) | Parents Alternate allele observations, with partial observations recorded fractionally |
| PQR | Parental variant calling (Freebayes) | Parents Reference allele quality sum in phred |
| PQA | Parental variant calling (Freebayes) | Parents Alternate allele quality sum in phred |
| PPQR | Parental variant calling (Freebayes) | Parents Reference allele quality sum in phred for partial observations |
| PPQA | Parental variant calling (Freebayes) | Parents Alternate allele quality sum in phred for partial observations |
| PSRF | Parental variant calling (Freebayes) | Parents Number of reference observations on the forward strand |
| PSRR | Parental variant calling (Freebayes) | Parents Number of reference observations on the reverse strand |
| PSAF | Parental variant calling (Freebayes) | Parents Number of alternate observations on the forward strand |
| PSAR | Parental variant calling (Freebayes) | Parents Number of alternate observations on the reverse strand |
| PSRP | Parental variant calling (Freebayes) | Parents Strand balance probability for the reference allele: Phred-scaled upper-bounds estimate of the probability of observing the deviation between SRF and SRR given E(SRF/SRR) ~0.5, derived using Hoeffding's inequality |
| PSAP | Parental variant calling (Freebayes) | Parents Strand balance probability for the alternate allele: Phred-scaled upper-bounds estimate of the probability of observing the deviation between SAF and SAR given E(SAF/SAR) ~0.5, derived using Hoeffding's inequality |
| PAB | Parental variant calling (Freebayes) | Parents Allele balance at heterozygous sites: a number between 0 and 1 representing the ratio of reads showing the reference allele to all reads, considering only reads from individuals called as heterozygous |
| PABP | Parental variant calling (Freebayes) | Parents Allele balance probability at heterozygous sites: Phred-scaled upper-bounds estimate of the probability of observing the deviation between ABR and ABA given E(ABR/ABA) ~0.5, derived using Hoeffding's inequality |
| PRUN | Parental variant calling (Freebayes) | Parents Run length: the number of consecutive repeats of the alternate allele in the reference genome |
| PRPP | Parental variant calling (Freebayes) | Parents Read Placement Probability: Phred-scaled upper-bounds estimate of the probability of observing the deviation between RPL and RPR given E(RPL/RPR) ~0.5, derived using Hoeffding's inequality |
| PRPPR | Parental variant calling (Freebayes) | Parents Read Placement Probability for reference observations: Phred-scaled upper-bounds estimate of the probability of observing the deviation between RPL and RPR given E(RPL/RPR) ~0.5, derived using Hoeffding's inequality |
| PRPL | Parental variant calling (Freebayes) | Parents Reads Placed Left: number of reads supporting the alternate balanced to the left (5') of the alternate allele |

TABLE A.1-continued

Features used in the machine learning models.

| Name | Source | Description |
|------|--------|-------------|
| PRPR | Parental variant calling (Freebayes) | Parents Reads Placed Right: number of reads supporting the alternate balanced to the right (3') of the alternate allele |
| PEPP | Parental variant calling (Freebayes) | Parents End Placement Probability: Phred-scaled upper-bounds estimate of the probability of observing the deviation between EL and ER given E(EL/ER) ~0.5, derived using Hoeffding's inequality |
| PRPPR | Parental variant calling (Freebayes) | Parents Read Placement Probability for reference observations: Phred-scaled upper-bounds estimate of the probability of observing the deviation between RPL and RPR given E(RPL/RPR) ~0.5, derived using Hoeffding's inequality |
| PRPL | Parental variant calling (Freebayes) | Parents Reads Placed Left: number of reads supporting the alternate balanced to the left (5') of the alternate allele |
| PRPR | Parental variant calling (Freebayes) | Parents Reads Placed Right: number of reads supporting the alternate balanced to the right (3') of the alternate allele |
| PEPP | Parental variant calling (Freebayes) | Parents End Placement Probability: Phred-scaled upper-bounds estimate of the probability of observing the deviation between EL and ER given E(EL/ER) ~0.5, derived using Hoeffding's inequality |
| PEPPR | Parental variant calling (Freebayes) | Parents End Placement Probability for reference observations: Phred-scaled upper-bounds estimate of the probability of observing the deviation between EL and ER given E(EL/ER) ~0.5, derived using Hoeffding's inequality |
| PDPRA | Parental variant calling (Freebayes) | Parents Alternate allele depth ratio. Ratio between depth in samples with each called alternate allele and those without. |
| PODDS | Parental variant calling (Freebayes) | Parents The log odds ratio of the best genotype combination to the second-best. |
| PGTI | Parental variant calling (Freebayes) | Parents Number of genotyping iterations required to reach convergence or bailout. |
| PTYPE | Parental variant calling (Freebayes) | Parents The type of allele, either snp, mnp, ins, del, or complex. |
| PCIGAR | Parental variant calling (Freebayes) | Parents The extended CIGAR representation of each alternate allele, with the exception that '=' is replaced by 'M' to ease VCF parsing. Note that INDEL alleles do not have the first matched base (which is provided by default, per the spec) referred to by the CIGAR. |
| PNUMALT | Parental variant calling (Freebayes) | Parents Number of unique non-reference alleles in called genotypes at this position. |
| PMEANALT | Parental variant calling (Freebayes) | Parents Mean number of unique non-reference allele observations per sample with the corresponding alternate alleles. |
| PLEN | Parental variant calling (Freebayes) | Parents allele length |
| PMQM | Parental variant calling (Freebayes) | Parents Mean mapping quality of observed alternate alleles |
| PMQMR | Parental variant calling (Freebayes) | Parents Mean mapping quality of observed reference alleles |
| PPAIRED | Parental variant calling (Freebayes) | Parents Proportion of observed alternate alleles which are supported by properly paired read fragments |
| PPAIREDR | Parental variant calling (Freebayes) | Parents Proportion of observed reference alleles which are supported by properly paired read fragments |
| PMIN | Parental variant calling (Freebayes) | Parents Minimum depth in gVCF output block. |
| PEND | Parental variant calling (Freebayes) | Parents Last position (inclusive) in gVCF output record. |
| Ptechnology.ILLUMINA | Parental variant calling (Freebayes) | Parents Fraction of observations supporting the alternate observed in reads from ILLUMINA |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

REFERENCES

1. Lo, Y. M. D. et al. Digital PCR for the molecular detection of fetal chromosomal aneuploidy. Proc. Natl. Acad. Sci. 104, 13116-13121 (2007).
2. Fan, H. C., Blumenfeld, Y. J., Chitkara, U., Hudgins, L. & Quake, S. R. Noninvasive diagnosis of fetal aneuploidy by shotgun sequencing DNA from maternal blood. Proc. Natl. Acad. Sci. U.S.A. 105, 16266-16271 (2008).
3. Hill, M., Compton, C., Lewis, C., Skirton, H. & Chitty, L. S. Determination of fetal sex in pregnancies at risk of haemophilia: a qualitative study exploring the clinical practices and attitudes of health professionals in the United Kingdom. Haemophilia 18, 575-583 (2012).
4. Lewis, C., Hill, M., Skirton, H. & Chitty, L. S. Non-invasive prenatal diagnosis for fetal sex determination: benefits and disadvantages from the service users' perspective. Eur. J. Hum. Genet. EJHG 20, 1127-1133 (2012).
5. Finning, K., Martin, P. & Daniels, G. A clinical service in the UK to predict fetal Rh (Rhesus) D blood group using free fetal DNA in maternal plasma. Ann. N. Y. Acad. Sci. 1022, 119-123 (2004).
6. Minon. J.-M., Gerard. C., Senterre. J.-M., Schaaps. J.-P. & Foidart. J.-M. Routine fetal RHD genotyping with maternal plasma: a four-year experience in Belgium. Transfusion (Paris) 48, 373-381 (2008).
7. Mahdieh, N. & Rabbani, B. An Overview of Mutation Detection Methods in Genetic Disorders. Iran. J. Pediatr. 23, 375-388 (2013).
8. Yang, Y. et al. Clinical Whole-Exome Sequencing for the Diagnosis of Mendelian Disorders. N. Engl. J. Med. 369, 1502-1511 (2013).
9. Isakov, O., Perrone, M. & Shomron, N. Exome sequencing analysis: a guide to disease variant detection. Methods Mol. Biol. Clifton NJ 1038, 137-158 (2013).
10. Meng, L. et al. Use of Exome Sequencing for Infants in Intensive Care Units: Ascertainment of Severe Single-Gene Disorders and Effect on Medical Management. JAMA Pediatr. 171, e173438-e173438 (2017).
11. Mackie, F. L., Carss, K. J., Hillman, S. C., Hurles, M. E. & Kilby, M. D. Exome Sequencing in Fetuses with Structural Malformations. J. Clin. Med. 3, 747-762 (2014).
12. Vora, N. L. et al. Prenatal exome sequencing in anomalous fetuses: new opportunities and challenges. Genet. Med. 19, 1207 (2017).
13. Kitzman, J. O. et al. Noninvasive whole-genome sequencing of a human fetus. Sci. Transl. Med. 4, 137ra76 (2012).
14. Fan, H. C. et al. Non-invasive prenatal measurement of the fetal genome. Nature 487, 320-324 (2012).
15. Hill, M. et al. Non-invasive prenatal diagnosis for cystic fibrosis: detection of paternal mutations, exploration of patient preferences and cost analysis. Prenat. Diagn. 35, 950-958 (2015).
16. Lun. F. M. F. et al. Noninvasive prenatal diagnosis of monogenic diseases by digital size selection and relative mutation dosage on DNA in maternal plasma. Proc. Natl. Acad. Sci. U.S.A. 105, 19920-19925 (2008).
17. Lam, K.-W. G. et al. Noninvasive Prenatal Diagnosis of Monogenic Diseases by Targeted Massively Parallel Sequencing of Maternal Plasma: Application to β-Thalassemia. Clin. Chem. 58, 1467-1475 (2012).
18. Lo, Y. M. D. et al. Maternal Plasma DNA Sequencing Reveals the Genome-Wide Genetic and Mutational Profile of the Fetus. Sci. Transl. Med. 2, 61ra91-61ra91 (2010).
19. Chen, S. et al. Haplotype-assisted accurate non-invasive fetal whole genome recovery through maternal plasma sequencing. Genome Med. 5, 18 (2013).
20. Chan, K. C. A. et al. Second generation noninvasive fetal genome analysis reveals de novo mutations, single-base parental inheritance, and preferred DNA ends. Proc. Natl. Acad. Sci. 201615800 (2016). doi: 10.1073/pnas.1615800113
21. Snyder, M. W. et al. Noninvasive fetal genome sequencing: a primer. Prenat. Diagn. 33, 547-554 (2013).
22. Snyder, M. W., Adey, A., Kitzman, J. O. & Shendure, J. Haplotype-resolved genome sequencing: experimental methods and applications. Nat. Rev. Genet. 16, 344-358 (2015).
23. Jenkins, L. A., Deans, Z. C., Lewis, C. & Allen, S. Delivering an accredited non-invasive prenatal diagnosis service for monogenic disorders, and recommendations for best practice. Prenat. Diagn. (2017). doi: 10.1002/pd.5197
24. Chan, K. C. A. et al. Size distributions of maternal and fetal DNA in maternal plasma. Clin. Chem. 50, 88-92 (2004).
25. Fan, H. C., Blumenfeld, Y. J., Chitkara, U., Hudgins, L. & Quake, S. R. Analysis of the Size Distributions of Fetal and Maternal Cell-Free DNA by Paired-End Sequencing. Clin. Chem. 56, 1279-1286 (2010).
26. Yu, S. C. Y. et al. Size-based molecular diagnostics using plasma DNA for noninvasive prenatal testing. Proc. Natl. Acad. Sci. 111, 8583-8588 (2014).
27. Cirigliano, V., Ordoñez, E., Rueda, L., Syngelaki, A. & Nicolaides, K. H. Performance of the neoBona test: a new paired-end massively parallel shotgun sequencing approach for cell-free DNA-based aneuploidy screening. Ultrasound Obstet. Gynecol. 49, 460-464 (2017).
28. Sun, K. et al. COFFEE: control-free noninvasive fetal chromosomal examination using maternal plasma DNA. Prenat. Diagn. 37, 336-340 (2017).
29. Sillence. K. Cell-free fetal DNA (cffDNA) enrichment for non-invasive prenatal testing (NIPT): a comparison of molecular techniques. (2016).
30. Mullaney, J. M., Mills, R. E., Pittard, W. S. & Devine, S. E. Small insertions and deletions (INDELs) in human genomes. Hum. Mol. Genet. 19, R131-R136 (2010).

31. Neuman, J. A., Isakov, O. & Shomron, N. Analysis of insertion-deletion from deep-sequencing data: software evaluation for optimal detection. Brief. Bioinform. 14, 46-55 (2013).

32. Jiang, Y., Turinsky, A. L. & Brudno, M. The missing indels: an estimate of indel variation in a human genome and analysis of factors that impede detection. Nucleic Acids Res. 43, 7217-7228 (2015).

33. Hwang, S., Kim, E., Lee, I. & Marcotte, E. M. Systematic comparison of variant calling pipelines using gold standard personal exome variants. Sci. Rep. 5, 17875 (2015).

34. Li. H. & Durbin. R. Fast and accurate short read alignment with Burrows-Wheeler transform. Bioinformatics 25, 1754-1760 (2009).

35. Garrison, E. & Marth, G. Haplotype-based variant detection from short-read sequencing. ArXiv12073907 Q-Bio (2012).

36. Danecek, P. et al. The variant call format and VCFtools. Bioinformatics 27, 2156-2158 (2011).

37. Sequence Alignment/Map format specification, May 22, 2018, www(dot)samtools(dot)github(dot)io/hts-specs/SAMv1(dot)pdf.

38. Chan K C A, Jiang P, Sun K, Cheng Y K Y, Tong Y K, Cheng S H, Wong A I C, Hudecova I, Leung T Y, Chiu R W K, et al. 2016. Second generation noninvasive fetal genome analysis reveals de novo mutations, single-base parental inheritance, and preferred DNA ends. Proc Natl Acad Sci 201615800.

39. Fan H C, Gu W. Wang J. Blumenfeld Y J, El-Sayed Y Y, Quake S R. 2012.

Noninvasive Prenatal Measurement of the Fetal Genome. Nature 487:320-324.

40. Kitzman J O, Snyder M W, Ventura M, Lewis A P, Qiu R, Simmons L E, Gammill H S, Rubens C E, Santillan D A, Murray J C, et al. 2012. Noninvasive whole-genome sequencing of a human fetus. Sci Transl Med 4: 137ra76.

41. Luo R, Sedlazeck F J, Lam T-W, Schatz M. 2018. Clairvoyante: a multi-task convolutional deep neural network for variant calling in Single Molecule Sequencing. bioRxiv 310458.

42. Poplin R, Chang P-C, Alexander D, Schwartz S, Colthurst T, Ku A, Newburger D, Dijamco J, Nguyen N, Afshar P T, et al. 2018. Creating a universal SNP and small indel variant caller with deep neural networks. bioRxiv 092890.

43. Torracinta R, Campagne F. 2016. Training Genotype Callers with Neural Networks. bioRxiv 097469.

What is claimed is:

1. A method of determining whether a fetus possesses a genetic or congenital disease, comprising:

obtaining a plurality of nucleic acid molecules from a biological sample of a pregnant mother and a biological sample of a father of a pair parenting a fetus;

obtaining maternal genomic DNA (gDNA) sequencing data, maternal cell-free DNA (cfDNA) sequencing data, and paternal gDNA sequencing data of said plu-
rality of nucleic acid molecules using deep next generation sequencing (NGS) of the whole genome or the whole exome;

analyzing said data to identify a first set of sites at which the parents are homozygous for different alleles, and a second set of sites at which at least one of the parents has a mutation associated with a genetic disease, wherein said analyzing comprises identifying in reads covering said first set of sites a first group of reads including only reads that present paternal alleles but no other reads, and a second group including all other reads, and wherein said analyzing is executed by a variant caller;

for each site of said first set, determining a probability that a respective portion of said maternal cfDNA data is derived from said fetus, wherein said determining said probability is based on differences between reads in said first group and reads in said second group in the read fragment size;

classifying each site of said second set according to said probabilities as being either fetal or maternal to genotype said fetus, wherein said classifying comprises calculating a total fetal fraction, constructing a fetal size distribution and a maternal size distribution, binning said fetal size distribution, calculating a fetal fraction for each fragment size bin, wherein said classifying comprises applying a Bayesian procedure, said applying Bayesian procedure comprising using the maternal and/or paternal gDNA sequencing data to calculate each fragment's probability for being fetal, based on the read fragment size, calculating, for at least one site of said second set and at least one fragment at said at least one site, a probability that said fragment is fetal, based on a fetal fraction of a respective fragment size bin to which said fragment belongs, and extracting the genotype at each site that is classified as fetal to genotype said fetus; and only if said genotyping identifies that the fetus possesses a mutation associated with a genetic or congenital disease:

(i) administering a prenatal or a post-natal treatment for said genetic or congenital disease in an amount effective to prevent or treat said disease, wherein said treatment comprises pharmaceutical based intervention, surgery, genetic therapy, nutritional therapy, or combinations thereof; or (ii) performing a pregnancy termination.

2. The method according to claim 1, wherein said classifying comprises applying a machine learning procedure to said identified sites to genotype said fetus, wherein said applying a machine learning procedure comprises feeding a trained machine learning program with maternal gDNA sequencing data, maternal cfDNA sequencing data, and paternal gDNA sequencing data, wherein the output of the trained machine learning program is classification of sites at which at least one of the parents has a mutation associated with a genetic or congenital disease as being either fetal or maternal; and wherein the training of the machine learning program comprises feeding the machine learning training program with maternal gDNA sequencing data, maternal cfDNA sequencing data, paternal gDNA sequencing data and fetal gDNA sequencing data for each of a cohort of subjects parenting a genotyped fetus.

3. The method according to claim 1, wherein said genetic or congenital disease is a single-gene disorder (SGD) of paternal origin.

4. The method according to claim 1, wherein said genetic or congenital disease is a single-gene disorder (SGD) of maternal origin.

5. The method according to claim 1, wherein said genetic or congenital disease is characterized by inherited insertions-deletions.

6. The method according to claim 1, wherein said genetic or congenital disease is characterized by chromosomal abnormality.

7. The method according to claim 1, wherein said genetic or congenital disease is a monogenic disease.

8. The method according to claim 1, wherein said genetic or congenital disease is a multigenic disease.

9. A computer software product, comprising a non-transitory computer readable storage medium in which program instructions are stored, which instructions, when read by a data processor, cause the data processor to receive maternal cfDNA data and paternal cfDNA data of a pair parenting to a fetus and to execute a method of determining whether a fetus possesses a genetic or congenital disease, said method comprising:

obtaining a plurality of nucleic acid molecules from a biological sample of a pregnant mother and a biological sample of a father of a pair parenting a fetus;

obtaining maternal genomic DNA (DNA) sequencing data, maternal cell-free DNA (cfDNA) sequencing data, and paternal gDNA sequencing data of said plurality of nucleic acid molecules using deep next generation sequencing (NGS) of the whole genome or the whole exome;

analyzing said data to identify a first set of sites at which the parents are homozygous for different alleles, and a second set of sites at which at least one of the parents has a mutation associated with a genetic disease, wherein said analyzing comprises identifying in reads covering said first set of sites a first group of reads including only reads that present paternal alleles but no other reads, and a second group including all other reads, and wherein said analyzing is executed by a variant caller;

for each site of said first set, determining a probability that a respective portion of said maternal cfDNA data is derived from said fetus, wherein said determining said probability is based on differences between reads in said first group and reads in said second group in the read fragment size;

classifying each site of said second set according to said probabilities as being either fetal or maternal to genotype said fetus, wherein said classifying comprises calculating a total fetal fraction, constructing a fetal size distribution and a maternal size distribution, binning said fetal size distribution, calculating a fetal fraction for each fragment size bin, wherein said classifying comprises applying a Bayesian procedure, said applying Bayesian procedure comprising using the maternal and/or paternal gDNA sequencing data to calculate each fragment's probability for being fetal, based on the read fragment size, calculating, for at least one site of said second set and at least one fragment at said at least one site, a probability that said fragment is fetal, based on a fetal fraction of a respective fragment size bin to which said fragment belongs, and extracting the genotype at each site that is classified as fetal to genotype said fetus; and only if said genotyping identifies that the fetus possesses a mutation associated with a genetic or congenital disease:

(i) administering a prenatal or a post-natal treatment for said genetic or congenital disease in an amount effective to prevent or treat said disease, wherein said treatment comprises pharmaceutical based intervention, surgery, genetic therapy, nutritional therapy, or combinations thereof; or (ii) performing a pregnancy termination.

10. A system for fetal genotyping, comprising: an input circuit receiving maternal cell-free DNA (cfDNA) data and paternal (cfDNA) data of a pair parenting to a fetus; a data processor configured for analyzing said data to identify sites at which the parents are homozygous for executing a method of determining whether a fetus possesses a genetic or congenital disease, said method comprising:

obtaining a plurality of nucleic acid molecules from a biological sample of a pregnant mother and a biological sample of a father of a pair parenting a fetus;

obtaining maternal genomic DNA (gDNA) sequencing data, maternal cell-free DNA (cfDNA) sequencing data, and paternal gDNA sequencing data of said plurality of nucleic acid molecules using deep next generation sequencing (NGS) of the whole genome or the whole exome;

analyzing said data to identify a first set of sites at which the parents are homozygous for different alleles, and a second set of sites at which at least one of the parents has a mutation associated with a genetic disease, wherein said analyzing comprises identifying in reads covering said first set of sites a first group of reads including only reads that present paternal alleles but no other reads, and a second group including all other reads, and wherein said analyzing is executed by a variant caller;

for each site of said first set, determining a probability that a respective portion of said maternal cfDNA data is derived from said fetus, wherein said determining said probability is based on differences between reads in said first group and reads in said second group in the read fragment size;

classifying each site of said second set according to said probabilities as being either fetal or maternal to genotype said fetus, wherein said classifying comprises calculating a total fetal fraction, constructing a fetal size distribution and a maternal size distribution, binning said fetal size distribution, calculating a fetal fraction for each fragment size bin, wherein said classifying comprises applying a Bayesian procedure, said applying Bayesian procedure comprising using the maternal and/or paternal gDNA sequencing data to calculate each fragment's probability for being fetal, based on the read fragment size, calculating, for at least one site of said second set and at least one fragment at said at least one site, a probability that said fragment is fetal, based on a fetal fraction of a respective fragment size bin to which said fragment belongs, and extracting the genotype at each site that is classified as fetal to genotype said fetus; and only if said genotyping identifies that the fetus possesses a mutation associated with a genetic or congenital disease:

(i) administering a prenatal or a post-natal treatment for said genetic or congenital disease in an amount effective to prevent or treat said disease, wherein said treatment comprises pharmaceutical based intervention, surgery, genetic therapy, nutritional therapy, or combinations thereof; or (ii) performing a pregnancy termination.

11. The method of claim 1 wherein said variant caller is selected from a group consisting of Genome Analysis Toolkit (GATK) or Freebayes.

* * * * *